US011678800B2

(12) United States Patent
Booth et al.

(10) Patent No.: US 11,678,800 B2
(45) Date of Patent: *Jun. 20, 2023

(54) SUBCUTANEOUS OUTPATIENT MANAGEMENT

(71) Applicant: Aseko, Inc., Greenville, SC (US)

(72) Inventors: Robert C. Booth, Columbus, NC (US); Harry Hebblewhite, Atlanta, GA (US)

(73) Assignee: Aseko, Inc., Greenville, SC (US)

(*) Notice: Subject to any disclaimer, the term of this patent is extended or adjusted under 35 U.S.C. 154(b) by 553 days.

This patent is subject to a terminal disclaimer.

(21) Appl. No.: 16/520,936

(22) Filed: Jul. 24, 2019

(65) Prior Publication Data

US 2019/0348166 A1 Nov. 14, 2019

Related U.S. Application Data

(63) Continuation of application No. 16/124,026, filed on Sep. 6, 2018, now Pat. No. 10,403,397, which is a (Continued)

(51) Int. Cl.
*A61B 5/00* (2006.01)
*A61M 5/172* (2006.01)
(Continued)

(52) U.S. Cl.
CPC ........ *A61B 5/0022* (2013.01); *A61B 5/14503* (2013.01); *A61B 5/14532* (2013.01);
(Continued)

(58) Field of Classification Search
None
See application file for complete search history.

(56) References Cited

U.S. PATENT DOCUMENTS

| 561,422 A | 6/1896 | Minnis |
| 4,055,175 A | 10/1977 | Clemens et al. |

(Continued)

FOREIGN PATENT DOCUMENTS

| AU | 199460325 A | 8/1994 |
| AU | 2009283013 A1 | 2/2010 |

(Continued)

OTHER PUBLICATIONS

Kim, Sarah et al., Hyperglycemia control of the Nil per os patient in the intensive care unit: Introduction of a simple subcutaneous insulin algorithm, Journal of Diabetes Science and Technology, Nov. 2012, vol. 6, Issue 6, pp. 1413-1419.

(Continued)

*Primary Examiner* — Soren Harward
(74) *Attorney, Agent, or Firm* — Honigman LLP; Brett A. Krueger

(57) ABSTRACT

A method of administering insulin includes receiving subcutaneous information for a patient at a computing device and executing a subcutaneous outpatient program for determining recommended insulin dosages. The subcutaneous outpatient program includes obtaining blood glucose data of the patient from a glucometer in communication with the computing device, aggregating blood glucose measurements to determine a representative aggregate blood glucose measurement associated with at least one scheduled blood glucose time interval, and determining a next recommended insulin dosage for the patient based on the representative aggregate blood glucose measurement and the subcutaneous information. The method also includes transmitting the next recommended insulin dosage to a portable device associated with the patient. The portable device displays the next recommended insulin dosage.

15 Claims, 32 Drawing Sheets

Related U.S. Application Data continuation of application No. 15/855,315, filed on Dec. 27, 2017, now Pat. No. 10,128,002, which is a continuation of application No. 14/922,763, filed on Oct. 26, 2015, now Pat. No. 9,892,234.

(60) Provisional application No. 62/069,195, filed on Oct. 27, 2014.

(51) Int. Cl.

| | | |
|---|---|---|
| *A61B 5/145* | (2006.01) | |
| *G16H 10/60* | (2018.01) | |
| *G16H 10/40* | (2018.01) | |
| *G16H 20/17* | (2018.01) | |
| *G16H 40/67* | (2018.01) | |
| *G16H 20/60* | (2018.01) | |
| *G16H 50/20* | (2018.01) | |
| *G16Z 99/00* | (2019.01) | |

(52) U.S. Cl.
CPC ......... *A61B 5/4839* (2013.01); *A61M 5/1723* (2013.01); *G16H 10/40* (2018.01); *G16H 10/60* (2018.01); *G16H 20/17* (2018.01); *G16H 20/60* (2018.01); *G16H 40/67* (2018.01); *G16H 50/20* (2018.01); *G16Z 99/00* (2019.02); *A61M 2205/3303* (2013.01)

(56) References Cited

U.S. PATENT DOCUMENTS

| | | |
|---|---|---|
| 4,151,845 A | 5/1979 | Clemens |
| 4,206,755 A | 6/1980 | Klein |
| 4,403,984 A | 9/1983 | Ash et al. |
| 4,464,170 A | 8/1984 | Clemens et al. |
| 4,731,726 A | 3/1988 | Allen, III |
| 4,850,959 A | 7/1989 | Findl |
| 4,911,168 A | 3/1990 | Davis |
| 4,947,845 A | 8/1990 | Davis |
| 4,981,779 A | 1/1991 | Wagner |
| 5,091,190 A | 2/1992 | Kuczynski et al. |
| 5,216,597 A | 6/1993 | Beckers |
| 5,251,126 A | 10/1993 | Kahn et al. |
| 5,822,715 A | 10/1998 | Worthington et al. |
| 5,956,501 A | 9/1999 | Brown |
| 5,998,363 A | 12/1999 | Forse et al. |
| 6,024,699 A | 2/2000 | Surwit et al. |
| 6,186,145 B1 | 2/2001 | Brown |
| 6,233,539 B1 | 5/2001 | Brown |
| 6,379,301 B1 | 4/2002 | Worthington et al. |
| 6,428,825 B2 | 8/2002 | Sharma et al. |
| 6,472,366 B2 | 10/2002 | Kishino et al. |
| 6,540,672 B1 | 4/2003 | Simonsen et al. |
| 6,544,212 B2 | 4/2003 | Galley et al. |
| 6,560,471 B1 | 5/2003 | Heller et al. |
| 6,572,542 B1 | 6/2003 | Houben et al. |
| 6,575,905 B2 | 6/2003 | Knobbe et al. |
| 6,605,039 B2 | 8/2003 | Houben et al. |
| 6,615,081 B1 | 9/2003 | Boveja |
| 6,669,663 B1 | 12/2003 | Thompson |
| 6,740,072 B2 | 5/2004 | Starkweather et al. |
| 6,808,703 B2 | 10/2004 | Park et al. |
| 6,890,568 B2 | 5/2005 | Pierce et al. |
| 6,927,246 B2 | 8/2005 | Noronha et al. |
| 7,025,425 B2 | 4/2006 | Kovatchev et al. |
| 7,039,560 B2 | 5/2006 | Kawatahara et al. |
| 7,060,059 B2 | 6/2006 | Keith et al. |
| 7,108,680 B2 | 9/2006 | Rohr et al. |
| 7,137,951 B2 | 11/2006 | Pilarski |
| 7,167,818 B2 | 1/2007 | Brown |
| 7,204,823 B2 | 4/2007 | Estes et al. |
| 7,267,665 B2 | 9/2007 | Steil et al. |
| 7,282,029 B1 | 10/2007 | Poulsen et al. |
| 7,291,107 B2 | 11/2007 | Hellwig et al. |
| 7,404,796 B2 | 7/2008 | Ginsberg |
| 7,498,318 B1 | 3/2009 | Stahl et al. |
| 7,509,156 B2 | 3/2009 | Flanders |
| 7,553,281 B2 | 6/2009 | Hellwig et al. |
| 7,651,845 B2 | 1/2010 | Doyle, III et al. |
| 7,704,226 B2 | 4/2010 | Mueller, Jr. et al. |
| 7,734,323 B2 | 6/2010 | Blomquist et al. |
| 7,806,886 B2 | 10/2010 | Kanderian, Jr. et al. |
| 7,824,333 B2 | 11/2010 | Otto et al. |
| 7,837,622 B2 | 11/2010 | Itoh et al. |
| 7,853,455 B2 | 12/2010 | Brown |
| 7,877,271 B2 | 1/2011 | Brown |
| 7,901,625 B2 | 3/2011 | Brown |
| 7,904,310 B2 | 3/2011 | Brown |
| 7,912,688 B2 | 3/2011 | Brown |
| 7,920,998 B2 | 4/2011 | Brown |
| 7,949,507 B2 | 5/2011 | Brown |
| 7,985,848 B2 | 7/2011 | Woo et al. |
| 8,088,731 B2 | 1/2012 | Knudsen et al. |
| 8,117,020 B2 | 2/2012 | Abensour et al. |
| 8,185,412 B1 | 5/2012 | Harpale |
| 8,198,320 B2 | 6/2012 | Liang et al. |
| 8,204,729 B2 | 6/2012 | Sher |
| 8,206,340 B2 | 6/2012 | Arefieg |
| 8,257,300 B2 | 9/2012 | Budiman et al. |
| 8,257,735 B2 | 9/2012 | Lau et al. |
| 8,318,221 B2 | 11/2012 | Miller et al. |
| 8,329,232 B2 | 12/2012 | Cheng et al. |
| 8,333,752 B2 | 12/2012 | Veit et al. |
| 8,370,077 B2 | 2/2013 | Bashan et al. |
| 8,398,616 B2 | 3/2013 | Budiman |
| 8,420,125 B2 | 4/2013 | Webster et al. |
| 8,420,621 B2 | 4/2013 | Lai et al. |
| 8,457,901 B2 | 6/2013 | Beshan et al. |
| 8,527,208 B2 | 9/2013 | Prud'homme et al. |
| 8,532,933 B2 | 9/2013 | Duke et al. |
| 8,548,544 B2 | 10/2013 | Kircher, Jr. et al. |
| 8,571,801 B2 | 10/2013 | Anfinsen et al. |
| 8,579,879 B2 | 11/2013 | Palerm et al. |
| 8,600,682 B2 | 12/2013 | Bashan et al. |
| 8,635,054 B2 | 1/2014 | Brown |
| 8,679,016 B2 | 3/2014 | Mastrototaro et al. |
| 8,690,934 B2 | 4/2014 | Boyden et al. |
| 8,700,161 B2 | 4/2014 | Harel et al. |
| 8,703,183 B2 | 4/2014 | Lara |
| 8,718,949 B2 | 5/2014 | Blomquist et al. |
| 8,755,938 B2 | 6/2014 | Weinert et al. |
| 8,766,803 B2 | 7/2014 | Bousamra et al. |
| 8,828,390 B2 | 9/2014 | Herrera et al. |
| 8,834,367 B2 | 9/2014 | Laan et al. |
| 8,870,807 B2 | 10/2014 | Mantri et al. |
| 8,911,367 B2 | 12/2014 | Brister et al. |
| 8,919,180 B2 | 12/2014 | Gottlieb et al. |
| 8,992,464 B2 | 3/2015 | Bashan et al. |
| 2001/0002269 A1 | 5/2001 | Zhao |
| 2002/0193679 A1* | 12/2002 | Malave ................. A61M 5/172 600/407 |
| 2003/0028089 A1 | 2/2003 | Galley et al. |
| 2003/0050621 A1 | 3/2003 | Lebel et al. |
| 2003/0199445 A1 | 10/2003 | Knudsen et al. |
| 2003/0208110 A1 | 11/2003 | Mault et al. |
| 2004/0015102 A1* | 1/2004 | Cummings .......... A61B 5/7475 600/584 |
| 2004/0042272 A1 | 3/2004 | Kurata |
| 2004/0044272 A1 | 3/2004 | Moerman et al. |
| 2004/0054263 A1 | 3/2004 | Moerman et al. |
| 2004/0059201 A1* | 3/2004 | Ginsberg ........... A61B 5/14532 600/300 |
| 2005/0020681 A1 | 1/2005 | Takayama et al. |
| 2005/0049179 A1* | 3/2005 | Davidson ............... G16H 20/10 703/11 |
| 2005/0054818 A1 | 3/2005 | Brader et al. |
| 2005/0055010 A1 | 3/2005 | Pettis et al. |
| 2005/0096637 A1 | 5/2005 | Heruth |
| 2005/0171503 A1 | 8/2005 | Van Den Berghe et al. |
| 2005/0176621 A1 | 8/2005 | Brader et al. |
| 2005/0177398 A1 | 8/2005 | Watanabe et al. |
| 2005/0187749 A1 | 8/2005 | Singley |
| 2005/0192494 A1 | 9/2005 | Ginsberg |

(56) References Cited

U.S. PATENT DOCUMENTS

| | | |
|---|---|---|
| 2005/0192557 A1 | 9/2005 | Brauker et al. |
| 2005/0197621 A1 | 9/2005 | Poulsen et al. |
| 2005/0267195 A1 | 12/2005 | Mikoshiba et al. |
| 2005/0272640 A1 | 12/2005 | Doyle et al. |
| 2006/0010098 A1* | 1/2006 | Goodnow ............. G06F 19/324 |
| 2006/0040003 A1 | 2/2006 | Needleman et al. |
| 2006/0078593 A1 | 4/2006 | Strozier et al. |
| 2006/0160722 A1 | 7/2006 | Green et al. |
| 2006/0173260 A1 | 8/2006 | Gaoni et al. |
| 2006/0188995 A1 | 8/2006 | Ryan et al. |
| 2006/0224109 A1 | 10/2006 | Steil et al. |
| 2006/0264895 A1 | 11/2006 | Flanders |
| 2006/0272652 A1* | 12/2006 | Stocker ................. G16H 50/50 |
| | | 128/898 |
| 2007/0016449 A1* | 1/2007 | Cohen ................. G06F 19/3456 |
| | | 705/3 |
| 2007/0033074 A1* | 2/2007 | Nitzan ................. G06F 19/3456 |
| | | 705/3 |
| 2007/0036872 A1 | 2/2007 | Tsuboi et al. |
| 2007/0060796 A1 | 3/2007 | Kim |
| 2007/0078314 A1 | 4/2007 | Grounsell et al. |
| 2007/0078818 A1 | 4/2007 | Zivitz et al. |
| 2007/0160678 A1 | 7/2007 | Guimberteau et al. |
| 2007/0168224 A1 | 7/2007 | Letzt et al. |
| 2007/0249916 A1 | 10/2007 | Pesach et al. |
| 2007/0282186 A1 | 12/2007 | Gilmore |
| 2007/0293742 A1 | 12/2007 | Simonsen et al. |
| 2008/0097289 A1 | 4/2008 | Steil et al. |
| 2008/0119421 A1 | 5/2008 | Tuszynski et al. |
| 2008/0119705 A1 | 5/2008 | Patel et al. |
| 2008/0139511 A1 | 6/2008 | Friesen |
| 2008/0139907 A1 | 6/2008 | Rao et al. |
| 2008/0172030 A1 | 7/2008 | Blomquist |
| 2008/0188796 A1 | 8/2008 | Steil et al. |
| 2008/0214919 A1 | 9/2008 | Harmon et al. |
| 2008/0228056 A1 | 9/2008 | Blomquist et al. |
| 2008/0234943 A1 | 9/2008 | Ray et al. |
| 2008/0255707 A1 | 10/2008 | Hebblewhite et al. |
| 2008/0269585 A1 | 10/2008 | Ginsberg |
| 2008/0299079 A1 | 12/2008 | Meezan et al. |
| 2008/0306353 A1 | 12/2008 | Douglas et al. |
| 2009/0029933 A1 | 1/2009 | Velloso et al. |
| 2009/0036753 A1 | 2/2009 | King |
| 2009/0054753 A1 | 2/2009 | Robinson et al. |
| 2009/0069636 A1 | 3/2009 | Zivitz et al. |
| 2009/0099438 A1 | 4/2009 | Flanders |
| 2009/0110752 A1 | 4/2009 | Shang et al. |
| 2009/0157430 A1 | 6/2009 | Rule et al. |
| 2009/0192751 A1* | 7/2009 | Kamath ............. A61B 5/14532 |
| | | 702/104 |
| 2009/0214511 A1 | 8/2009 | Tran et al. |
| 2009/0227514 A1 | 9/2009 | Oben |
| 2009/0239944 A1 | 9/2009 | D'orazio et al. |
| 2009/0240127 A1 | 9/2009 | Ray |
| 2009/0242399 A1 | 10/2009 | Kamath et al. |
| 2009/0247982 A1 | 10/2009 | Krulevitch et al. |
| 2009/0253970 A1* | 10/2009 | Bashan ............. A61B 5/14532 |
| | | 600/316 |
| 2009/0253973 A1 | 10/2009 | Bashan et al. |
| 2009/0281519 A1 | 11/2009 | Rao et al. |
| 2009/0299152 A1 | 12/2009 | Taub et al. |
| 2009/0312250 A1 | 12/2009 | Ryu et al. |
| 2010/0016700 A1 | 1/2010 | Sieh et al. |
| 2010/0035795 A1 | 2/2010 | Boss et al. |
| 2010/0137788 A1 | 6/2010 | Braithwaite et al. |
| 2010/0145725 A1 | 6/2010 | Alferness et al. |
| 2010/0160740 A1 | 6/2010 | Cohen et al. |
| 2010/0161236 A1 | 6/2010 | Cohen et al. |
| 2010/0161346 A1 | 6/2010 | Getschmann et al. |
| 2010/0168660 A1 | 7/2010 | Galley et al. |
| 2010/0198142 A1 | 8/2010 | Sloan et al. |
| 2010/0256047 A1 | 10/2010 | Sieh et al. |
| 2010/0262434 A1 | 10/2010 | Shaya |
| 2010/0286601 A1 | 11/2010 | Yodfat et al. |
| 2010/0305545 A1 | 12/2010 | Kanderian, Jr. et al. |
| 2010/0324382 A1 | 12/2010 | Cantwell et al. |
| 2010/0331652 A1 | 12/2010 | Groll et al. |
| 2010/0331654 A1 | 12/2010 | Jerdonek et al. |
| 2010/0332142 A1 | 12/2010 | Shadforth et al. |
| 2011/0021894 A1 | 1/2011 | Mohanty et al. |
| 2011/0071365 A1 | 3/2011 | Lee et al. |
| 2011/0071464 A1 | 3/2011 | Palerm |
| 2011/0098548 A1 | 4/2011 | Budiman et al. |
| 2011/0115894 A1 | 5/2011 | Burnett |
| 2011/0119081 A1 | 5/2011 | Vespasian |
| 2011/0152830 A1 | 6/2011 | Ruchti et al. |
| 2011/0178008 A1 | 7/2011 | Arai et al. |
| 2011/0213332 A1 | 9/2011 | Mozayeny |
| 2011/0217396 A1 | 9/2011 | Oldani |
| 2011/0218489 A1 | 9/2011 | Mastrototaro et al. |
| 2011/0229602 A1 | 9/2011 | Aymard et al. |
| 2011/0286984 A1 | 11/2011 | Huang |
| 2011/0305771 A1 | 12/2011 | Sampalis |
| 2011/0313674 A1 | 12/2011 | Duke et al. |
| 2011/0319322 A1 | 12/2011 | Bashan et al. |
| 2012/0003339 A1 | 1/2012 | Minacapelli |
| 2012/0022353 A1 | 1/2012 | Bashan et al. |
| 2012/0046606 A1 | 2/2012 | Arefieg |
| 2012/0053222 A1 | 3/2012 | Gorrell et al. |
| 2012/0058942 A1 | 3/2012 | Dupre |
| 2012/0065482 A1 | 3/2012 | Robinson et al. |
| 2012/0095311 A1 | 4/2012 | Ramey et al. |
| 2012/0123234 A1 | 5/2012 | Atlas et al. |
| 2012/0197358 A1 | 8/2012 | Prescott |
| 2012/0213886 A1 | 8/2012 | Gannon et al. |
| 2012/0227737 A1 | 9/2012 | Mastrototaro et al. |
| 2012/0232519 A1 | 9/2012 | Georgiou et al. |
| 2012/0232520 A1 | 9/2012 | Sloan et al. |
| 2012/0238853 A1 | 9/2012 | Arefieg |
| 2012/0244096 A1 | 9/2012 | Xie et al. |
| 2012/0295985 A1 | 11/2012 | Miller et al. |
| 2013/0022592 A1 | 1/2013 | Vaughn et al. |
| 2013/0030358 A1 | 1/2013 | Yodfat et al. |
| 2013/0052285 A1 | 2/2013 | Song et al. |
| 2013/0109620 A1 | 5/2013 | Riis et al. |
| 2013/0144283 A1 | 6/2013 | Barman |
| 2013/0158503 A1 | 6/2013 | Kanderian, Jr. et al. |
| 2013/0165901 A1 | 6/2013 | Ruchti et al. |
| 2013/0190583 A1 | 7/2013 | Grosman et al. |
| 2013/0225683 A1 | 8/2013 | Gagnon et al. |
| 2013/0233727 A1 | 9/2013 | Tsai et al. |
| 2013/0245545 A1* | 9/2013 | Arnold ................ A61M 5/1723 |
| | | 604/66 |
| 2013/0245547 A1 | 9/2013 | El-Khatib et al. |
| 2013/0267796 A1 | 10/2013 | Enric Monte Moreno |
| 2013/0281796 A1 | 10/2013 | Pan |
| 2013/0282301 A1 | 10/2013 | Rush |
| 2013/0289883 A1 | 10/2013 | Bashan et al. |
| 2013/0309750 A1 | 11/2013 | Tajima et al. |
| 2013/0316029 A1 | 11/2013 | Pan et al. |
| 2013/0317316 A1 | 11/2013 | Kandeel |
| 2013/0331323 A1 | 12/2013 | Wu et al. |
| 2013/0338209 A1 | 12/2013 | Gambhire et al. |
| 2013/0345664 A1 | 12/2013 | Beck et al. |
| 2014/0000338 A1 | 1/2014 | Luo et al. |
| 2014/0004211 A1 | 1/2014 | Choi et al. |
| 2014/0024907 A1 | 1/2014 | Howell et al. |
| 2014/0037749 A1 | 2/2014 | Shea et al. |
| 2014/0057331 A1 | 2/2014 | Tajima et al. |
| 2014/0066735 A1 | 3/2014 | Engelhardt et al. |
| 2014/0066888 A1 | 3/2014 | Parikh et al. |
| 2014/0081196 A1 | 3/2014 | Chen |
| 2014/0128706 A1 | 5/2014 | Roy |
| 2014/0170123 A1 | 6/2014 | Alam et al. |
| 2014/0178509 A1 | 6/2014 | Jia |
| 2014/0179629 A1 | 6/2014 | Hamaker et al. |
| 2014/0194788 A1 | 7/2014 | Muehlbauer et al. |
| 2014/0213963 A1 | 7/2014 | Wu et al. |
| 2014/0296943 A1 | 10/2014 | Maxik et al. |
| 2014/0303466 A1 | 10/2014 | Fitzpatrick et al. |
| 2014/0303552 A1 | 10/2014 | Kanderian, Jr. et al. |
| 2014/0337041 A1 | 11/2014 | Madden et al. |
| 2014/0347491 A1 | 11/2014 | Connor |

(56) References Cited

U.S. PATENT DOCUMENTS

| | | |
|---|---|---|
| 2014/0349256 A1 | 11/2014 | Connor |
| 2014/0349257 A1 | 11/2014 | Connor |
| 2014/0356420 A1 | 12/2014 | Huang |
| 2014/0363794 A1 | 12/2014 | Angelides |
| 2014/0365534 A1 | 12/2014 | Bousamra et al. |
| 2014/0378381 A1 | 12/2014 | Chen et al. |
| 2014/0378793 A1 | 12/2014 | Kamath et al. |
| 2015/0018633 A1 | 1/2015 | Kovachev et al. |
| 2015/0025496 A1 | 1/2015 | Imran |
| 2015/0025903 A1 | 1/2015 | Mueller-Wolf |
| 2015/0031053 A1 | 1/2015 | Moerman |
| 2015/0037406 A1 | 2/2015 | Bernabeu Martinez et al. |

FOREIGN PATENT DOCUMENTS

| | | |
|---|---|---|
| AU | 2010330746 A1 | 7/2012 |
| CA | 2519249 A1 | 10/2004 |
| CA | 2670512 A1 | 7/2008 |
| CA | 2720302 A1 | 12/2009 |
| CA | 2720304 A1 | 12/2009 |
| CA | 2733593 A1 | 2/2010 |
| CA | 2752637 A1 | 9/2010 |
| CA | 2761647 A1 | 12/2010 |
| CA | 2766944 A1 | 1/2011 |
| CA | 2784143 A1 | 6/2011 |
| CN | 102016855 A | 4/2011 |
| CN | 102016906 A | 4/2011 |
| CN | 102300501 A | 12/2011 |
| CN | 102395310 A | 3/2012 |
| CN | 102481101 A | 5/2012 |
| CN | 102946804 A | 2/2013 |
| DE | 1082412 T1 | 10/2001 |
| EP | 461207 A1 | 12/1991 |
| EP | 483595 A2 | 5/1992 |
| EP | 557350 A1 | 9/1993 |
| EP | 573499 A1 | 12/1993 |
| EP | 768043 A2 | 4/1997 |
| EP | 862648 A1 | 9/1998 |
| EP | 910578 A2 | 4/1999 |
| EP | 925792 A2 | 6/1999 |
| EP | 1017414 A1 | 7/2000 |
| EP | 1030557 A1 | 8/2000 |
| EP | 1051141 A1 | 11/2000 |
| EP | 1067925 A1 | 1/2001 |
| EP | 1082412 A2 | 3/2001 |
| EP | 1115389 A1 | 7/2001 |
| EP | 483595 | 12/2001 |
| EP | 1173482 A1 | 1/2002 |
| EP | 1185321 A1 | 3/2002 |
| EP | 1196445 A1 | 4/2002 |
| EP | 1214596 A1 | 6/2002 |
| EP | 1305018 A1 | 5/2003 |
| EP | 1317190 A2 | 6/2003 |
| EP | 1382363 A1 | 1/2004 |
| EP | 1424074 A1 | 6/2004 |
| EP | 1482919 A1 | 12/2004 |
| EP | 1581095 A2 | 10/2005 |
| EP | 1610758 A2 | 1/2006 |
| EP | 1679009 A1 | 7/2006 |
| EP | 1698898 A2 | 9/2006 |
| EP | 1773860 A1 | 4/2007 |
| EP | 1846002 A1 | 10/2007 |
| EP | 1885392 A2 | 2/2008 |
| EP | 1915171 A2 | 4/2008 |
| EP | 1921981 A2 | 5/2008 |
| EP | 2114491 A1 | 11/2009 |
| EP | 2129277 A2 | 12/2009 |
| EP | 2139393 A2 | 1/2010 |
| EP | 2170430 A2 | 4/2010 |
| EP | 2257218 A2 | 12/2010 |
| EP | 2260423 A2 | 12/2010 |
| EP | 2260462 A2 | 12/2010 |
| EP | 2276405 A1 | 1/2011 |
| EP | 2300046 A2 | 3/2011 |
| EP | 2328608 A2 | 6/2011 |
| EP | 2352456 A1 | 8/2011 |
| EP | 2355669 A2 | 8/2011 |
| EP | 2377465 A1 | 10/2011 |
| EP | 2384750 A1 | 11/2011 |
| EP | 2393419 A1 | 12/2011 |
| EP | 2400882 A1 | 1/2012 |
| EP | 2418972 A1 | 2/2012 |
| EP | 2442719 A2 | 4/2012 |
| EP | 2448432 A1 | 5/2012 |
| EP | 2448468 A1 | 5/2012 |
| EP | 2448469 A2 | 5/2012 |
| EP | 2482712 A1 | 8/2012 |
| EP | 2516671 A1 | 10/2012 |
| EP | 2518655 A2 | 10/2012 |
| EP | 2525863 A1 | 11/2012 |
| EP | 2535831 A1 | 12/2012 |
| EP | 2552313 A2 | 2/2013 |
| EP | 2582297 A1 | 4/2013 |
| EP | 2585133 A1 | 5/2013 |
| EP | 2590559 A2 | 5/2013 |
| EP | 2596448 A1 | 5/2013 |
| EP | 2603133 A1 | 6/2013 |
| EP | 2605819 A1 | 6/2013 |
| EP | 2640373 A1 | 9/2013 |
| EP | 2641084 A1 | 9/2013 |
| EP | 2644088 A1 | 10/2013 |
| EP | 2654777 A2 | 10/2013 |
| EP | 2659407 A1 | 11/2013 |
| EP | 2666369 A1 | 11/2013 |
| EP | 2685895 A1 | 1/2014 |
| EP | 2720713 A2 | 4/2014 |
| EP | 2736404 A1 | 6/2014 |
| EP | 2742447 A2 | 6/2014 |
| EP | 2742449 A2 | 6/2014 |
| EP | 2745225 A2 | 6/2014 |
| EP | 2760335 A1 | 8/2014 |
| EP | 2763722 A2 | 8/2014 |
| EP | 2798548 A1 | 11/2014 |
| EP | 2822647 A1 | 1/2015 |
| JP | 04800928 B2 | 10/2011 |
| KR | 100527154 B1 | 11/2005 |
| KR | 1020090095073 | 9/2009 |
| KR | 2011052664 A | 5/2011 |
| KR | 2012047841 A | 5/2012 |
| RU | 2011109016 A | 9/2012 |
| WO | 1992019260 A1 | 11/1992 |
| WO | 1996009823 A1 | 4/1996 |
| WO | 1999044496 A1 | 9/1999 |
| WO | 1999063101 A2 | 12/1999 |
| WO | 2002036139 | 5/2002 |
| WO | 2003024468 | 3/2003 |
| WO | 2003077895 | 9/2003 |
| WO | 2003094927 | 11/2003 |
| WO | 2004084820 A2 | 10/2004 |
| WO | 2005041022 A1 | 5/2005 |
| WO | 2005081119 A2 | 9/2005 |
| WO | 2005081170 A2 | 9/2005 |
| WO | 2005081171 A2 | 9/2005 |
| WO | 2005081173 A1 | 9/2005 |
| WO | 2005110222 A1 | 11/2005 |
| WO | 2006022619 A2 | 3/2006 |
| WO | 2006022629 A2 | 3/2006 |
| WO | 2006022633 A1 | 3/2006 |
| WO | 2006022634 A1 | 3/2006 |
| WO | 2006022636 A1 | 3/2006 |
| WO | 2006022638 A1 | 3/2006 |
| WO | 2006044556 A2 | 4/2006 |
| WO | 2003101177 | 7/2006 |
| WO | 2006079124 A2 | 7/2006 |
| WO | 2006091918 A2 | 8/2006 |
| WO | 2006130901 A1 | 12/2006 |
| WO | 2007116226 A2 | 10/2007 |
| WO | 2007149533 A2 | 12/2007 |
| WO | 2008005761 A2 | 1/2008 |
| WO | 2008013324 A1 | 1/2008 |
| WO | 2008057213 A2 | 5/2008 |
| WO | 2008057384 A2 | 5/2008 |
| WO | 2008067245 A2 | 6/2008 |
| WO | 2008088490 A1 | 7/2008 |

(56) References Cited

FOREIGN PATENT DOCUMENTS

| | | |
|---|---|---|
| WO | 2008112078 A2 | 9/2008 |
| WO | 2008124478 A1 | 10/2008 |
| WO | 2009002455 A1 | 12/2008 |
| WO | 2009005960 A2 | 1/2009 |
| WO | 2009075925 A1 | 6/2009 |
| WO | 2009139846 A1 | 11/2009 |
| WO | 2009146119 A2 | 12/2009 |
| WO | 2009146121 A2 | 12/2009 |
| WO | 2010021879 A2 | 2/2010 |
| WO | 2010056718 A2 | 5/2010 |
| WO | 2010075350 A1 | 7/2010 |
| WO | 2010089304 A1 | 8/2010 |
| WO | 2010089305 A1 | 8/2010 |
| WO | 2010089306 A1 | 8/2010 |
| WO | 2010089307 A1 | 8/2010 |
| WO | 2010091102 A1 | 8/2010 |
| WO | 2010097796 A1 | 9/2010 |
| WO | 2010135646 A1 | 11/2010 |
| WO | 2010147659 A2 | 12/2010 |
| WO | 2011008520 A2 | 1/2011 |
| WO | 2011037607 A2 | 3/2011 |
| WO | 2011075687 A1 | 6/2011 |
| WO | 2011089600 A1 | 7/2011 |
| WO | 2011094352 A1 | 8/2011 |
| WO | 2011157402 A1 | 12/2011 |
| WO | 2012023964 A1 | 2/2012 |
| WO | 2012047800 A1 | 4/2012 |
| WO | 2012065556 A1 | 5/2012 |
| WO | 2012097064 A1 | 7/2012 |
| WO | 2012122520 A1 | 9/2012 |
| WO | 2012148252 A2 | 11/2012 |
| WO | 2012161670 A2 | 11/2012 |
| WO | 2012177963 A1 | 12/2012 |
| WO | 2013040712 A1 | 3/2013 |
| WO | 2013050309 A1 | 4/2013 |
| WO | 2013086372 A1 | 6/2013 |
| WO | 2013096769 A1 | 6/2013 |
| WO | 2013108262 A1 | 7/2013 |
| WO | 2013134548 A2 | 9/2013 |
| WO | 2013172833 A1 | 11/2013 |
| WO | 2013177565 A1 | 11/2013 |
| WO | 2014011488 A2 | 1/2014 |
| WO | 2014012084 A1 | 1/2014 |
| WO | 2014023834 A2 | 2/2014 |
| WO | 2014024201 A1 | 2/2014 |
| WO | 2014028607 A1 | 2/2014 |
| WO | 2014068007 A1 | 5/2014 |
| WO | 2014075135 | 5/2014 |
| WO | 2014075135 A1 | 5/2014 |
| WO | 2014099829 | 6/2014 |
| WO | 2014099829 A1 | 6/2014 |
| WO | 2014106263 A2 | 7/2014 |
| WO | 2014145049 A2 | 9/2014 |
| WO | 2014149535 | 9/2014 |
| WO | 2014149535 A1 | 9/2014 |
| WO | 2014149781 A1 | 9/2014 |
| WO | 2014152704 A1 | 9/2014 |
| WO | 2014162549 A1 | 10/2014 |
| WO | 2014162549 A1 | 10/2014 |
| WO | 2014164226 A2 | 10/2014 |
| WO | 2014179171 A1 | 11/2014 |
| WO | 2014187812 A1 | 11/2014 |
| WO | 2014190231 A1 | 11/2014 |
| WO | 2014202024 A1 | 12/2014 |
| WO | 2014209630 A2 | 12/2014 |
| WO | 2014209634 A1 | 12/2014 |

OTHER PUBLICATIONS

Vaidya, Anand et al., "Improving the management of diabetes in hospitalized patients: The result of a computer-based house staff training program", Diabetes Technology & Therapeutics, 2012, vol. 14, No. 7, pp. 610-618.
Lee, Joshua et al., "Indication-based ordering: A new paradigm for glycemic control in hospitalized inpatients", Journal of Diabetes Science and Technology, May 2008, vol. 2, Issue 3, pp. 349-356.
Nau, Konrad C. et al., "Glycemic Control in hospitalized patients not in intensive care: Beyond sliding-scale insulin", American Family Physician, May 1, 2010, vol. 81, No. 9, pp. 1130-1133.
International Search Report and Written Opinion for Application No. PCT/US2015/011559 dated Apr. 29, 2015.
International Search Report and Written Opinion for Application No. PCT/US2015/011086 dated Apr. 29, 2015.
International Search Report and Written Opinion for Application No. PCT/US2015/011574 dated Apr. 24, 2015.
International Search Report and Written Opinion for Application No. PCT/US2016/047806 dated Nov. 25, 2016.
Japanese Office Action for the related Application No. 2016-549782 dated May 16, 2019.

* cited by examiner

New Patient Information

| | |
|---|---|
| Name: | John Doe |
| Height: | 5' 8" |
| Weight: | 210 |
| Date of Birth: | 4/10/1938 |
| Diabetes History | |
| Age: | 75 |
| Other: | |

( SubQ )

New SubQ Patient, Custom Start

Name: John Doe  Diabetes: Yes
Patient ID: 7045162   Date of Birth: 4/10/1938

Custom start of patient on Glucommander SubQ:

Orderset Type: Basal/Bolus + Correction    TDD: 54 units
Bolus Insulin: Novolog    Basal Insulin: Lantus
Meal Bolus % of TDD: 50%    Basal % of TDD: 50%
Daily Meal Bolus Distribution:    Basal Distribution: 1 Dose Per Day
 Breakfast Bolus: 9 units    Basal Dose: 27 units
 Lunch Bolus: 9 units    Basal Time: 21:00
 Dinner Bolus: 9 units    Carb plan: 60 gm/meal
Target Range: 100 to 140    [Cancel] [Save]

FIG. 2C

SubQ Patient, Weight-based Start

208a — Name: John Doe | Diabetes: Yes
Patient ID: 7045162 | Date of Birth: 4/10/1938

116, 146

Weight-Based start: Weight(kg) [108]

216:
- Orderset Type: [Basal/Bolus + Correction ▼]  TDD: [54] units
- Bolus Insulin: [Novolog ▼]   Basal Insulin: [Lantus ▼]
- Meal Bolus % of TDD: [50% ▼]   Basal % of TDD: [50% ▼]
- Daily Meal Bolus Distribution:   Daily Basal Distribution: [1 Dose Per Day ▼]
  - Breakfast Bolus: [9] units   Basal Dose: [27] units
  - Lunch Bolus: [9] units   Carb plan: [60] gm/meal
  - Dinner Bolus: [9] units   Basal Time: [21:00 ▼]
- Target Range: [100 to 140 ▼]   [Cancel] [Save]

FIG. 2D

Current Patient (Subcutaneous) ~116,146

Name: John Doe
Patient ID: 7045162   Date of Birth: 4/10/1938   — 208a

Basal Insulin: Lantus
Insulin Type: Novolog
Last BG: 151 mg/dl (Jones, Sue)
BG Type: Breakfast
Basal Dose: 15 units (1 dose per day)
Next Meal Dose: 5 units
Target Range: 100 to 140 ▼

216a

Next BG Due:
Lunch — 430

Alarm On — 434

FIG. 2E

SmartPhone or Meter Screen

Estimated Carbohydrates ⌒116,146

Name: John Doe
Patient ID: 7045162 ⌒208a

216a

BG Value: 185 mg/dl

Please enter estimated carbohydrates for upcoming meal:

Estimated Carbohydrates: 60 gm

Cancel | Continue

Healthcare Provider Input Screen 2000

Configurable Settings:

Insulin characteristics:
    Rapid Analog Insulin (Humalog or Novalog):
        Half-life of diffusion out of injection site:
            Humalog: [HLinj]
            Novalog: [NVinj]
            Apidra:   [APinj]
        Half-life of insulin activity:
            Humalog: [HLact]
            Novalog: [NVact]
            Apidra:   [APact]

Default maximum number of days: ( MaxDays )
Selections for UpdateInterval: [    ], [    ], [    ], [    ]

Minimum # BG's in a group for use of Median = [ LimNMedian ]
Minimum # BG's in a group for use of Mean in Clinic app = [ LimNMean ]
Minimum for Mobile App of % BGmidsleep's within BGmidsleep's + BGbreakfast's = [Min%MidS]
Minimum for Clinic App of % BGmidsleep's within BGmidsleep's + BGbreakfast's = [Min%MidS]
Time-margin outside of a Bucket which indicates an incorrect flag citing said bucket= [FlagMargin]
CF Correlation constant, Correction Factor Ratio (CFR) = [CFR]
Minimum ratio of DayBuckets containing BG's to total DayBuckets within a Bucket = [Kndays]

FIG. 2G

BG-time Buckets Input Screen — 116, 146

| Name: | John Doe | | |
|---|---|---|---|
| Patient ID: | 7045162 | Date of Birth: | 4/10/1938 |

— 208a

BG Type Buckets

| Bucket Name | Start Time | End Time |
|---|---|---|
| MidSleep | 01:00 (TstartMidSleep) | 06:00 |
| Breakfast | 06:00 (TstartBreakf) | 10:00 |
| Lunch | 10:00 (TstartLunch) | 16:00 |
| Dinner | 16:00 (TstartDinner) | 21:00 |
| Bedtime | 21:00 (TstartBedtime) | 01:00 |

— 260

Ideal Mealtimes:
(Highlighted gray inside each bucket)
Methods of Adjustment

Drag & Drop on Modal Day Chart.......... ⊙

Automatic Methods:
  Width of intervals............................[___]
  Centers of intervals:
    Mean Meal Bolus Time in bucket.. ○
    Mean BG Time in bucket............ ○

Adjustment Factor (AF) Function

Smart Meter

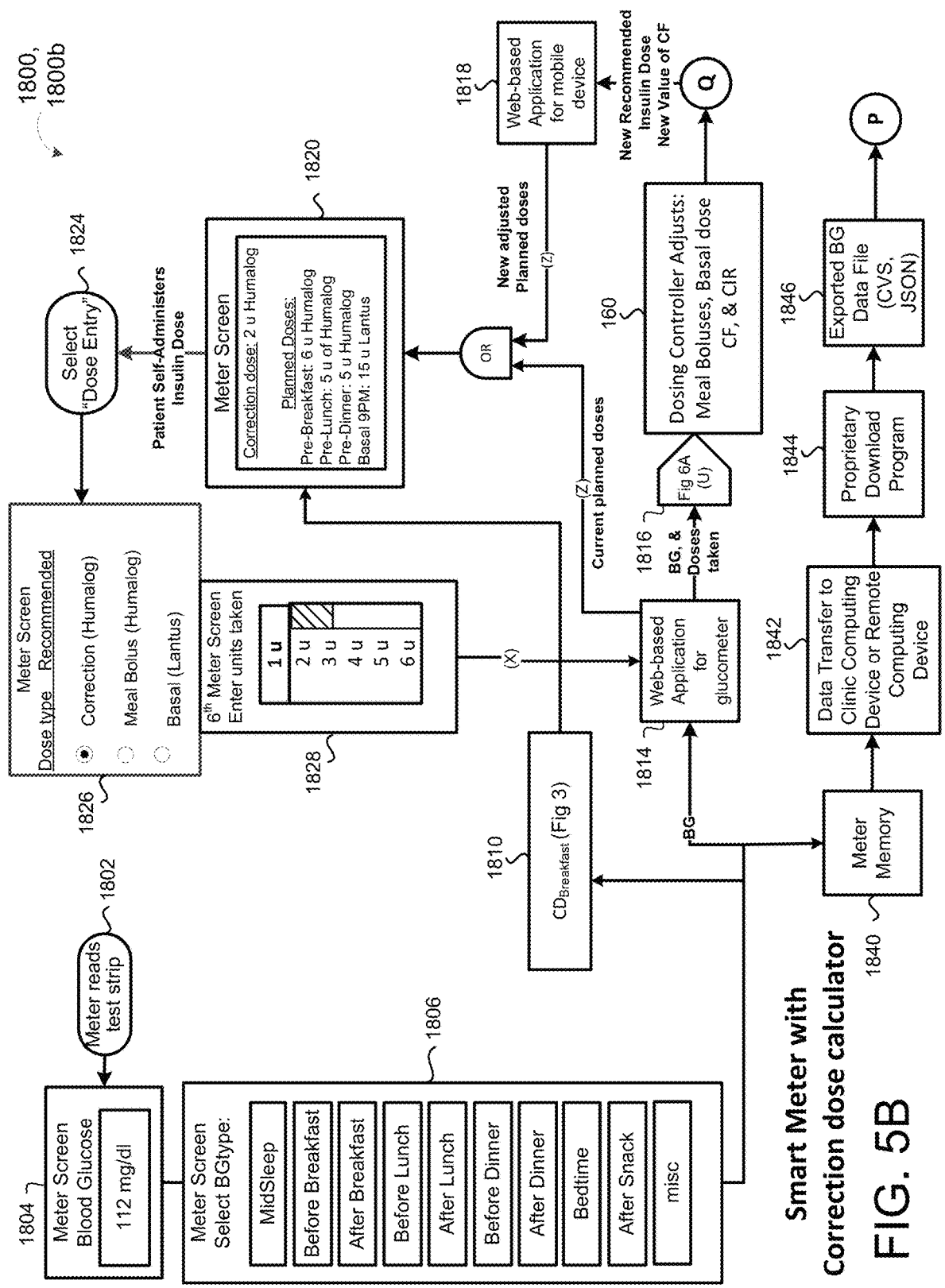
FIG. 5B Smart Meter with Correction dose calculator

SUBCUTANEOUS OUTPATIENT MANAGEMENT

CROSS REFERENCE TO RELATED APPLICATIONS

This U.S. patent application is a continuation of, and claims priority under 35 U.S.C. § 120 from, U.S. patent application Ser. No. 16/124,026, filed on Sep. 6, 2018, which is a continuation of U.S. patent application Ser. No. 15/855,315, filed on Dec. 27, 2017, which is a continuation of U.S. patent application Ser. No. 14/922,763, filed on Oct. 26, 2015, which claims priority under 35 U.S.C. § 119(e) to U.S. Provisional Application 62/069,195, filed Oct. 27, 2014. The disclosures of these prior applications are considered part of the disclosure of this application and are hereby incorporated by reference in their entireties.

TECHNICAL FIELD

This disclosure relates to a system for managing insulin administration or insulin dosing.

BACKGROUND

Managing diabetes requires calculating insulin doses for maintaining blood glucose measurements within desired ranges. Managing diabetes requires calculating insulin doses for maintaining blood glucose measurements within desired ranges. Manual calculation may not be accurate due to human error, which can lead to patient safety issues. Different institutions use multiple and sometimes conflicting protocols to manually calculate an insulin dosage. Moreover, the diabetic population includes many young children or elderly persons whom have difficulty understanding calculations for insulin doses.

SUMMARY

One aspect of the disclosure provides a method. The method includes receiving subcutaneous information for a patient at data processing hardware and executing, at the data processing hardware, a subcutaneous outpatient process for determining recommended insulin dosages. The subcutaneous outpatient process includes obtaining, at the data processing hardware, blood glucose data of the patient from a glucometer in communication with the computing device. The blood glucose data includes blood glucose measurements of the patient, blood glucose times associated with a time of each blood glucose measurement, and dosages of insulin administered by the patient associated with each blood glucose measurement. The subcutaneous outpatient process further includes determining associated ones of scheduled blood glucose time intervals for each of the blood glucose measurements using the data processing hardware based on the blood glucose times and aggregating, using the data processing hardware, the blood glucose measurements associated with at least one of the scheduled blood glucose time intervals to determine a representative aggregate blood glucose measurement associated with the at least one scheduled blood glucose time interval. The method further includes determining a next recommended insulin dosage for the patient using the data processing hardware based on the representative aggregate blood glucose measurement and the subcutaneous information and transmitting the next recommended insulin dosage to a portable device associated with the patient, the portable device displaying the next recommended insulin dosage.

Implementations of the disclosure may include one or more of the following optional features. In some implementations, the method includes transmitting the subcutaneous outpatient process to an administration device in communication with the data processing hardware. The administration device includes a doser and an administration computing device in communication with the doser. The administration computing device, when executing the subcutaneous outpatient program, causes the doser to administer insulin specified by the subcutaneous outpatient program. The data processing hardware may obtain the blood glucose data by one or more of the following ways: receiving the blood glucose data from a remote computing device in communication with the data processing hardware during a batch download process, the remote computing device executing a download program for downloading the blood glucose data from the glucometer; receiving the blood glucose data from the glucometer upon measuring the blood glucose measurement; receiving the blood glucose data from a meter manufacturer computing device in communication with the data processing hardware during a batch download process, the meter manufacturer receiving the blood glucose data from the glucometer; or receiving the blood glucose data from a patient device in communication with the data processing hardware and the glucometer, the patient device receiving the blood glucose data from the glucometer.

In some examples, the method includes aggregating, using the data processing hardware, one or more of the blood glucose measurements associated with a breakfast blood glucose time interval to determine a representative aggregate breakfast blood glucose measurement and aggregating, using the data processing hardware, one or more of the blood glucose measurements associated with a midsleep blood glucose time interval to determine a representative aggregate midsleep blood glucose measurement. The method may further include selecting, using the data processing hardware, a governing blood glucose as a lesser one of the representative aggregate midsleep blood glucose measurement or the representative aggregate breakfast blood glucose measurement and determining, using the data processing hardware, an adjustment factor for adjusting a next recommended basal dosage based on the selected governing blood glucose measurement. The method may further include obtaining, using the data processing hardware, a previous day's recommended basal dosage and determining, using the data processing hardware, the next recommended basal dosage by multiplying the adjustment factor times the previous day's recommended basal dosage.

In some implementations, the method includes aggregating, using the data processing hardware, one or more of the blood glucose measurements associated with a lunch blood glucose time interval to determine a representative aggregate lunch blood glucose measurement and selecting, using the data processing hardware, a governing blood glucose as the representative aggregate lunch blood glucose measurement. The method may also include determining, using the data processing hardware, an adjustment factor for adjusting a next recommended breakfast bolus based on the selected governing blood glucose measurement, obtaining, using the data processing hardware, a previous day's recommended breakfast bolus, and determining, using the data processing hardware, the next recommended breakfast bolus by multiplying the adjustment factor times the previous day's recommended breakfast bolus.

In some examples, the method includes aggregating, using the data processing hardware, one or more of the blood glucose measurements associated with a dinner blood glucose time interval to determine a representative aggregate dinner blood glucose measurement and selecting, using the data processing hardware, a governing blood glucose as the representative aggregate dinner blood glucose measurement. The method may also include determining, using the data processing hardware, an adjustment factor for adjusting a next recommended lunch bolus based on the selected governing blood glucose measurement, obtaining, using the data processing hardware, a previous day's recommended lunch bolus, and determining, using the data processing hardware, the next recommended lunch bolus by multiplying the adjustment factor times the previous day's recommended lunch bolus.

In some implementations, the method includes aggregating, using the data processing hardware, one or more of the blood glucose measurements associated with a bedtime blood glucose time interval to determine a representative aggregate bedtime blood glucose measurement and selecting, using the data processing hardware, a governing blood glucose as the representative aggregate bedtime blood glucose measurement. The method may also include determining, using the data processing hardware, an adjustment factor for adjusting a next recommended dinner bolus based on the selected governing blood glucose measurement, obtaining, using the data processing hardware, a previous day's recommended dinner bolus, and determining, using the data processing hardware, the next recommended dinner bolus by multiplying the adjustment factor times the previous day's recommended dinner bolus.

In some examples, the method includes aggregating, using the data processing hardware, one or more of the blood glucose measurements associated with a selected time interval to determine a representative aggregate blood glucose measurement associated with the selected time interval and selecting, using the data processing hardware, a governing blood glucose as the representative aggregate blood glucose measurement associated with the selected time interval. The method may further include determining, using the data processing hardware, an adjustment factor for adjusting a next recommended carbohydrate-to-insulin ratio governed by the selected time interval based on the selected governing blood glucose measurement, obtaining, using the data processing hardware, a previous day's recommended carbohydrate-to-insulin ratio governed by the selected time interval, and determining, using the data processing hardware, the next recommended carbohydrate-to-insulin ratio by multiplying the adjustment factor times the previous day's recommended carbohydrate-to-insulin ratio. The selected time interval may include one of lunch blood glucose interval, a dinner blood glucose time interval, or a bedtime blood glucose time interval. Each scheduled blood glucose time interval may correlate to an associated blood glucose type including one of a pre-breakfast blood glucose measurement, a pre-lunch blood glucose measurement, a pre-dinner blood glucose measurement, a bedtime blood glucose measurement and a midsleep blood glucose measurement.

In some examples, the method includes determining, using the data processing hardware, the blood glucose type for each of blood glucose measurement, the blood glucose type is tagged by the patient when measuring the blood glucose measurement. A portion of the scheduled blood glucose time intervals are associated with time intervals when the patient is consuming meals and a remaining portion of the scheduled blood glucose time intervals are associated with time intervals when the patient is not consuming meals.

In some examples, the method includes receiving, at the data processing hardware, a specified date range from a remote healthcare provider computing device in communication with the data processing hardware and aggregating, using the data processing hardware, one or more of the blood glucose measurements associated with at least one scheduled blood glucose time intervals and within the specified date range. The representative aggregate blood glucose measurement may include a mean blood glucose value for the associated scheduled blood glucose time interval. The representative aggregate blood glucose measurement may further include a median blood glucose value for the associated scheduled blood glucose time interval.

Another aspect of the disclosure provides a system. The system includes a dosing controller receiving subcutaneous information for a patient and executing a subcutaneous outpatient process for determining recommended insulin dosages, during subcutaneous outpatient program. The dosing controller includes obtaining, at the data processing hardware, blood glucose data of the patient from a glucometer in communication with the computing device, the blood glucose data including blood glucose measurements of the patient, blood glucose times associated with a time of each blood glucose measurement, and dosages of insulin administered by the patient associated with each blood glucose measurement. The system also includes determining associated ones of scheduled blood glucose time intervals for each of the blood glucose measurements based on the blood glucose times and aggregating the blood glucose measurements associated with at least one of the scheduled blood glucose time intervals to determine a representative aggregate blood glucose measurement associated with the at least one scheduled blood glucose time interval. The system also includes determining a next recommended insulin dosage for the patient based on the representative aggregate blood glucose measurement and the subcutaneous information and transmitting the next recommended insulin dosage to a portable device associated with the patient, the portable device displaying the next recommended insulin dosage.

This aspect may include one or more of the following optional features. In some implementations, the dosing controller transmits the subcutaneous outpatient process to an administration device in communication with the dosing controller. The administration device includes a doser and an administration computing device in communication with the doser. The administration computing device, when executing the subcutaneous outpatient process, causes the doser to administer insulin specified by the subcutaneous outpatient process. The dosing controller may obtain the blood glucose data by one or more of the following: receiving the blood glucose data from a remote computing device in communication with the dosing controller during a batch download process, the remote computing device executing a download program for downloading the blood glucose data from the glucometer; receiving the blood glucose data from the glucometer upon measuring the blood glucose measurement; receiving the blood glucose data from a meter manufacturer computing device in communication with the dosing controller during a batch download process, the meter manufacturer receiving the blood glucose data from the glucometer; or receiving the blood glucose data from a patient device in communication with the dosing controller and the glucometer, the patient device receiving the blood glucose data from the glucometer.

The dosing controller may further include aggregating one or more of the blood glucose measurements associated with a breakfast blood glucose time interval to determine a representative aggregate breakfast blood glucose measurement and aggregating one or more of the blood glucose measurements associated with a midsleep blood glucose time interval to determine a representative aggregate midsleep blood glucose measurement. The dosing controller may further include selecting a governing blood glucose as a lesser one of the representative aggregate midsleep blood glucose measurement or the representative aggregate breakfast blood glucose measurement, determining an adjustment factor for adjusting a next recommended basal dosage based on the selected governing blood glucose measurement, obtaining a previous day's recommended basal dosage, and determining the next recommended basal dosage by multiplying the adjustment factor times the previous day's recommended basal dosage.

The dosing controller may also include aggregating one or more of the blood glucose measurements associated with a lunch blood glucose time interval to determine a representative aggregate lunch blood glucose measurement and selecting a governing blood glucose as the representative aggregate lunch blood glucose measurement. The dosing controller may further include determining an adjustment factor for adjusting a next recommended breakfast bolus based on the selected governing blood glucose measurement, obtaining a previous day's recommended breakfast bolus, and determining the next recommended breakfast bolus by multiplying the adjustment factor times the previous day's recommended breakfast bolus.

In some examples, the dosing controller includes aggregating one or more of the blood glucose measurements associated with a dinner blood glucose time interval to determine a representative aggregate dinner blood glucose measurement and selecting a governing blood glucose as the representative aggregate dinner blood glucose measurement. The dosing controller may also include determining an adjustment factor for adjusting a next recommended lunch bolus based on the selected governing blood glucose measurement, obtaining a previous day's recommended lunch bolus, and determining the next recommended lunch bolus by multiplying the adjustment factor times the previous day's recommended lunch bolus.

In some implementations, the dosing controller includes aggregating one or more of the blood glucose measurements associated with a bedtime blood glucose time interval to determine a representative aggregate bedtime blood glucose measurement and selecting a governing blood glucose as the representative aggregate bedtime blood glucose measurement. The dosing controller may also include determining an adjustment factor for adjusting a next recommended dinner bolus based on the selected governing blood glucose measurement, obtaining a previous day's recommended dinner bolus, and determining the next recommended dinner bolus by multiplying the adjustment factor times the previous day's recommended dinner bolus.

The dosing controller may further include aggregating one or more of the blood glucose measurements associated with a selected time interval to determine a representative aggregate blood glucose measurement associated with the selected time interval and selecting a governing blood glucose as the representative aggregate blood glucose measurement associated with the selected time interval. The dosing controller may also include determining an adjustment factor for adjusting a next recommended carbohydrate-to-insulin ratio governed by the selected time interval based on the selected governing blood glucose measurement, obtaining a previous day's recommended carbohydrate-to-insulin ratio governed by the selected time interval, and determining the next recommended carbohydrate-to-insulin ratio by multiplying the adjustment factor times the previous day's recommended carbohydrate-to-insulin ratio. The selected time interval may include one of lunch blood glucose time interval, a dinner blood glucose time interval, or a bedtime blood glucose time interval. Each scheduled blood glucose time interval may correlate to an associated blood glucose type including one of a pre-breakfast blood glucose measurement, a pre-lunch blood glucose measurement, a pre-dinner blood glucose measurement, a bedtime blood glucose measurement and a midsleep blood glucose measurement. The dosing controller may determine the blood glucose type for each of blood glucose measurement. The blood glucose type is tagged by the patient when measuring the blood glucose measurement.

A portion of the scheduled blood glucose time intervals may be associated with time intervals when the patient is consuming meals and a remaining portion of the scheduled blood glucose time intervals may be associated with time intervals when the patient is not consuming meals. The dosing controller may receive a specified date range from a remote healthcare provider computing device in communication with the data processing hardware and aggregate one or more of the blood glucose measurements associated with at least one scheduled blood glucose time intervals and within the specified date range. The representative aggregate blood glucose measurement may include a mean blood glucose value for the associated scheduled blood glucose time interval. The representative blood glucose measurement may also include a median blood glucose value for the associated scheduled blood glucose time interval.

The details of one or more implementations of the disclosure are set forth in the accompanying drawings and the description below. Other aspects, features, and advantages will be apparent from the description and drawings, and from the claims.

DESCRIPTION OF DRAWINGS

FIG. 2B is a schematic view of an exemplary display for inputting patient information.

FIG. 2C-2F are schematic views of an exemplary display for inputting SubQ information relating to the patient.

FIG. 2G is a schematic view of an input screen for inputting configurable constants.

FIG. 2H is a schematic view of an input screen for inputting time-boundaries for intervals within a day.

FIG. 5B is a schematic view of an outpatient process using mobile device capable of measuring blood glucose and calculating a corrective bolus of insulin.

Like reference symbols in the various drawings indicate like elements.

DETAILED DESCRIPTION

Diabetic outpatients must manage their blood glucose level within desired ranges by using insulin therapy that includes injection dosages of insulin corresponding to meal boluses and basal dosages. Meal boluses without meals cause hypoglycemia; meals without meal boluses cause hyperglycemia. Different providers may use different methods of adjusting doses: some may use formulas of their own; some may use paper protocols that are complex and difficult for the outpatient to follow, leading to a high incidence of human error; and some may use heuristic methods. Therefore, it is desirable to have a clinical support system 100 (FIGS. 1A and 1B) that monitors outpatients' blood glucose level.

Figure 1A:
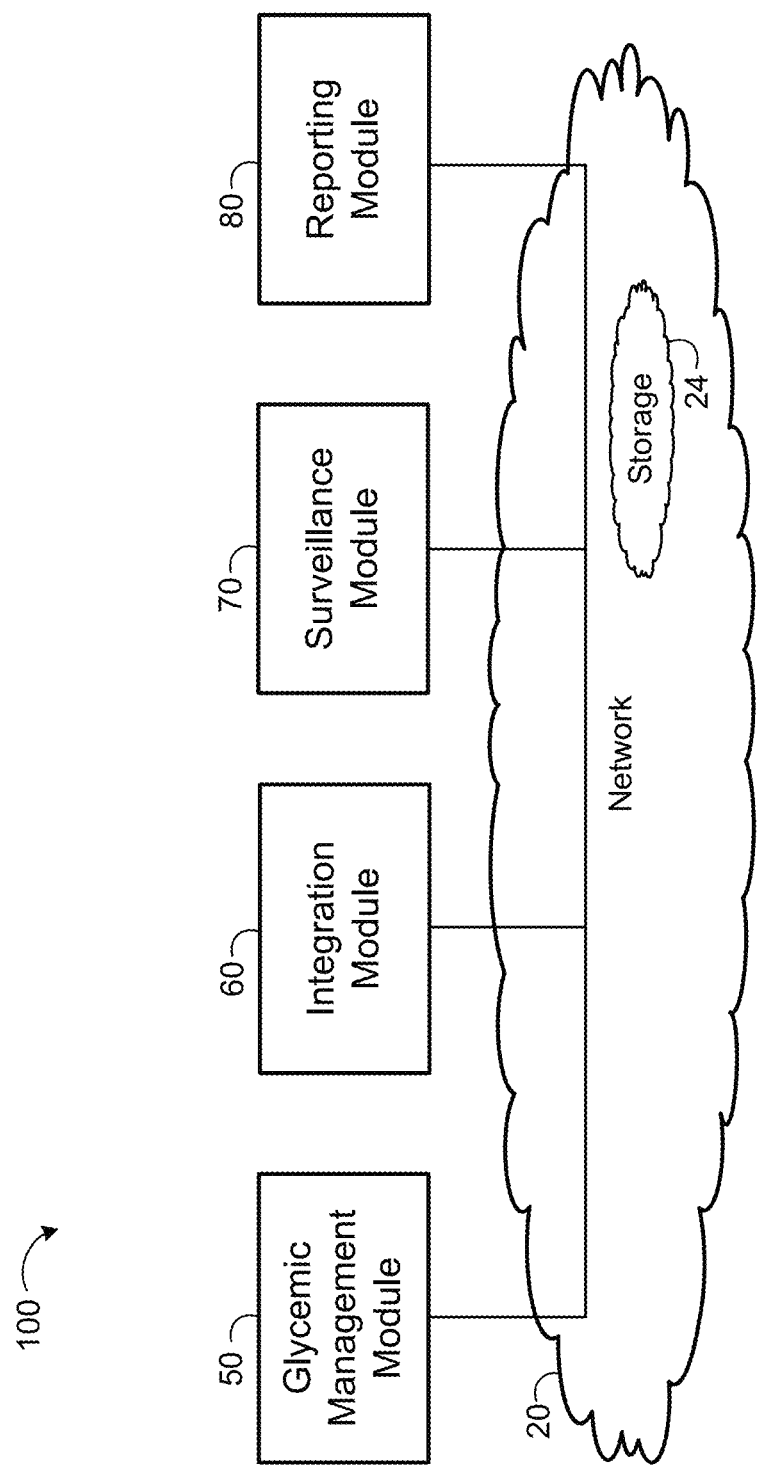
FIG. 1A is a schematic view of an exemplary system for monitoring blood glucose level of a patient.
Figure 1B:
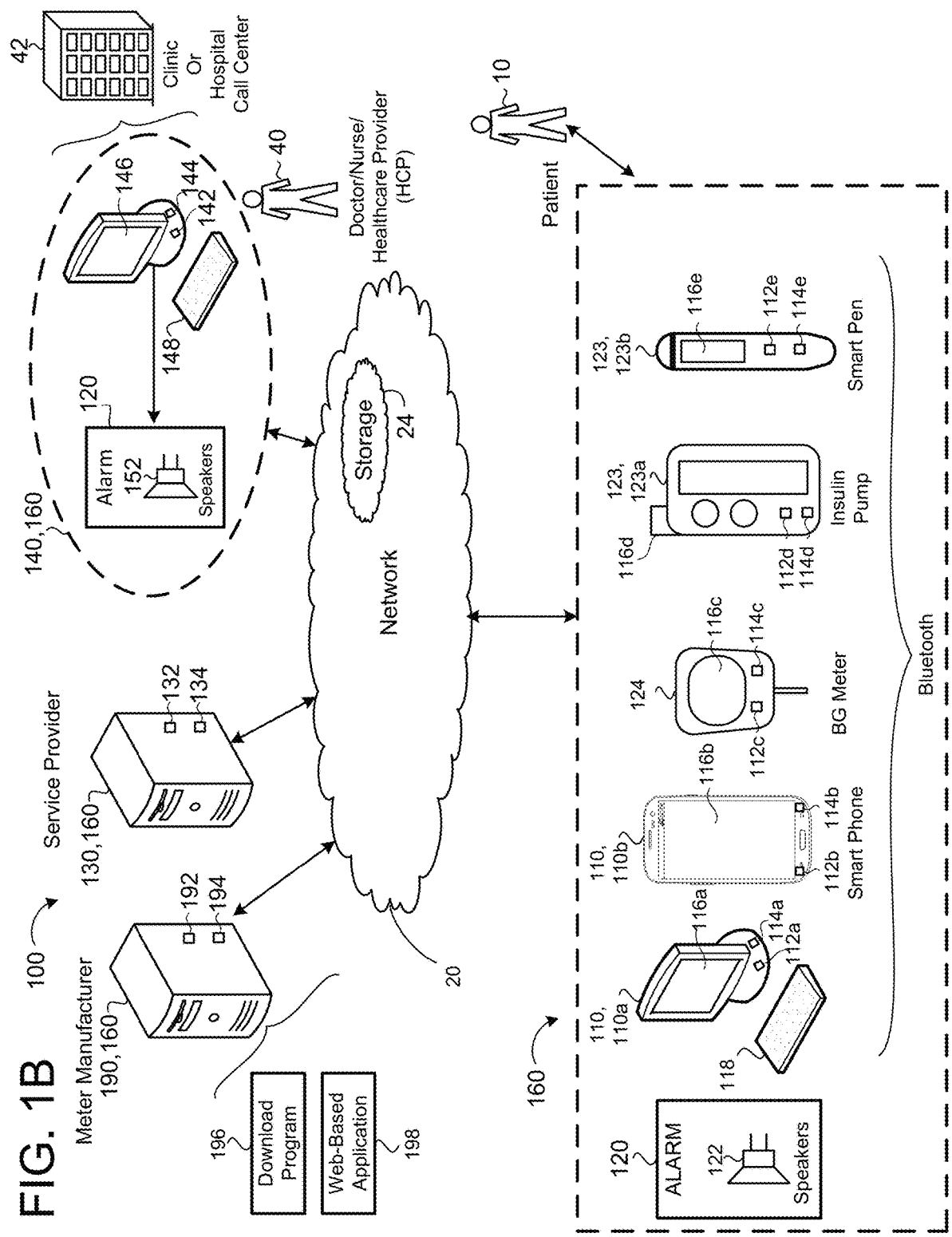
FIG. 1B is a schematic view of an exemplary system for monitoring blood glucose level of a patient.

Referring to FIG. 1A-1B, in some implementations, a clinical decision support system 100 analyzes inputted patient condition parameters for an outpatient 10 and calculates a personalized dose of insulin to bring and maintain the patient's blood glucose level into a target range $BG_{TR}$. As used herein, the patient 10 refers to an outpatient that may be located at some remote location, such as the patient's 10 residence or place of employment. As used herein, the term "clinical" may refer to a hospital call center. Moreover, the system 100 monitors the glucose levels of a patient 10 and calculates a recommended subcutaneous insulin dose to bring the patient's blood glucose into the preferred target range $BG_{TR}$ over a recommended period of time. A qualified and trained healthcare professional 40 may use the system 100 along with clinical reasoning to determine the proper dosing administered to a patient 10. Therefore, the system 100 is a glycemic management tool for evaluation a patient's current and cumulative blood glucose value BG while taking into consideration the patient's information such as age, weight, and height. The system 100 may also consider other information such as carbohydrate content of meals, insulin doses being administered to the patient 10, e.g., long-acting insulin doses for basal insulin and rapid-acting insulin doses for meal boluses and correction boluses. Based on those measurements (that may be stored in non-transitory memory 24, 114, 144), the system 100 recommends a subcutaneous basal and bolus insulin dosing recommendation or prescribed dose to adjust and maintain the blood glucose level towards a configurable (based on the patient's information) physician's determined blood glucose target range $BG_{TR}$. The system 100 also considers a patient's insulin sensitivity or improved glycemic management and outcomes. The system 100 may take into account pertinent patient information such as demographics and previous results, leading to a more efficient use of healthcare resources. Finally, the system 100 provides a reporting platform for reporting the recommendations or prescribed dose(s) to the user 40 and the patient 10. In addition, the system 100 provides faster, more reliable, and more efficient insulin administration than a human monitoring the insulin administration. The system 100 reduces the probability of human error and insures consistent treatment, due to the system's capability of storing and tracking the patient's blood glucose levels BG, which may be used for statistical studies. The system 100 provides a meal-by-meal adjustment of Meal Boluses without carbohydrate counting, by providing a dedicated subprogram that adjusts meal boluses based on the immediately preceding meal bolus and the BG that followed it. The system 100 provides a meal-by-meal adjustment of Meal Boluses with carbohydrate counting by providing a dedicated subprogram that adjusts meal boluses based a Carbohydrate-to-Insulin Ratio (CIR) that is adjusted at each meal, based on the CIR used at the immediately preceding meal bolus and the BG that followed it.

Hyperglycemia is a condition that exists when blood sugars are too high. While hyperglycemia is typically associated with diabetes, this condition can exist in many patients who do not have diabetes, yet have elevated blood sugar levels caused by trauma or stress from surgery and other complications from hospital procedures. Insulin therapy is used to bring blood sugar levels back into a normal range.

Hypoglycemia may occur at any time when a patient's blood glucose level is below a preferred target. Appropriate management of blood glucose levels for critically ill patients reduces co-morbidities and is associated with a decrease in infection rates, length of hospital stay, and death. The treatment of hyperglycemia may differ depending on whether or not a patient has been diagnosed with Type 1 diabetes mellitus, Type 2 diabetes mellitus, gestational diabetes mellitus, or non-diabetic stress hyperglycemia. The blood glucose target range $BG_{TR}$ is defined by a lower limit, i.e., a low target $BG_{TRL}$ and an upper limit, i.e., a high target $BG_{TRH}$.

Diabetes Mellitus has been treated for many years with insulin. Some recurring terms and phrases are described below:

Injection: Administering insulin by means of manual syringe or an insulin "pen," with a portable syringe named for its resemblance to the familiar writing implement.

Infusion: Administering insulin in a continuous manner by means of an insulin pump for subcutaneous insulin apparatus 123a capable of continuous administration.

Basal-Bolus Therapy: Basal-bolus therapy is a term that collectively refers to any insulin regimen involving basal insulin and boluses of insulin.

Basal Insulin: Insulin that is intended to metabolize the glucose released by a patient's the liver during a fasting state. Basal insulin is administered in such a way that it maintains a background level of insulin in the patient's blood, which is generally steady but may be varied in a programmed manner by an insulin pump 123a. Basal insulin is a slow, relatively continuous supply of insulin throughout the day and night that provides the low, but present, insulin concentration necessary to balance glucose consumption (glucose uptake and oxidation) and glucose production (glucogenolysis and gluconeogenesis). A patient's Basal insulin needs are usually about 10 to 15 mU/kg/hr and account for 30% to 50% of the total daily insulin needs; however, considerable variation occurs based on the patient 10.

Bolus Insulin: Insulin that is administered in discrete doses. There are two main types of boluses, Meal Bolus and Correction Bolus.

Meal Bolus: Taken just before a meal in an amount which is proportional to the anticipated immediate effect of carbohydrates in the meal entering the blood directly from the digestive system. The amounts of the Meal Boluses may be determined and prescribed by a physician 40 for each meal during the day, i.e., breakfast, lunch, and dinner. Alternatively, the Meal Bolus may be calculated in an amount generally proportional to the number of grams of carbohydrates in the meal. The amount of the Meal Bolus is calculated using a proportionality constant, which is a personalized number called the Carbohydrate-to-Insulin Ratio (CIR) and calculated as follows:

$$\text{Meal Insulin Bolus} = \{\text{grams of carbohydrates in the meal}\}/CIR \quad (1)$$

Correction Bolus CB: Injected immediately after a blood glucose measurement; the amount of the correction bolus is proportional to the error in the BG (i.e., the bolus is proportional to the difference between the blood glucose measurement BG and the patient's personalized Target blood glucose $BG_{Target}$). The proportionality constant is a personalized number called the Correction Factor, CF. The Correction Bolus is calculated as follows:

$$CB = (BG - BG_{Target})/CF \quad (2)$$

A Correction Bolus CB is generally administered in a fasting state, after the previously consumed meal has been digested. This often coincides with the time just before the next meal.

In some implementations, blood glucose measurements BG are aggregated using an exponentially-weighted moving average $EMA_t$ as a function for each modal day's time interval BG. The EMAt is calculated as follows:

$$EMA_t = \alpha(BG_t) + (1-\alpha)EMA_{t-1}, \quad (3)$$

wherein:

$$\alpha = 2/(n+1),$$

wherein n is the number of equivalent days averaged. In other embodiments, an arithmetic moving average is utilized that calculates the sum of all BG values in n days divided by a total count (n) of all values associated with the arithmetic average.

There are several kinds of Basal-Bolus insulin therapy including Insulin Pump therapy and Multiple Dose Injection therapy:

Insulin Pump Therapy: An insulin pump 123a is a medical device used for the administration of insulin in the treatment of diabetes mellitus, also known as continuous subcutaneous insulin infusion therapy. The device includes: a pump, a disposable reservoir for insulin, and a disposable infusion set. The pump 123a is an alternative to multiple daily injections of insulin by insulin syringe or an insulin pen and allows for intensive insulin therapy when used in conjunction with blood glucose monitoring and carbohydrate counting. The insulin pump 123a is a battery-powered device about the size of a pager. It contains a cartridge of insulin, and it pumps the insulin into the patient via an "infusion set", which is a small plastic needle or "cannula" fitted with an adhesive patch. Only rapid-acting insulin is used.

Multiple Dose Injection (MDI): MDI involves the subcutaneous manual injection of insulin several times per day using syringes or insulin pens 123b. Meal insulin is supplied by injection of rapid-acting insulin before each meal in an amount proportional to the meal. Basal insulin is provided as a once, twice, or three time daily injection of a dose of long-acting insulin. Other dosage frequencies may be available. Advances continue to be made in developing different types of insulin, many of which are used to great advantage with MDI regimens:

Long-acting insulins are non-peaking and can be injected as infrequently as once per day. These insulins are widely used for Basal Insulin. They are administered in dosages that make them appropriate for the fasting state of the patient, in which the blood glucose is replenished by the liver to maintain a steady minimum blood glucose level.

Rapid-acting insulins act on a time scale shorter than natural insulin. They are appropriate for boluses.

The decision support system 100 includes a glycemic management module 50, an integration module 60, a surveillance module 70, and a reporting module 80. Each module 50, 60, 70, 80 is in communication with the other modules 50, 60, 70, 80 via a network 20. In some examples, the network 20 (discussed below) provides access to cloud computing resources that allows for the performance of services on remote devices instead of the specific modules 50, 60, 70, 80. The glycemic management module 50 executes a program 200 (e.g., an executable instruction set) on a processor 112, 132, 142 or on the cloud computing resources. The integration module 60 allows for the interaction of users 40 and patients 10 with the system 100. The integration module 60 receives information inputted by a user 40 and allows the user 40 to retrieve previously inputted information stored on a storage system (e.g., one or more of cloud storage resources 24, a non-transitory memory 144 of an electronic medical system 140 of a clinic 42 or hospital call center (e.g., Telemedicine facility), a non-transitory memory 114 of the patient device 110, a non-transitory memory 134 of the service provider's system 130, or other non-transitory storage media in communication with the integration module 60). Therefore, the integration module 60 allows for the interaction between the users 40, patients 10, and the system 100 via a display 116, 146. The surveillance module 70 considers patient information 208a received from a user 40 via the integration module 60 and information received from a glucometer 124 that measures a patient's blood glucose value BG and determines if the patient 10 is within a threshold blood glucose value $BG_{TH}$. In some examples, the surveillance module 70 alerts the user 40 if a patient's blood glucose values BG are not within a threshold blood glucose value $BG_{TH}$. The surveillance module 70 may be preconfigured to alert the user 40 of other discrepancies between expected values and actual values based on pre-configured parameters (discussed below). For example, when a patient's blood glucose value BG drops below a lower limit of the threshold blood glucose value $BG_{THL}$. The reporting module 80 may be in communication with at least one display 116, 146 and provides information to the user 40 determined using the glycemic management module 50, the integration module 60, and/or the surveillance module 70. In some examples, the reporting module 80 provides a report that may be displayed on a display 116, 146 and/or is capable of being printed.

The system 100 is configured to evaluate a glucose level and nutritional intake of a patient 10. Based on the evaluation and analysis of the data, the system 100 calculates an insulin dose, which is administered to the patient 10 to bring and maintain the blood glucose level of the patient 10 into the blood glucose target range $BG_{TR}$. The system 100 may be applied to various devices, including, but not limited to, subcutaneous insulin infusion pumps 123a, insulin pens 123b, glucometers 124, continuous glucose monitoring systems, and glucose sensors.

In some examples the clinical decision support system 100 includes a network 20, a patient device 110, a dosing controller 160, a service provider 130, and a meter manufacturer provider 190. The patient device 110 may include, but is not limited to, desktop computers 110a or portable electronic device 110b (e.g., cellular phone, smartphone, personal digital assistant, barcode reader, personal computer, or a wireless pad) or any other electronic device capable of sending and receiving information via the network 20. In some implementations, one or more of the patient's glucometer 124, insulin pump 123a, or insulin pen 123b are capable of sending and receiving information via the network 20.

The patient device 110a, 110b includes a data processor 112a, 112b (e.g., a computing device that executes instructions), and non-transitory memory 114a, 114b and a display 116a, 116b (e.g., touch display or non-touch display) in communication with the data processor 112. In some examples, the patient device 110 includes a keyboard 118, speakers 122, microphones, mouse, and a camera.

The glucometer 124, insulin pump 123a, and insulin pen 123b associated with the patient 10 include a data processor 112c, 112d, 112e (e.g., a computing device that executes instructions), and non-transitory memory 114c, 114d, 114e and a display 116c, 116d, 116e (e.g., touch display or non-touch display in communication with the data processor 112c, 112d, 112e.

The meter manufacturer provider 190 may include may include a data processor 192 in communication with non-transitory memory 194. The data processor 192 may execute a proprietary download program 196 for downloading blood glucose BG data from the memory 114c of the patient's glucometer 124. In some implementations, the proprietary download program 196 is implemented on the health care provider's 140 computing device 142 or the patient's 10 device 110a for downloading the BG data from memory 114c. In some examples, the download program 196 exports a BG data file for storage in the non-transitory memory 24, 114, 144. The data processor 192 may further execute a web-based application 198 for receiving and formatting BG data transmitted from one or more of the patient's devices 110a, 110b, 124, 123a, 123b and storing the BG data in non-transitory memory 24, 114, 144.

The service provider 130 may include a data processor 132 in communication with non-transitory memory 134. The service provider 130 provides the patient 10 with a program 200 (see FIG. 2) (e.g., a mobile application, a web-site application, or a downloadable program that includes a set of instructions) executable on a processor 112, 132, 142 of the dosing controller 160 and accessible through the network 20 via the patient device 110, health care provider electronic medical record systems 140, portable blood glucose measurement devices 124 (e.g., glucose meter or glucometer), or portable administration devices 123a, 123b.

Figure 2A:
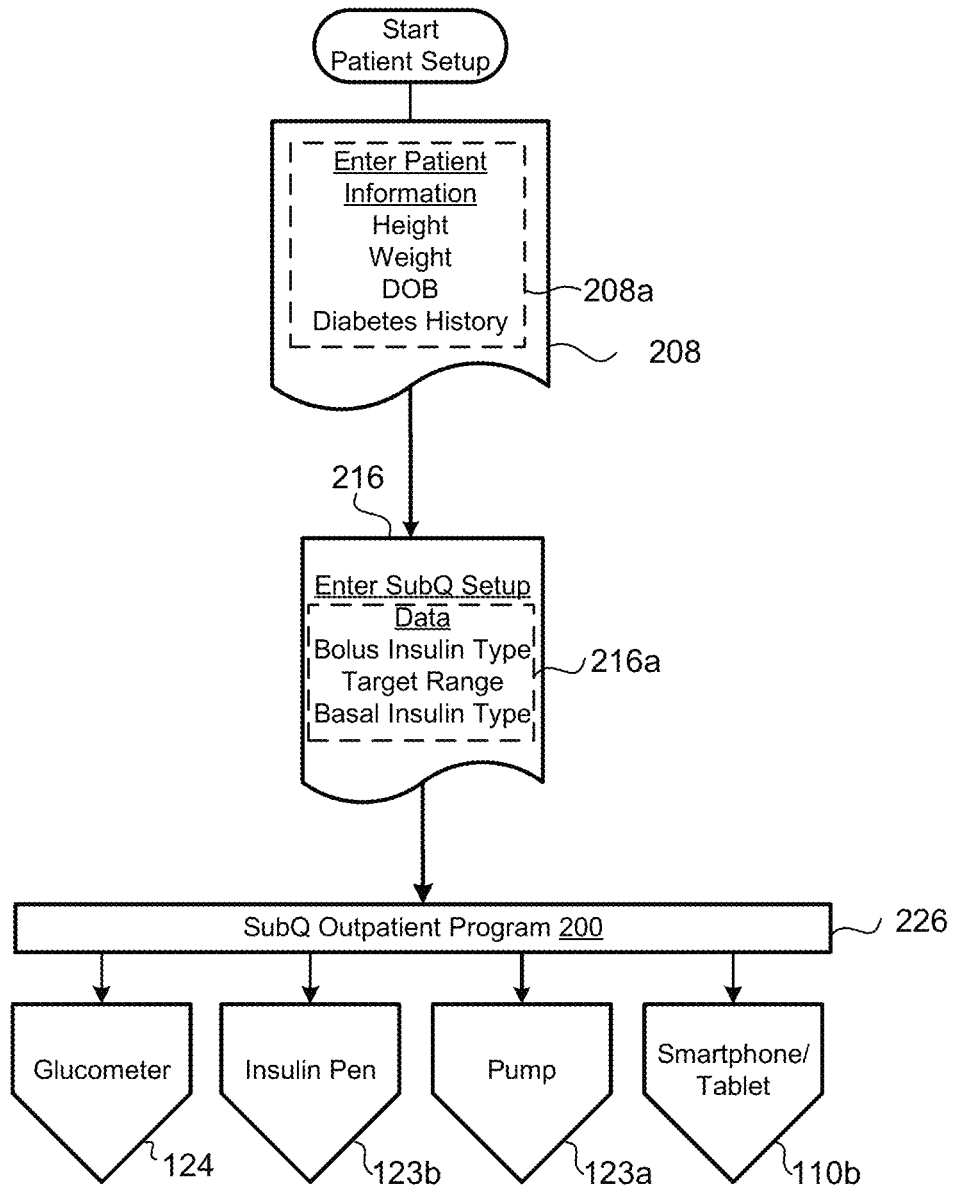
FIG. 2A is a schematic view of an exemplary program for monitoring the blood glucose level of a patient.

In some implementations, a health care provider medical record system 140 is located at a doctor's office, clinic 42, or a facility administered by a hospital (such as a hospital call center (HCP)) and includes a data processor 142, a non-transitory memory 144, and a display 146 (e.g., touch display or non-touch display). The non-transitory memory 144 and the display 146 are in communication with the data processor 142. In some examples, the health care provider electronic medical system 140 includes a keyboard 148 in communication with the data processor 142 to allow a user 40 to input data, such as patient information 208a (FIGS. 2A and 2B). The non-transitory memory 144 maintains patient records capable of being retrieved, viewed, and, in some examples, modified and updated by authorized hospital personal on the display 146.

The dosing controller 160 is in communication with the glucometer 124, insulin administration device 123a, 123b and includes a computing device 112, 132, 142 and non-transitory memory 114, 134, 144 in communication with the computing device 112, 132, 142. The dosing controller 160 executes the program 200. The dosing controller 160 stores patient related information retrieved from the glucometer 124 to determine insulin doses and dosing parameters based on the received blood glucose measurement BG.

Figure 1C:
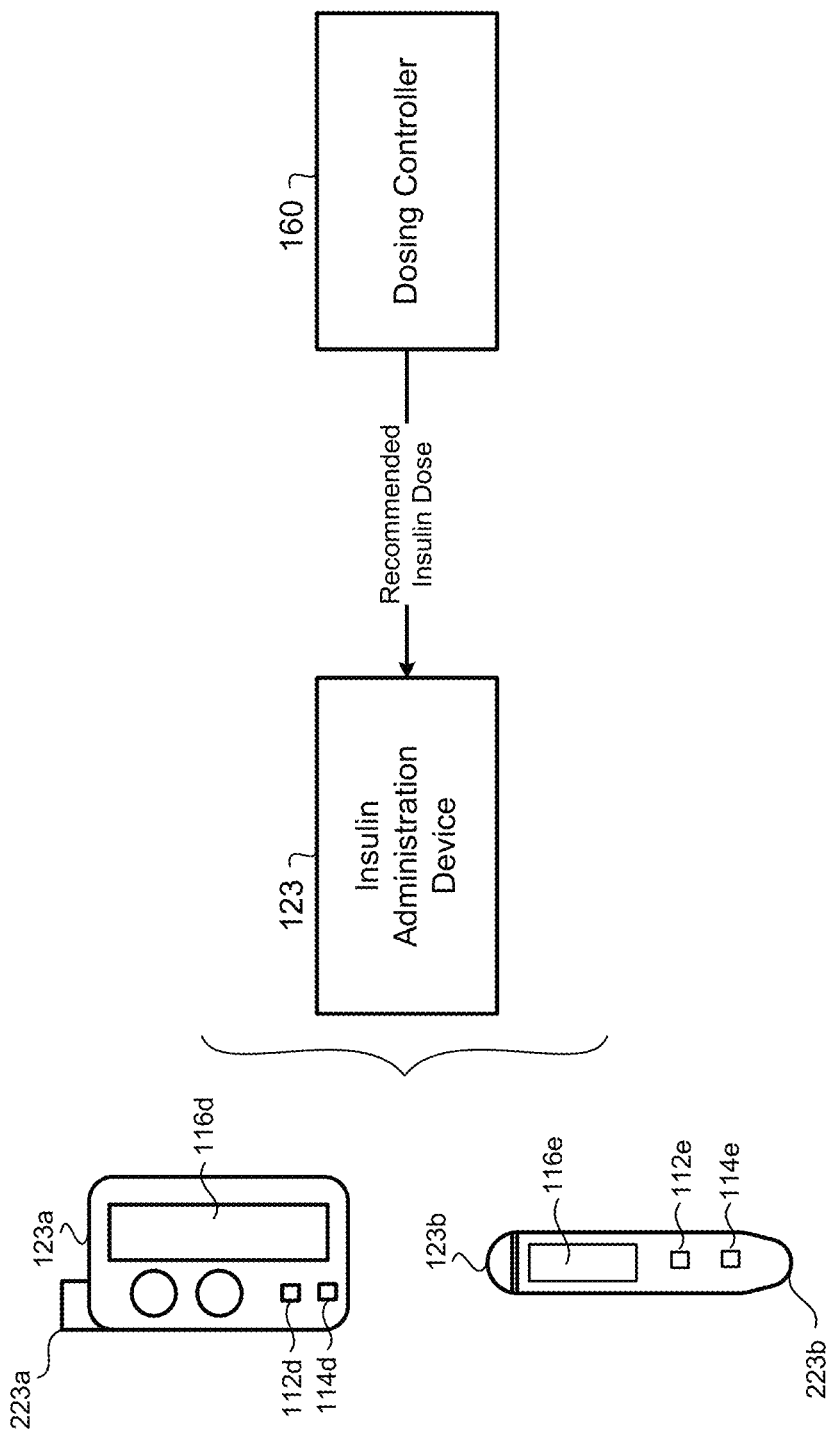
FIG. 1C is a schematic view of an exemplary administration device in communication with a dosing controller.

Referring to FIG. 1C, in some implementations, the insulin device 123 (e.g., administration device), in communication with the dosing controller 160, capable of executing instructions for administering insulin according to a subcutaneous insulin treatment program selected by the dosing controller 160. The administration device 123 may include the insulin pump 123a or the pen 123b. The administration device 123 is in communication with the glucometer 124 and includes a computing device 112d, 112e and non-transitory memory 114d, 114e in communication with the computing device 112d, 112e. The administration device 123 includes a doser 223a, 223b in communication with the administration computing device 112d, 112e for administering insulin to the patient. For instance, the doser 223a of the insulin pump 123a includes an infusion set including a tube in fluid communication with an insulin reservoir and a cannula inserted into the patient's 10 body and secured via an adhesive patch. The doser 223b of the pen 123b includes a needle for insertion into the patients 10 for administering insulin from an insulin cartridge. The administration device 123 may receive a subcutaneous insulin treatment program selected by and transmitted from the dosing controller 160, while the administration computing device 112d, 112e may execute the subcutaneous insulin treatment program. Executing the subcutaneous insulin treatment program by the administration computing device 112d, 112e causes the doser 223a, 223b to administer doses of insulin specified by the subcutaneous insulin treatment program. For instance, units for the doses of insulin may be automatically set or dialed in by the administration device 123a, 123b and administered via the doser 223a, 223b to the patient 10. Accordingly, the administration devices 123a, 123b may be "smart" administration devices capable of communicating with the dosing controller 160 to populate recommended doses of insulin for administering to the patient 10. In some examples, the administration devices 123a, 123b may execute the dosing controller 160 on the administration computing devices 112d, 112e to calculate the recommended doses of insulin for administering to the patient 10.

The network 20 may include any type of network that allows sending and receiving communication signals, such as a wireless telecommunication network, a cellular telephone network, a time division multiple access (TDMA) network, a code division multiple access (CDMA) network, Global system for mobile communications (GSM), a third generation (3G) network, fourth generation (4G) network, a satellite communications network, and other communication networks. The network 20 may include one or more of a Wide Area Network (WAN), a Local Area Network (LAN), and a Personal Area Network (PAN). In some examples, the network 20 includes a combination of data networks, telecommunication networks, and a combination of data and telecommunication networks. The patient device 110, the service provider 130, and the hospital electronic medical record system 140 communicate with each other by sending and receiving signals (wired or wireless) via the network 20. In some examples, the network 20 provides access to cloud computing resources, which may be elastic/on-demand computing and/or storage resources 24 available over the network 20. The term 'cloud' services generally refers to a service performed not locally on a user's device, but rather delivered from one or more remote devices accessible via one or more networks 20.

Referring to FIGS. 1B and 2A-2F, the program 200 receives parameters (e.g., patient condition parameters) inputted via the client device 110, the service provider 130, and/or the clinic system 140, analyzes the inputted parameters, and determines a personalized dose of insulin to bring and maintain a patient's blood glucose level BG into a preferred target range $BG_{TR}$ for a SubQ outpatient program 200 (FIG. 2A).

In some implementations, before the program 200 begins to receive the parameters, the program 200 may receive a username and a password (e.g., at a login screen displayed on the display 116, 146) to verify that a qualified and trained healthcare professional 40 is initiating the program 200 and entering the correct information that the program 200 needs to accurately administer insulin to the patient 10. The system 100 may customize the login screen to allow a user 40 to reset their password and/or username. Moreover, the system 100 may provide a logout button (not shown) that allows the user 40 to log out of the system 100. The logout button may be displayed on the display 116, 146 at any time during the execution of the program 200.

The decision support system 100 may include an alarm system 120 that alerts a user 40 at the clinic 42 (or hospital call center) when the patient's blood glucose level BG is outside the target range $BG_{TR}$. The alarm system 120 may produce an audible sound via speaker 122 in the form of a beep or some like audio sounding mechanism. For instance, the alarm system 120 may produce an audible sound via a speaker 122 of the mobile device 110b In some examples, the alarm system 120 displays a warning message or other type of indication on the display 116a-e of the patient device 110 to provide a warning message. The alarm system 120 may also send the audible and/or visual notification via the network 20 to the clinic system 140 (or any other remote station) for display on the display 146 of the clinic system 140 or played through speakers 152 of the clinic system 140.

For commencing a SubQ outpatient process 1800 (FIGS. 5A and 5B), the program 200 prompts a user 40 to input patient information 208a at block 208. The user 40 may input the patient information 208a, for example, via the user device 140 or via the health care provider medical record systems 140 located at a clinic 42 (or a doctor's office or HCP). The user 40 may input new patient information 208a as shown in FIG. 2B. The program 200 may retrieve the patient information 208a from the non-transitory memory 144 of the clinic's electronic medical system 140 or the non-transitory memory 114 of the patient device 110 (e.g., where the patient information 208a was previously entered and stored). The patient information 208a may include, but is not limited to, a patient's name, a patient's identification number (ID), a patient's height, weight, date of birth, diabetes history, physician name, emergency contact, hospital unit, diagnosis, gender, room number, and any other relevant information.

Referring to FIGS. 2A and 2C-2F, the program 200 at block 216 further requests the user 40 to enter SubQ information 216a for the patient 10, such as patient diabetes status, subcutaneous Orderset Type ordered for the patient 10 (e.g., "Fixed Carbs/meal" that is intended for patients on a consistent carbohydrate diet, total daily dosage (TDD), bolus insulin type (e.g., Novolog), basil insulin type (e.g., Lantus) and frequency of distribution (e.g., 1 dose per day, 2 doses per day, 3 doses per day, etc.), basil time, basal percentage of TDD, meal bolus percentage of TDD, daily meal bolus distribution (e.g., breakfast bolus, lunch bolus and dinner bolus), or any other relevant information. In some implementations, TDD is calculated following a period on Intravenous Insulin in accordance with equation:

$$TDD = \text{QuickTransitionConstant} * M_{Trans} \tag{4A}$$

where QuickTransitionConstant is usually equal to 1000, and $M_{Trans}$ is the patient's multiplier at the time of initiation of the SubQ transition process. In other implementations, the TDD is calculated by a statistical correlation of TDD as a function of body weight. The following equation is the correlation used:

$$TDD = 0.5 * \text{Weight(kg)} \tag{4B}$$

In other implementations, the patient's total daily dose TDD is calculated in accordance with the following equation:

$$TDD = (BG_{Target} - K) * (M_{Trans}) * 24 \tag{4C}$$

where $M_{Trans}$ is the patient's multiplier at the time of initiation of the SubQ transition process.

Figure 10:
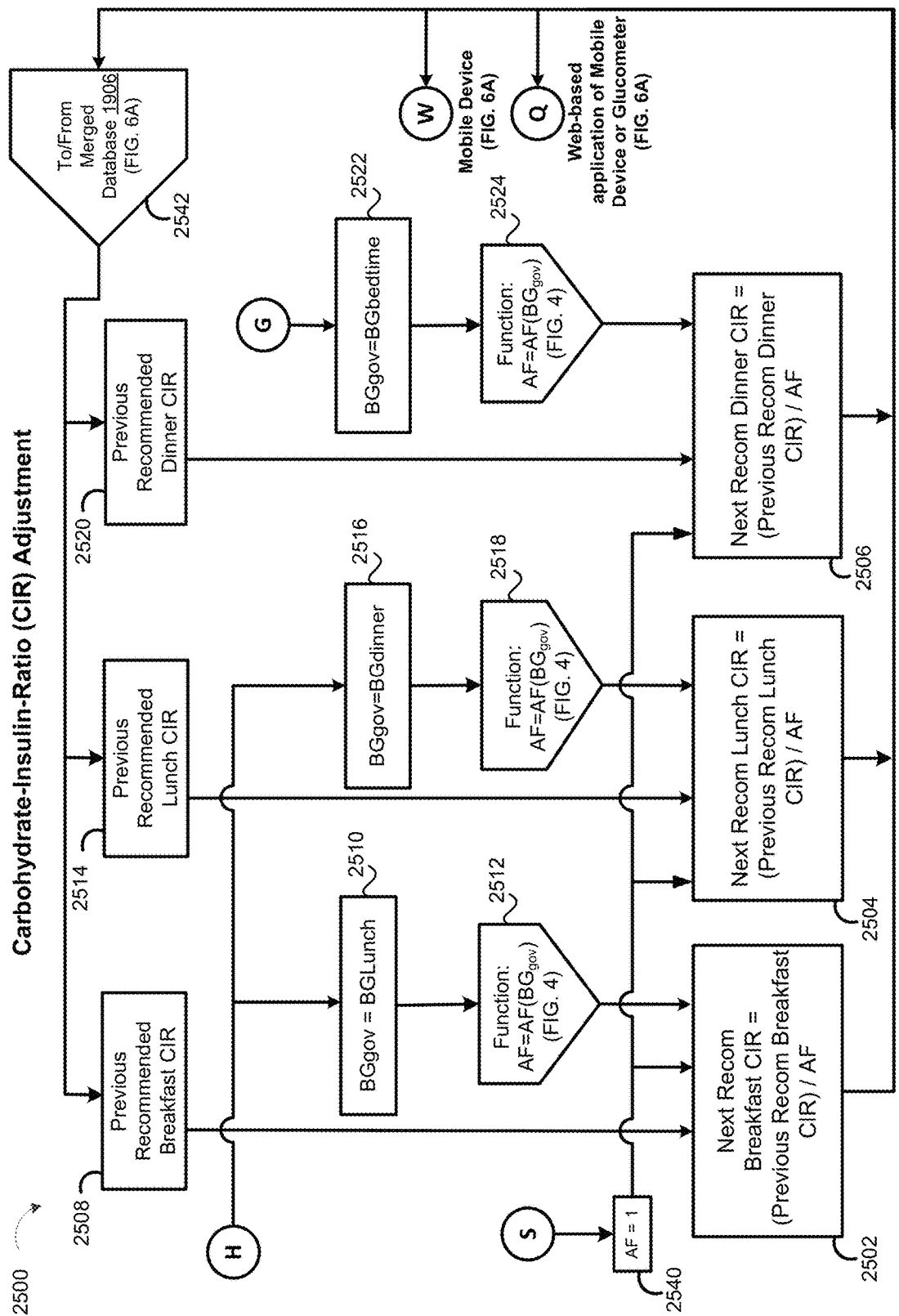
FIG. 10 is a schematic view of an exemplary carbohydrate-insulin-ratio adjustment process.
Figure 13:
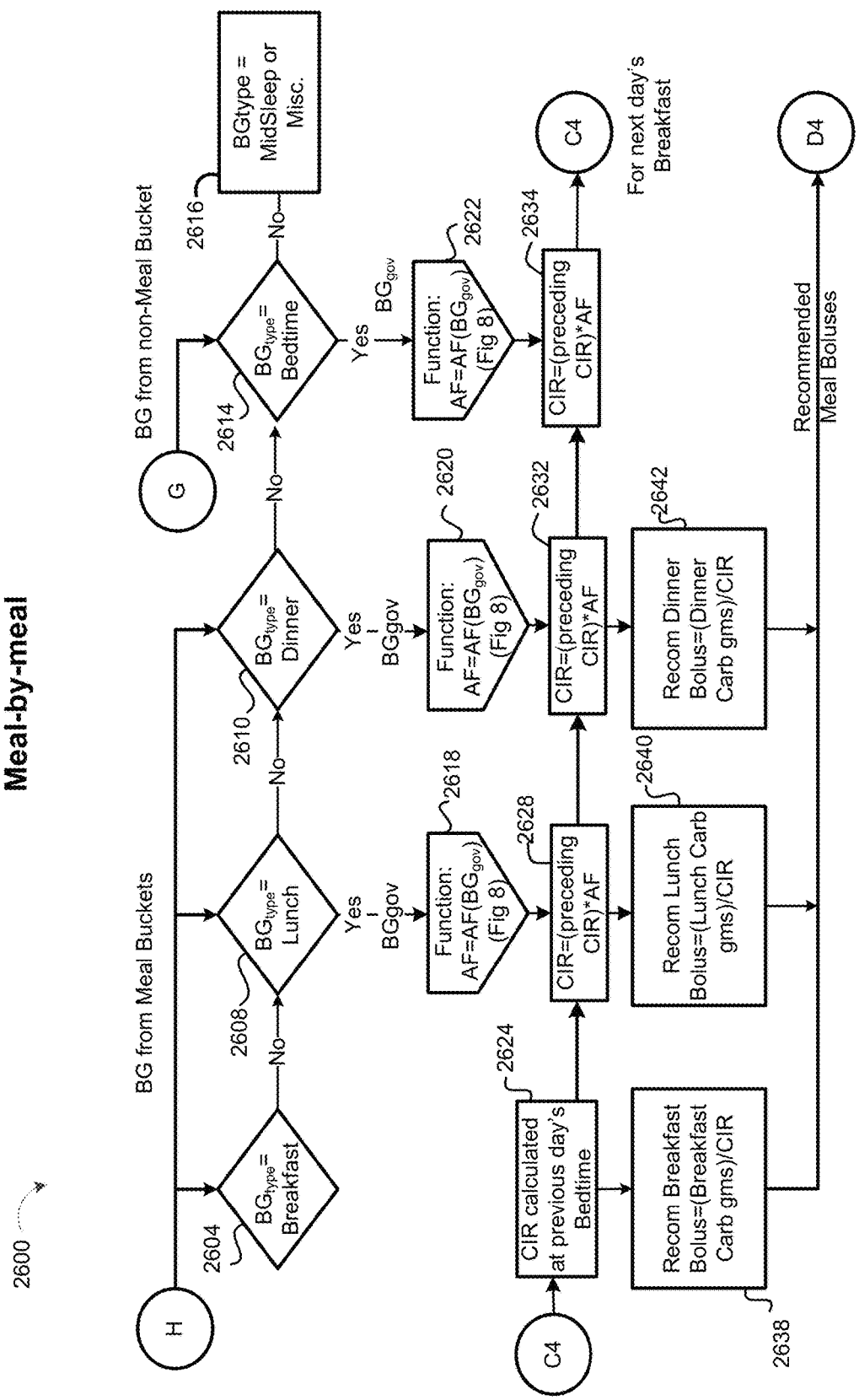
FIG. 13 is a schematic view of an exemplary carbohydrate-insulin-ratio adjustment process on a meal-by-meal basis.

In some implementations, the patient SubQ information 216a is prepopulated with default parameters, which may be adjusted or modified. In some examples, portions of the patient SubQ information 216 are prepopulated with previously entered patient subcutaneous information 216a. The program 200 may prompt the request to the user 40 to enter the SubQ information 216a on the display 116 of the patient device 110. In some implementations, the subcutaneous insulin process 1800 prompts the request on the display 116 for a custom start of new SubQ patients (FIG. 2C) being treated with the SubQ outpatient process 1800. In some examples, the program 200 prompts the request on the display 116 for a weight-based start of SubQ patients being treated with the SubQ outpatient process 1800 as shown in FIG. 2D. For instance, the user 40 may input the weight (e.g., 108 kg) of the patient 10, and in some examples, the TDD is calculated using EQ. 4B based on the patient's weight. As shown in FIG. 2E, the user 40 may further enter a schedule for when blood glucose BG measurements are required 430 (e.g., Next BG Due: Lunch) for the patient 10 and whether or not an alarm 434 is to be activated. For instance, if a BG measurement is below a threshold value, or if the patient has not submitted a BG measurement during Lunch, the alarm system 120 may generate a warning sound via speakers 122 to alert the patient 10 that a BG measurement is required. The alarm may sound on one or more of the patient's portable devices 110a, 110b, 124, 123a, 123b. As shown in FIG. 2F, the patient 10 may enter a number of carbohydrates for the upcoming meal (e.g., 60) such that adjustment of Meal Boluses with carbohydrate counting can be calculated by EQ. 1 based upon the Carbohydrate-to-Insulin Ratio (CIR). In some implementations, the CIR is associated with the BGtype or Bucket, and adjusted on a daily basis by process 2500 (FIG. 10). In other implementations, the CIR is adjusted at each meal, based on the CIR used at the immediately preceding meal bolus and the BG measurement occurring after that meal bolus by process 2600 (FIG. 13).

The program 200 flows to block 216, where the user 40 enters patient subcutaneous information 216a, such as bolus insulin type, target range, basal insulin type and frequency of distribution (e.g., 1 dose per day, 2 doses per day, 3 doses per day, etc.), patient diabetes status, subcutaneous type ordered for the patient (e.g., Basal/Bolus and correction that is intended for patients on a consistent carbohydrate diet, frequency of patient blood glucose measurements, or any other relevant information. In some implementations, the patient subcutaneous information 216a is prepopulated with default parameters, which may be adjusted or modified. When the user 40 enters the patient subcutaneous information 216a, the user selects the program 200 to execute the SubQ outpatient process 1800 at block 226.

In some implementations, the user 40 selects to initiate a subcutaneous outpatient program 200 (FIG. 2A) executing on the dosing controller 160 to provide recommended insulin dosing (bolus/basal) for a patient 10 equipped with one or more portable devices 110a, 110b, 124, 123a, 123b. The user 40 may configure the subcutaneous outpatient program 200 by selecting the portable devices used by the patient 10. Selection of block 124 indicates information for the patient's glucometer 124, including communication capabilities with other devices and/or the network 20. Selection of block 123b indicates that the patient 10 uses an insulin pen 123b for administering insulin. Information for the pen 123b may be provided that includes communication capabilities with other devices and/or the network 20. In some examples, the pen 123b is a "smart" that may include an administration computing device 112e in communication with the dosing controller 160 for administering insulin to the patient 10. Selection of block 123a indicates that the patient 10 uses an insulin pump 123a for administering insulin. Information for the pump 123a may be provided that includes communication capabilities with other devices and/or the network 20. In some examples, the pen 123b is a "smart" pen that may include the administration computing device 112d in communication with the dosing controller 160 for administering insulin to the patient 10. Selection of block 110b indicates information for the patient's 10 smartphone 110b or tablet, including communication capabilities with the glucometer 124 and/or the insulin administration devices 123a, 123b, For instance, the smartphone 110b may communicate with the glucometer 124 via Bluetooth or other connection to download BG data from the memory 114c of the glucometer, and transmit the downloaded BG data through the network 20. In other examples, the smartphone 110b may receive recommended insulin doses over the network 20 from the dosing controller 160 and provide the recommended insulin doses to the glucometer 124 and/or insulin administration device 123a, 123b.

In some implementations, some functions or processes are used within the SubQ outpatient program 200 (FIG. 2) and SubQ outpatient process 1800 (FIGS. 5A and 5B) such as determining the general and pre-meal correction (FIG. 3), determining the adjustment factor AF (FIG. 4), and hypoglycemia treatment.

Figure 3:
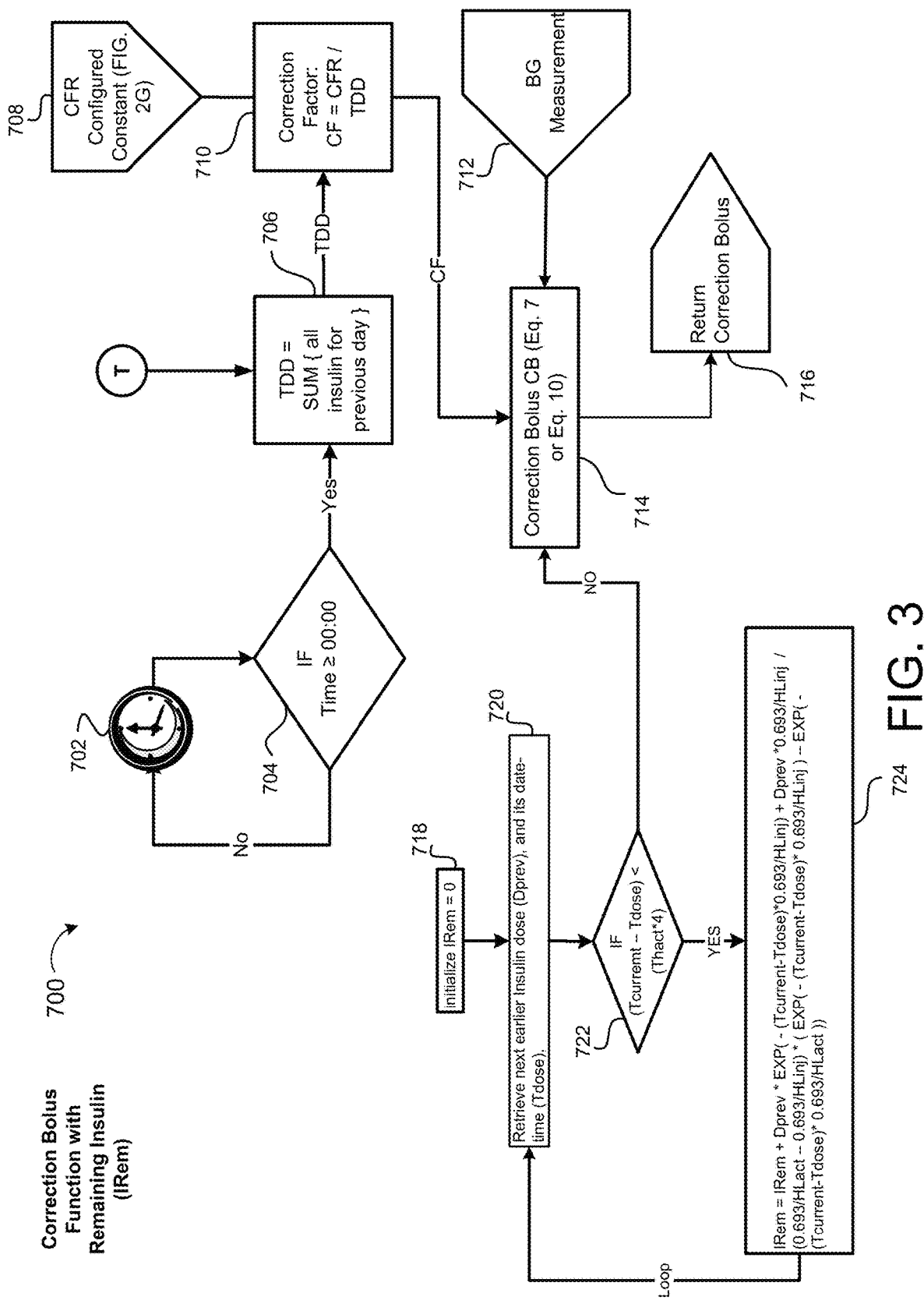
FIG. 3 is a schematic view of an exemplary correction boluses process.

Referring to FIG. 3, correction boluses CB are used in the SubQ outpatient program 200 (FIG. 2) and process 1800 (FIG. 5A) (FIG. 5B); because of this, correction boluses CB may be incorporated into a function having variables such as the blood glucose measurement BG of a patient 10, a patient's personalized target blood glucose $BG_{Target}$, and a correction factor CF. Thus, correction boluses CB are described as a function of the blood glucose measurement BG, the target blood glucose $BG_{Target}$, and the correction factor CF (see EQ. 7 below). The process 700 calculates the correction bolus CB immediately after a blood glucose value BG of a patient 10 is measured. Once a calculation of the correction bolus CB is completed, the patient 10 administers the correction bolus CB to the patient 10, right after the blood glucose value BG is measured and used to calculate the correction bolus CB.

In some examples, the process 700 may determine the total daily dose TDD of insulin once per day, for example, every night at midnight or at the next opening of the given patient's record after midnight. Other times may also be available. In addition, the total daily dose TDD may be calculated more frequently during the day, in some examples, the total daily dose TDD is calculated more frequently and considers the total daily dose TDD within the past 24 hours. The process 700 provides a timer 702, such as a countdown timer 702, where the timer 702 determines the time the process 700 executes. The timer 702 may be a count up timer or any other kind of timer. When the timer 702 reaches its expiration or reaches a certain time (e.g., zero for a countdown timer 702), the timer 702 executes the process 700. The counter 702 is used to determine at what time the process 700, at block 704, calculates the total daily dose TDD. If the counter is set to 24 hours for example, then decision block 704 checks if the time has reached 24 hours, and when it does, then the process 700 calculates the total daily dose TDD of insulin. Block 706 may receive insulin dosing data from a merged database 1906 (FIG. 6A) within the non-transitory memory 24, 114, 144 via Entry Point T. The correction bolus process 700 determines a total daily dose of insulin TDD, based on the following equation:

$$TDD = \text{Sum over previous day (all basal+all meal boluses+all correction boluses)} \tag{5A}$$

For some configurations, the TDD is calculated as the sum of the latest recommended insulin doses:

$$\text{Alternate } TDD = \text{Sum of (latest recommended basal+ latest recommended Breakfast Bolus+Latest Recommended Lunch Bolus+Latest Recommended Dinner Bolus)} \tag{5B}$$

After the process 700 determines the total daily dose TDD of insulin at block 706, the process 700 determines a Correction Factor CF immediately thereafter at block 710, using the calculated total daily dose TDD from block 706 and EQ. 5. The correction factor CF is determined using the following equation:

$$CF = CFR/TDD \tag{6}$$

where CFR is a configurable constant stored in the non-transitory memory 24, 114, 144 of the system and can be changed from the setup screen (FIG. 2D). At block 708, the process 700 retrieves the configurable constant CFR value from the non-transitory memory 24, 114, 144 to calculate the correction factor CF at block 710. The configurable constant CFR is determined from a published statistical correlation and is configurable by the hospital, nurses and doctors. The flexibility of modifying the correction constant CF, gives the system 100 flexibility when a new published configurable constant CFR is more accurate than the one being used. In some examples, the configurable constant CFR is a configurable constant set to 1700, other values may also be available. In some examples, the total daily dose TDD and CF are determined once per day (e.g., at or soon after midnight).

Once the correction factor CF is determined in EQ. 6, the process 700 determines the correction bolus insulin dose at block 714 using the following equation:

$$CB=(BG-BG_{Target})/CF) \quad (7)$$

where BG is the blood glucose measurement of a patient 10 retrieved at block 712, $BG_{Target}$ is the patient's personalized Target blood glucose, and CF is the correction factor. The process 700 returns the correction bolus CB at block 716. Rapid-acting analog insulin is currently used for Correction Boluses because it responds quickly to a high blood glucose BG. Also rapid acting analog insulin is currently used for meal boluses; it is usually taken just before or with a meal (injected or delivered via a pump). Rapid-acting analog insulin acts very quickly to minimize the rise of patient's blood sugar which follows eating.

A Correction Bolus CB is calculated for a blood glucose value BG at any time during the program 200. Pre-meal Correction Boluses CB, are calculated using EQ. 7. In the Pre-meal Correction Bolus equation (7) there is no need to account for Remaining Insulin $I_{Rem}$ because sufficient time has passed for almost all of the previous meal bolus to be depleted. However, post-prandial correction boluses (after-meal correction boluses) are employed much sooner after the recent meal bolus and use different calculations that account for remaining insulin $I_{Rem}$ that remains in the patient's body after a recent meal bolus. Rapid-acting analog insulin is generally removed by a body's natural mechanisms at a rate proportional to the insulin remaining $I_{Rem}$ in the patient's body, causing the remaining insulin $I_{Rem}$ in the patient's body to exhibit a negative exponential time-curve. Manufacturers provide data as to the lifetime of their insulin formulations. The data usually includes a half-life or mean lifetime of the rapid-acting analog insulin. The half-life of the rapid-acting analog insulin may be converted to mean lifetime by the conversion formula:

$$\text{mean lifetime=Half-life}*\ln(2) \quad (8A)$$

where ln(2) is the natural logarithm {base e} of two.

In some implementations, the process 700 accounts for post-prandial correction boluses by determining if there is any remaining insulin $I_{Rem}$ in the patient's body to exhibit a negative exponential time-curve. At block 718, process 700 initializes a loop for determining $I_{Rem}$ by setting $I_{Rem}$ equal to zero, and retrieves a next earlier insulin dose (Dprev) and the associated data-time ($T_{Dose}$) at block 720.

The brand of insulin being used is associated with two half-life parameters: the half-life of the insulin activity (HLact) and the half-life of the process of diffusion of the insulin from the injection site into the blood (HLinj). Since the manufacturers and brands of insulin are few, the program 200 maintains the two half-lives of each insulin brand as configurable constants. These configurable constants can be input by a healthcare provider using an input screen of FIG. 2G. For instance, the display 146 of the healthcare provider computing system 140 can display the input screen 2000 to enable the healthcare provider to input the configurable constants.

For a single previous dose of insulin Dprev, given at a time $T_{Dose}$, the insulin remaining in the patient's body at the current time $T_{current}$ refers to the Remaining Insulin $I_{Rem}$. The derivation of the equation for IRem involves a time-dependent two-compartment model of insulin: The insulin in the injection site Iinj(t) and the "active" insulin in the blood and cell membrane, Iact(t). The differential equation for Iinj(t) is:

$$dIinj/dt=-(0.693/HLinj)*Iinj(t). \quad (8B)$$

The differential equation for Iact(t) is:

$$dIact(t)/dt=(0.693/HLinj)*Iinj(t)-(0.693/HLact)*Iact(t) \quad (8C)$$

Equations 8B and 8C are simultaneous linear first-order differential equations. The solutions must be added together to represent the total insulin remaining, $I_{Rem}$. The final result can be written as a time-dependent factor that can be multiplied by the initial dose Dprev to obtain the time-dependent total remaining insulin IRem.

Process 700 determines, at block 724, $I_{Rem}$ by multiplying the previous single dose of insulin Dprev {e.g. a Meal Bolus, Correction Bolus, or combined bolus} times a time-dependent factor as follows:

$$I_{Rem}(\text{single dose})=Dprev*\text{EXP}(-(T_{Current}-T_{Dose}) \\ *0.693/HLinj)+D0*0.693/HLinj/(0.693/HLact- \\ 0.693/HLinj)+Dprev*(\text{EXP}(-(T_{Current}-T_{Dose}) \\ *0.693/HLinj)-\text{EXP}(-(T_{Current}-T_{Dose})*0.693/ \\ HLact)) \quad (9A)$$

The Remaining Insulin $I_{Rem}$ may account for multiple previous doses occurring in a time window looking backwards within a lifetime of the insulin being used. For example, $I_{Rem}$ may be associated with a configurable constant within the range of 4 to 7 hours that represents the lifetime of rapid analog insulin. For example, $I_{Rem}$ may be determined as follows:

$$I_{Rem}=\text{sum of } [I_{Rem}(\text{single dose}) \text{ over all doses in the within the lifetime of the insulin being used}] \quad (9B)$$

Process 700 iteratively determines $I_{Rem}$ in the loop until, at block 722, the difference between the current time $T_{Current}$ and the time at which the bolus was administered $T_{Dose}$ is greater than a time related to the lifetime of the insulin used. Thus, when block 722 is "NO", process 700 calculates, at block 714, a post meal correction bolus CBpost that deducts the remaining insulin $I_{Rem}$ in the patient's body as follows:

$$CB_{post} = \frac{(BG - BG_{Target})}{CF} - I_{Rem} \quad (10)$$

In some examples, Post Meal Correction doses $CB_{post}$ (EQ. 10) are taken into consideration only if they are positive (units of insulin), which means a negative value post meal correction bolus $CB_{Post}$ cannot be used to reduce the meal bolus portion of a new combined bolus.

Figure 4:
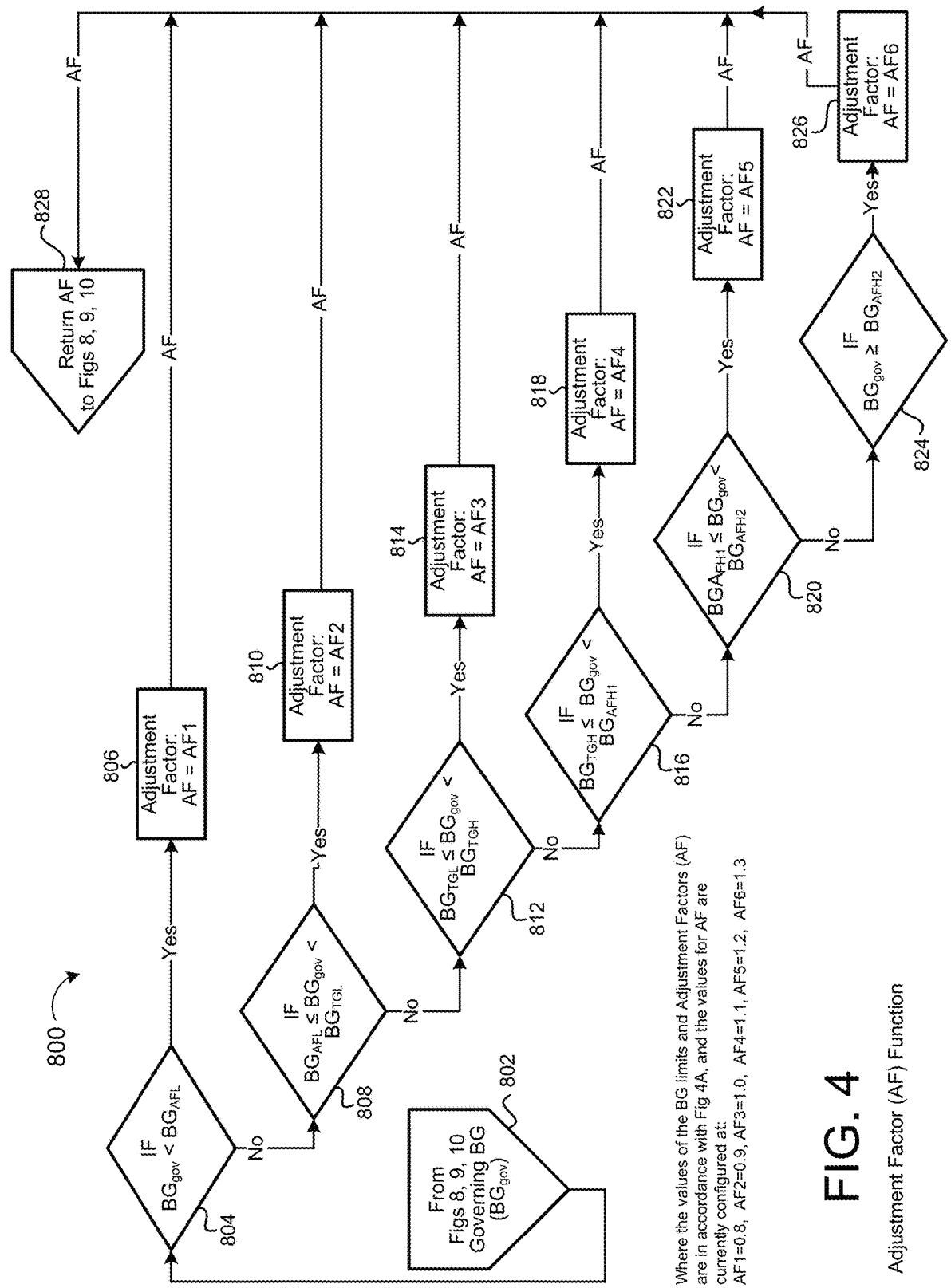
FIG. 4 is a schematic view of an exemplary adjustment factor process.

Referring to FIG. 4, process 800 describes a function that determines an Adjustment Factor AF based on an input of a Governing Blood GlucoseBGgov. The Adjustment Factor AF is used by the SubQ outpatient process 1800 (FIGS. 5A and 5B) for calculating a next recommended basal dose using a basal adjustment process 2300 (FIG. 8), for calculating next recommended meal boluses (e.g., Breakfast, Lunch, and Dinner Boluses) using a meal bolus adjustment process 2400 (FIG. 9), and for calculating a next recommended Carbohydrate-Insulin-Ratio (CIR) using CIR adjustment process 2500 (FIG. 10). An insulin adjustment process 2300, 2400, applied to Basal doses and Meal Boluses, determines an adjusted Recommended Basal dose RecBasal, or a Recommended Meal Bolus RecMealBol, by applying a unit-less Adjustment Factor AF to the preceding recommendation of the same dose, RecBasal$_{prev}$, or RecMealBol$_{prev}$. All dose adjustments are governed by a Governing Blood Glucose value BG$_{gov}$. The Governing Blood Glucose values BG$_{gov}$ in the process are selected based on the criteria of preceding the previous occurrence of the dose to be adjusted by a sufficient amount of time for the effect (or lack of effect) of the insulin to be observable and measurable in the value of the BG$_{gov}$.

At block 802, the adjustment factor process 800 receives the Governing Glucose value BG$_{gov}$ from non-transitory memory 24, 114, 144, since the adjustment factor AF is determined using the Governing Glucose value BG$_{gov}$. To determine the adjustment factor AF, the adjustment factor process 800 considers the blood glucose target range BG$_{TR}$ (within which Basal doses and Meal Boluses, are not changed), which is defined by a lower limit, i.e., a low target BG$_{TRL}$ and an upper limit, i.e., a high target BG$_{TRH}$. As previously discussed, the target range BG$_{TR}$ is determined by a doctor 40 and entered manually (e.g., using the patient device 110 or the medical record system 140, via, for example, a drop down menu list displayed on the display 116, 146). Each target range BG$_{TR}$ is associated with a set of configurable constants including a first constant BG$_{AFL}$, a second constant BG$_{AFH1}$, and a third constant BG$_{AFH2}$ shown in the below table.

TABLE 1

Target Range Settings

| Input Ranges | BG$_{AFL}$ | BG$_{TRL}$ | BG$_{TRH}$ | BG$_{AFH1}$ | BG$_{AFH2}$ |
|---|---|---|---|---|---|
| 70-100 | 70 | 70 | 100 | 140 | 180 |
| 80-120 | 80 | 80 | 120 | 160 | 200 |
| 100-140 | 70 | 100 | 140 | 180 | 220 |
| 120-160 | 90 | 120 | 160 | 200 | 240 |
| 140-180 | 110 | 140 | 180 | 220 | 260 |

The adjustment factor process 800 determines, at block 804, if the Governing Glucose value BG$_{gov}$ is less than or equal to the first constant BG$_{AFL}$ (BG$_{gov}$<=BG$_{AFL}$), if so then at block 806, the adjustment factor process 800 assigns the adjustment factor AF to a first pre-configured adjustment factor AF1 shown in Table 2.

If, at block 804, the Governing Glucose value BG$_{gov}$ is not less than the first constant BG$_{AFL}$, (i.e., BG$_{gov}$≥BG$_{AFL}$), then at block 808, the adjustment factor process 800 determines if the Governing Glucose value BG$_{gov}$ is greater than or equal to the first constant BG$_{AFL}$ and less than the low target BG$_{TRL}$ of the target range BG$_{TR}$ (BG$_{AFL}$≤BG$_{gov}$<BG$_{TRL}$). If so, then the adjustment factor process 800 assigns the adjustment factor AF to a second pre-configured adjustment factor AF2, at block 810. If not, then at block 812, the adjustment factor process 800 determines if the Governing Glucose value BG$_{gov}$ is greater than or equal to the low target BG$_{TRL}$ of the target range BG$_{TR}$ and less than the high target level BG$_{TRH}$ of the target range BG$_{TR}$ (BG$_{TRL}$≤BG$_{gov}$<BG$_{TRH}$). If so, then the adjustment factor process 800 assigns the adjustment factor AF to a third pre-configured adjustment factor AF3, at block 814. If not, then at block 816, the adjustment factor process 800 determines if the Governing Glucose value BG$_{gov}$ is greater than or equal to the high target level BG$_{TRH}$ of the target range BG$_{TR}$ and less than the second constant BG$_{AFH1}$ (BG$_{TRH}$≤BG$_{gov}$<BG$_{AFH1}$). If so, then the adjustment factor process 800 assigns the adjustment factor AF to a fourth pre-configured adjustment factor AF4, at block 818. If not, then at block 820, the adjustment process 800 determines if the Governing Glucose value BG$_{gov}$ is greater than or equal to the second constant BG$_{AFH1}$ and less than the third constant BG$_{AFH2}$ (BG$_{AFH1}$≤BG$_{gov}$<BG$_{AFH2}$). If so, then the adjustment factor process 800 assigns the adjustment factor AF to a fifth pre-configured adjustment factor AF5, at block 822. If not, then at block 824, the adjustment process 800 determines that the Governing Glucose value BG$_{gov}$ is greater than or equal to the third constant BG$_{AFH2}$ (BG$_{gov}$≥BG$_{AFH2}$); and the adjustment factor process 800 assigns the adjustment factor AF to a sixth pre-configured adjustment factor AF6, at block 826. After assigning a value to AF the adjustment factor process 800 returns the adjustment factor AF to the process requesting the adjustment factor AF at block 828 (e.g., the SubQ outpatient process 1800 (FIG. 5A) (FIG. 5B)).

TABLE 2

Configurable values for Adjustment Factor AF

| | |
|---|---|
| AF1 = | 0.8 |
| AF2 = | 0.9 |
| AF3 = | 1 |
| AF4 = | 1.1 |
| AF5 = | 1.2 |
| AF6 = | 1.3 |

Figure 5A:
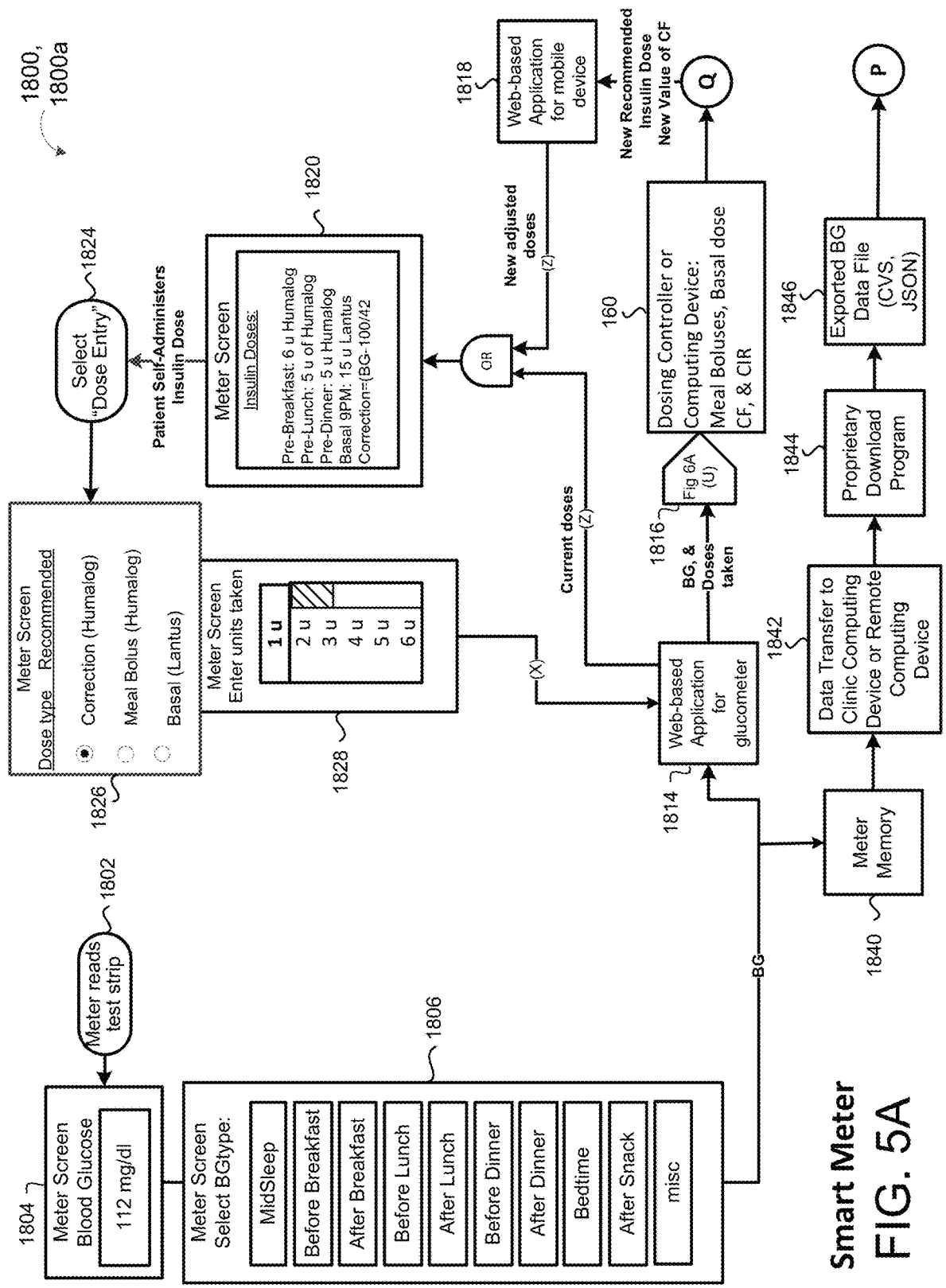
FIG. 5A is a schematic view of an outpatient process using a mobile device capable of measuring blood glucose.

Referring to FIGS. 2A, 5A, and 5B, if the user 40 initiates a subcutaneous output patient process 1800 through selection of program 200 at block 226, the subcutaneous outpatient process 1800 utilizes the patient information 208a and the patient SubQ information 216a input by the user 40 or the patient 10, as shown in FIGS. 2B-2F.

Basal insulin is for the fasting insulin-needs of a patient's body. Therefore, the best indicator of the effectiveness of the basal dose is the value of the blood glucose BG after the patient 10 has fasted for a period of time. Meal Boluses are for the short-term needs of a patient's body following a carbohydrate-containing meal. Therefore, the best indicator of the effectiveness of the Meal Bolus is a blood glucose measurement BG tested about one mean insulin-lifetime iLifeRapid after the Meal Bolus, where the lifetime is for the currently-used insulin type. For rapid-acting analog insulin the lifetime is conveniently similar to the time between meals.

FIG. 5A and FIG. 5B show the SubQ outpatient process 1800a, 1800b, respectively, for a patient 10 using patient portable devices including the glucometer 124 and the patient device 110a or smartphone 110b for communicating with, or optionally executing, the dosing controller 160, based upon selection of blocks 110b and 124 of program 200 (FIG. 2A) The SubQ outpatient process 1800 may be similarly utilized for portable devices including the insulin pen 123b and the infusion pump 123a having "smart" capabilities for communicating with the dosing controller 160.

Referring to FIG. 5A the process 1800a executes by a blood glucose meter without a built-in correction dose calculator. The SubQ outpatient process 1800a begins with a patient's 18 manual entry of a blood glucose measurement BG at block 1802. The SubQ outpatient process 1800a, at block 1804, displays the result of the blood glucose measurement (e.g., 112 mg/dl) and prompts the patient 10 to select a BGtype from a dropdown list 1806. The selection list is provided so that the patient can choose the appropriate BGtype indicating which meal and whether the blood glucose measurement BG is "Before-Meal" or "After-Meal", and also listing other key blood glucose testing times such as Bedtime and MidSleep (generally about 03:00 AM). The BGtype is associated with a blood glucose time BGtime associated with a time of measuring the blood glucose measurement. In the example shown, the SubQ outpatient process 1800*a* allows the patient to select a pre-breakfast blood glucose measurement, a pre-lunch blood glucose measurement, a pre-dinner blood glucose measurement, a bedtime blood glucose measurement, or a midsleep blood glucose measurement.

In some implementations, the glucometer 124 may not be configured to display the BGtype selections as shown at block 1806, and instead, determines if the time at which the blood glucose BG was measured BGtime falls within one of a number of scheduled blood glucose time buckets, that are contiguous so as to cover the entire day with no gaps. Further, the BGtypes are provided with Ideal BG Time Intervals, where each ideal scheduled time is associated with an interval configured with a start time margin ($M_{Start}$) and an end time margin ($M_{End}$). Moreover, each interval may be associated with a corresponding BGtype: pre-breakfast blood glucose measurement, a pre-lunch blood glucose measurement, a pre-dinner blood glucose measurement, a bedtime blood glucose measurement, or a midsleep blood glucose measurement Referring to FIG. 5B, the process 1800*b* uses a blood glucose meter having a built-in correction dose calculator. Using a processor of the glucometer 124, the SubQ outpatient process 1800, at block 1810, determines a Correction Dose of insulin for the selected (or determined) BGtype (e.g., pre-breakfast) using the following equation (based on EQ. 2):

$$CB_{Breakfast} = (BG_{Breakfast} - BG_{Target})/CF \qquad (11)$$

Additionally or alternatively, the Correction Dose may be determined using the Correction Dose Function of process 700 (FIG. 3). For example, when the blood glucose meter does not include a built-in correction dose calculator, process 1800*a* (FIG. 5A) may allow a healthcare provider, via the dosing controller 160, to load the Correction Factor (CF) upon the glucometer 124 based upon an immediately preceding BG measurement. In other examples, meters or other devices may use the correction dose formula of process 700 (FIG. 3), which may incorporate a deduction for the Remaining Insulin $I_{Rem}$.

The SubQ outpatient process 1800*b* (FIG. 5B), at block 1820, displays the Correction Dose for the BGtype determined at block 1810 on a Meter Screen of the glucometer display 116*c*. In some implementations, the SubQ outpatient process 1800*a* (FIG. 5A) stores blood glucose data BGdata, including the recent correction dose CD, the blood glucose measurement BG, the BGtype, and the $BG_{TIME}$, in the glucometer's 124 memory 114*c* at block 1840, and at a later time, the SubQ outpatient process 1800 uses a batch process, at blocks 1842-1846, for downloading the data from the glucometer 124 to the non-transitory 24, 114, 144 for the dosing controller 160 to retrieve for determining or adjusting recommended insulin doses for the patient 10. In some examples, the glucometer 124 transfers data to the computing device 112 or 142 at block 1842, and a proprietary download program 196 provided by the manufacturer of the glucometer 124 executes on the computing device 112 or 142 to download the data at block 1844. For instance, the patient 12 may connect the glucometer 124 to the computing device 112 when the patient 12 visits a clinic 42 during a regular check-up. The data transfer may be facilitated by connecting the glucometer 124 to the computing device 112 or 142 using Bluetooth, Infrared, near field communication (NFC), USB, or serial cable, depending upon the configuration of the glucometer 124. The SubQ outpatient process 1800*a*, at block 1846, exports the data downloaded by the proprietary download program 196 as a formatted data file for storage within the non-transitory 24, 114, 144 for the dosing controller 160 to retrieve when determining or adjusting insulin parameters for the patient 10 at entry point P. For example, the exported data file may be a CVS file or JSON file accessible to the computing devices 132, 142 of the dosing controller 160.

Referring back to block 1806, in some implementations, the SubQ outpatient process 1800*a*, 1800*b* provides the blood glucose BG data, including the recent correction dose CD, the blood glucose measurement BG, the BGtype, and the $BG_{TIME}$, in real time to a web-based application 198 of the manufacturer of the glucometer 124 at block 1814, and in turn, the web-based application 198 of the manufacturer via the network 20 may format a data file of the BG data for storage in the non-transitory memory 24, 114, 144 at block 1816. The glucometer 124 may sync the BG data with a mobile device, such as the smart phone 110*b*, to wirelessly transmit the BG data to the web-based application 198 at block 1814. The computing devices 132, 142 of the dosing controller 160 may retrieve the exported BD data file for calculating a next recommended insulin dose and a new value for the Correction Factor (CF) for the patient 10 at entry point Q. The next recommended insulin doses for adjusting the basal and the CF may be input to entry point Q using a basal adjustment process 2300 (FIG. 8), while recommended insulin doses for meal boluses may be input to entry point Q using a meal bolus adjustment process 2400 (FIG. 9). In some examples, the glucometer 124 is configured to connect to the network 20 and transmit the blood glucose data directly to the manufacturer's web-based application 198. In other examples, the glucometer 124 syncs with the smart phone or other mobile device 110*b* to connect to the network 20 and transmit the blood glucose data to the manufacturer's web-based application 198. In some examples, the glucometer 124 syncs with the smart insulin pump 123*a* or smart insulin pen 123*b* to connect to the network 20 and transmit the blood glucose data to the manufacturer's web-based application 198. The smart insulin pump 123*a* or smart insulin pen 123*b* including administration computing devices 112*d* or 112*e* configured to communicate the BG data to the dosing controller 160 and execute the SubQ outpatient program 200 transmitted from the dosing controller 160 causing a doser 223*a*, 223*b* to administer recommended insulin doses specified by the SubQ outpatient program 200.

The SubQ outpatient process 1800*a*, 1800*b* transmits via the network 20 the next recommended insulin dose and the new value for the CF for the patient 10 calculated at 1816 to the web-based application 198 of the meter manufacturer at block 1818, wherein the web-based application 198 of the meter manufacturer formats the next recommended insulin dose and the new value for the CF for the glucometer 124 to receive via the network 20. In some examples, the web-based application 198 transmits the next recommended dose and the new value for the CF to a mobile device, such as the smart phone 110*b*, via the network 20 the mobile device 110*b* syncs with the glucometer 124 (and/or smart pen 123*b*) to provide the next recommended dose and the new value for the CF to the glucometer 124 (and/or the smart pen 123*b*). For instance, the number of insulin units associated with the recommended dose may be automatically measured by the smart pen 123*b* or smart pump 123*a*. Next, the SubQ outpatient process 1800 displays the next recommended insulin dose for the breakfast meal bolus on a Meter Screen via display 116*c* at block 1820.

After the patient self-administers the insulin dose (or the dosing controller 160 executing the SubQ outpatient process 1800*a*, 1800*b* causes the doser 223*a*, 223*b* to administer the insulin dose), at block 1824, the process 1800*a*, 1800*b* determines that the patient 10 has selected a "Dose Entry" to record the administered dose. The SubQ outpatient Process 1800*a*, 1800*b* then prompts the patient 10 to select the insulin dose type on a Meter Screen via display 116*c* at block 1826. The Meter Screen permits the patient to simultaneously select "Correction" and "Meal Bolus" for when the patient 10 has administered a combined dose that the patient 10 would like to record. The selection of "Basal" may not be selected simultaneously with another selection but is operative to cancel out other selections. In response to the patient's 10 selection, the SubQ outpatient process 1800*a*, 1800*b*, at block 1828, presents an insulin drop down menu of populated insulin doses on a Meter Screen via the display 116*c*. Here, the patient 10 may select the number of units of insulin recently administered by the patient 10.

In some implementations, as shown in FIG. 1C, when the patient 10 uses the smart pen 123*b* (or smart pump 123*a*), the SubQ outpatient process 1800 transmits via the network 20 the next recommended insulin dose and the new value for the CF for the patient 10 calculated at entry point Q directly to the smart pen 123*b*, wherein the smart pen 123*b* automatically dials in the recommended dose of insulin without manual input by the patient 10 and may display the dose via the smart pen 123*b* display 116*e*. In other implementations, the smart pen 123*b* syncs (e.g., Bluetooth connection) with the glucometer 124 to receive and automatically dial-in the recommended dose of insulin. In some examples, after the patient 10 administers the insulin dose, the smart pen 123*b* records the number of units of insulin administered by the patient which may be stored in the non-transitory memory 24,114, 144 via the network 20.

Figure 6A:
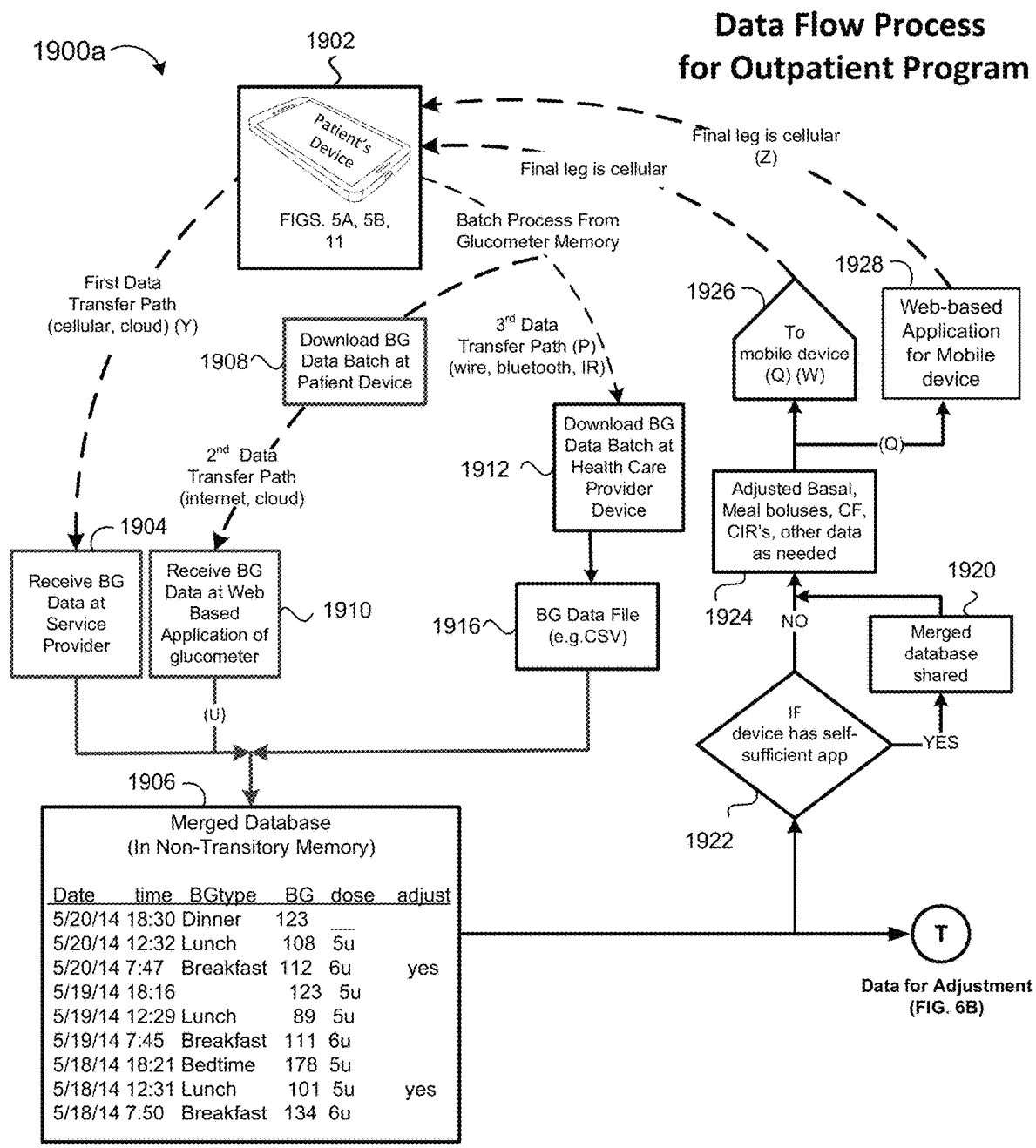
FIG. 6A shows a data transfer process for communicating blood glucose data measured by a patient's glucometer.

FIG. 6A shows a data flow process 1900*a* for storing blood glucose BG data from a patient's mobile device 110*a*, 110*b*, 124, 123*a*, 123*b* within the non-transitory memory 24, 134, 144 in communication with the computing device 112, 132, 142 of the dosing controller 160. The BG data may include, but is not limited to, doses of insulin administered to the patient 10, a blood glucose measurement BG, an associated BGtype, and an associated time of the blood glucose measurement BGtime, as described above with reference to block 1806 of the SubQ outpatient process 1800*a*, 1800*b*. In some implementations, the glucometer 124 syncs with the patient's mobile device 110*a*, 110*b*, 124, 123*a*, 123*b* to transfer the BG data at block 1902. In the example shown, the mobile device is the smart phone 110*b*. The data flow process 1900*a* permits the mobile device 110*b* to transmit the BG data for storage in the non-transitory memory 24, 134, 144 by using one of three data transfer paths.

In some implementations, the data flow process 1900*a* sends the BG data in real-time via a first data transfer path from the mobile device 110*b* at block 1902. The first data transfer path may always be available provided the mobile device 110*b* is able to connect to the network 20 or cellular service. In some scenarios, the data flow process 1900*a*, at block 1902, sends the BG data in real-time via the first data transfer path from the mobile device 110*b* to the computing device 192 of the service provider 130. Thereafter, the data flow process 1900*a* transmits the BG data from the first data transfer path, at block 1904, to a merged database within the non-transitory memory 24, 134, 144 at block 1906.

In other implementations, the data flow process 1900*a* executes a batch process for downloading the BG data from the memory 114*c* of the glucometer 124 at the patient device 110*a* or other computing device connecting to the network 20 at block 1908, and then, transmits the BG data from the patient device 110*a* via a second data transfer path to a web-based application 198 of the manufacturer of the glucometer 124 at block 1910. In some examples, the batch process downloads all BG data stored on the memory 114*c* of the glucometer 124 for a configurable time period. In other examples, the batch process downloads all BG data stored on the memory 114*c* of the glucometer 124 since an immediately previous download session. The web-based application 198 may format a data file (e.g., merged database) of the BG data for storage in the non-transitory memory 24, 114, 144 at block 1906.

In other implementations, the data flow process 1900*a* executes a batch process for downloading the BG data from the memory 114*c* of the glucometer 124 at the health care provider computing device 142 via a third data transfer path at block 1912. For instance, the patient 10 or health care professional 40 may connect the glucometer 124 to the computing device 142 when the patient 10 visits a clinic 42 associated with a hospital call center during a regular check-up. In some examples, the computing device 142 executes a proprietary download program 196 provided by the manufacturer of the glucometer 124 to download the BG data from the memory 114*c* of the glucometer 124. The BG data transfer may be facilitated by connecting the glucometer 124 to the computing device 142 using Bluetooth, Infrared, near field communication (NFC), USB, or serial cable, depending upon the configuration of the glucometer 124. In some examples, the BG data downloaded at block 1912 may be displayed via display 146 for the health care professional to view. The data flow process 1900*a* receives a user 40 input to load the downloaded BG data (e.g., via a button on display 146), and exports the BG data downloaded by the proprietary download program 198 as a formatted BG data file for storage within the non-transitory 24, 114, 144 at block 1916. For example, the exported BG data file may be a CVS file or JSON file. In some examples, the batch process downloads all BG data stored on the memory 114*c* of the glucometer 124 for a configurable time period. In other examples, the batch process downloads all BG data stored on the memory 114*c* of the glucometer 124 since an immediately previous download session during a previous clinic visit by the patient 10.

In some examples, the non-transitory memory 24, 114, 144 includes a database for storing the BG data of the patient 10 received from any one of the first, second, or third data transfer paths. The database may store the BG data in a designated file associated with the patient 10 and identifiable with a patient identifier associated with the patient 10. The BG data within the database of the non-transitory memory 24, 114, 144 may be retrieved by the dosing controller 160 for determining or adjusting doses of insulin for the patient 10 to administer. Block 1906 may send the data within the merged database to Entry point T for routing to other processes, including a Time Limits of Data for Adjustment process (FIG. 6B).

Moreover, block 1906 may provide the data within the merged database to the patient's mobile device 110a, 110b, 124, 123a, 123b at block 1902. For instance, block 1922 may determine if the mobile device includes a self-sufficient application capable of sharing the merged database. If block 1922 is a "YES" indicating that the mobile device includes the self-sufficient application, block 1920 provides the merged database to block 1924 for sharing with the mobile device. Thereafter, block 1924 may provide an adjusted basal dose (from process 2300 of FIG. 8), an adjusted meal dose (from process 2400 of FIG. 9), a correction factor, and/or a carbohydrate-to-insulin ratio CIR (from process 2500 of FIG. 10) over the network 20 directly to the mobile device via Entry Point W at block 1926, or through the web-based application for the mobile device via Entry Point Q at block 1928. If block 1922 is a "NO" indicating that the mobile device does not include a self-sufficient application, block 1924 may provide existing basal doses, meal doses, the correction factor, and/or the carbohydrate-to-insulin ratio over the network 20 to the mobile device at block 1902 via one of block 1926 or block 1928.

Figure 6B:
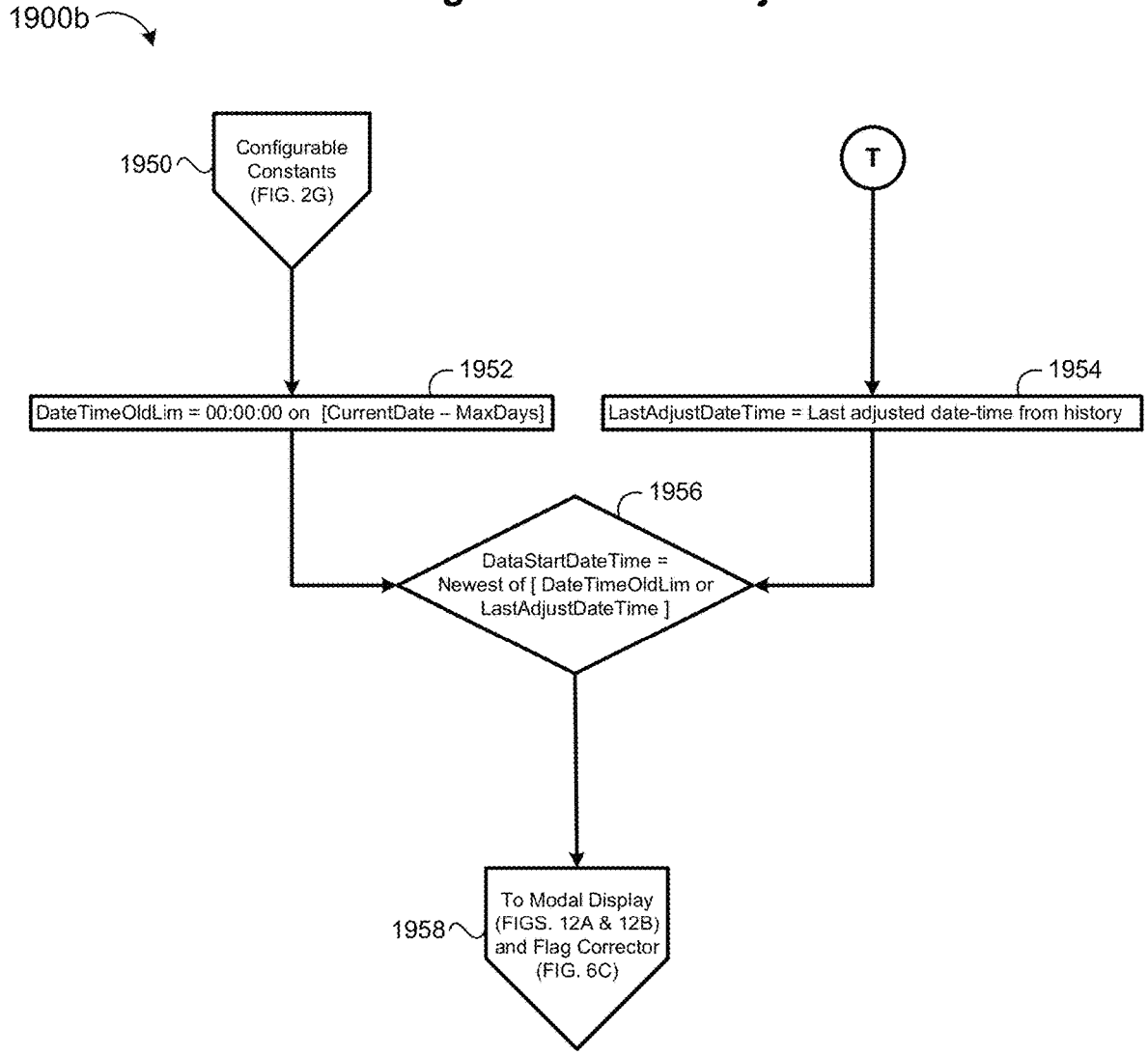
FIG. 6B shows a process for determining an amount of past blood glucose data for use in adjusting dosages of insulin.
Figure 12A:
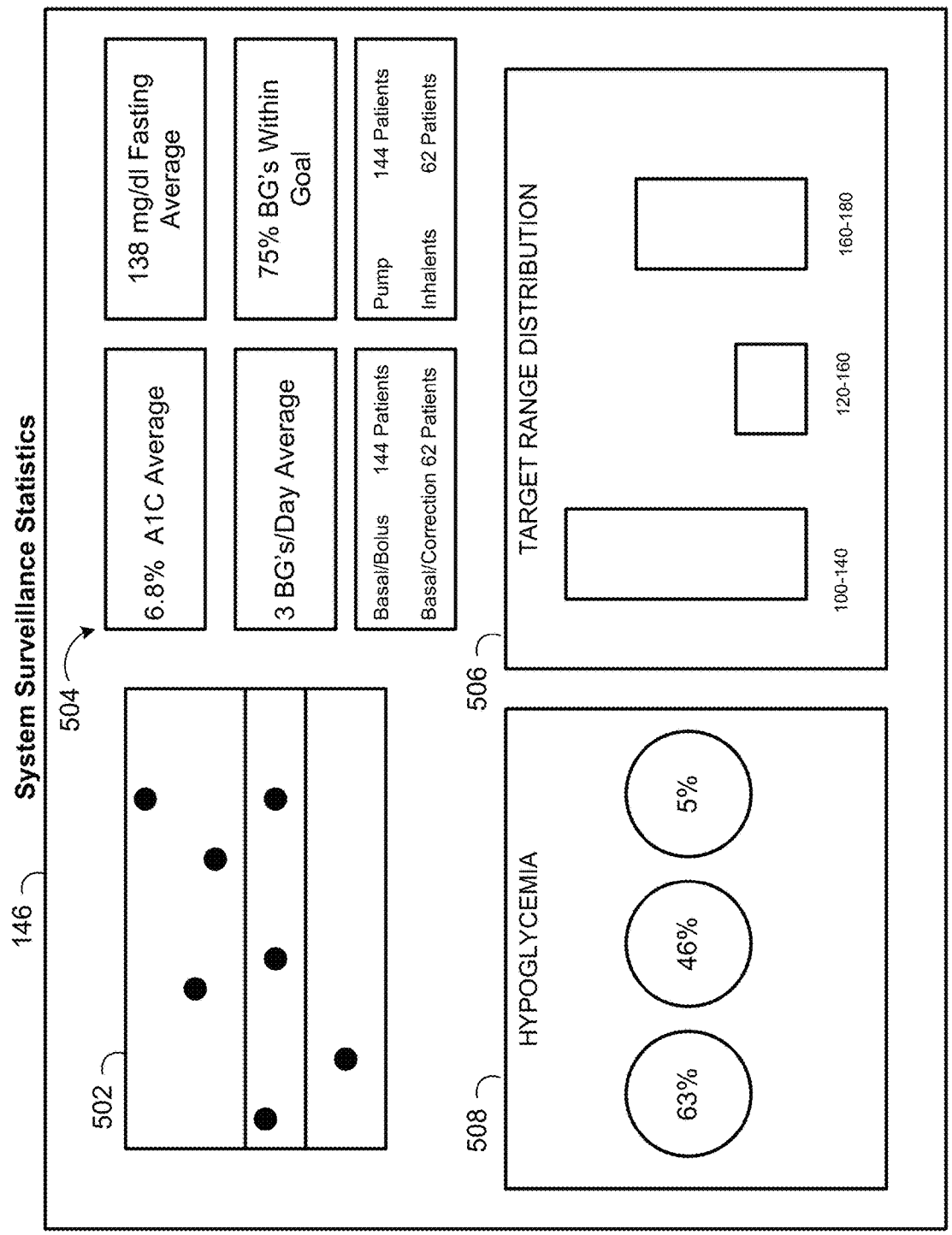
FIG. 12A is a schematic view of an exemplary display for viewing blood glucose data.
Figure 12B:
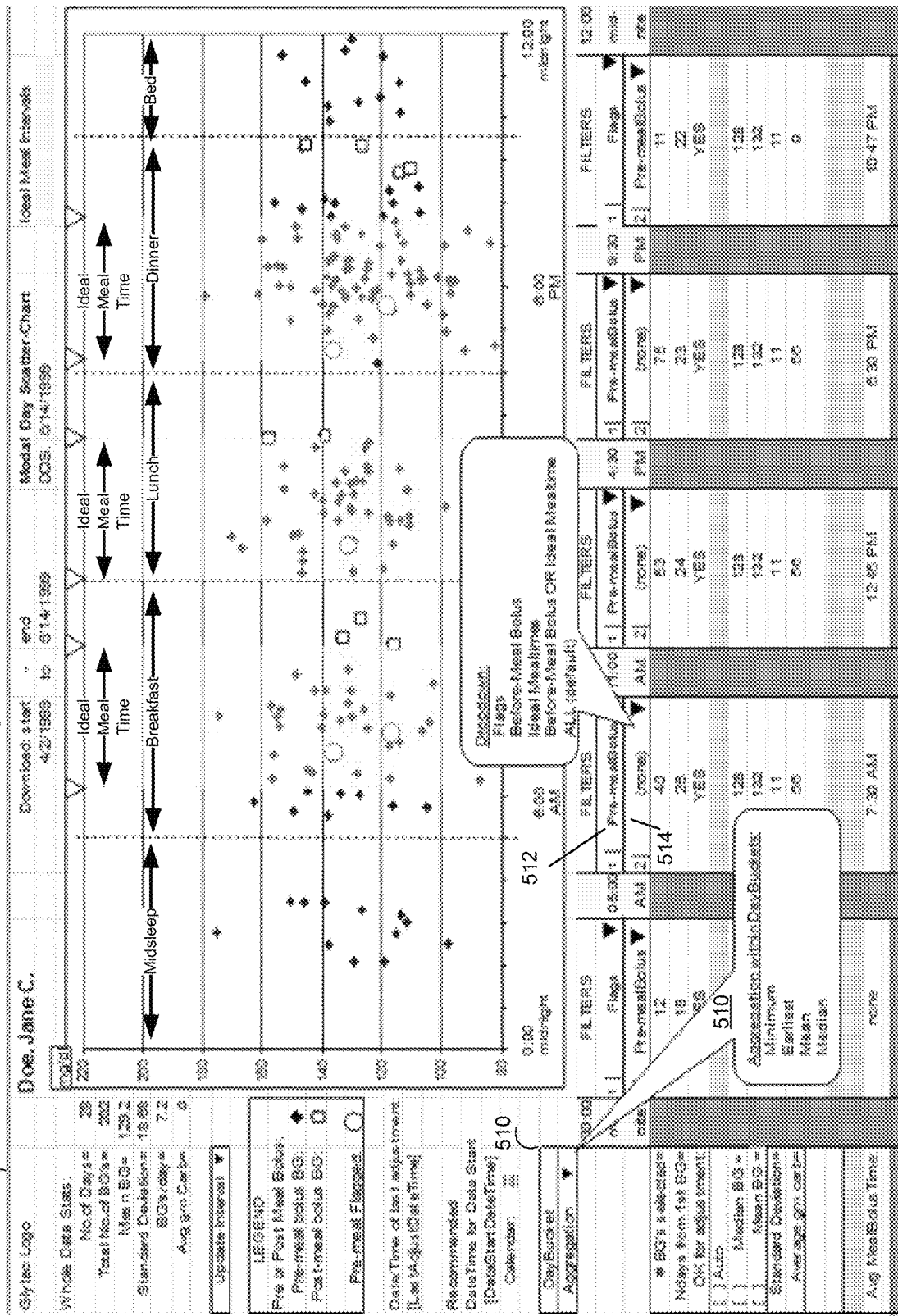
FIG. 12B is a schematic detailed view of an exemplary modal day scatter chart for viewing blood glucose data.

Referring to FIG. 6B, in some implementations, the Limits on Age of Data for Adjustment process 1900b receives the data of Entry Point T from the data flow process 1900a of FIG. 6A. Additionally, process 1900b receives, at block 1950, the configurable constants input at the Healthcare Facility Input Screen 2000 of FIG. 2G, including the constant MaxDays which sets a limit on the amount of data used based on the reasoning that a patient's health can change substantially over several months. The currently configured number for MaxDays is 28 days. Block 1952 shows the oldest allowable date/time (DateTimeOldLim) is midnight (00:00) on the day given by the current date less (minus) the MaxDays. The process 1900b determines, at block 1954, the date/time of the last adjustment (LastAdjustDateTime) from the patient's history from Entry Point T. Thereafter, at block 1956, the process 1900b determines the beginning date/time for the current adjustment (DataStartDateTime) as the most recent date/time between the DateTimeOldLim (block 1952) or the LastAdjustDateTime (block 1954). The process 1900b may then provide the DataStartDateTime to block 1958 for routing to a Flag Corrector process 1900c (FIG. 6C) and to a Modal Day Scatter Chart upon the display 146 (FIGS. 12A and 12B).

Figure 6C:
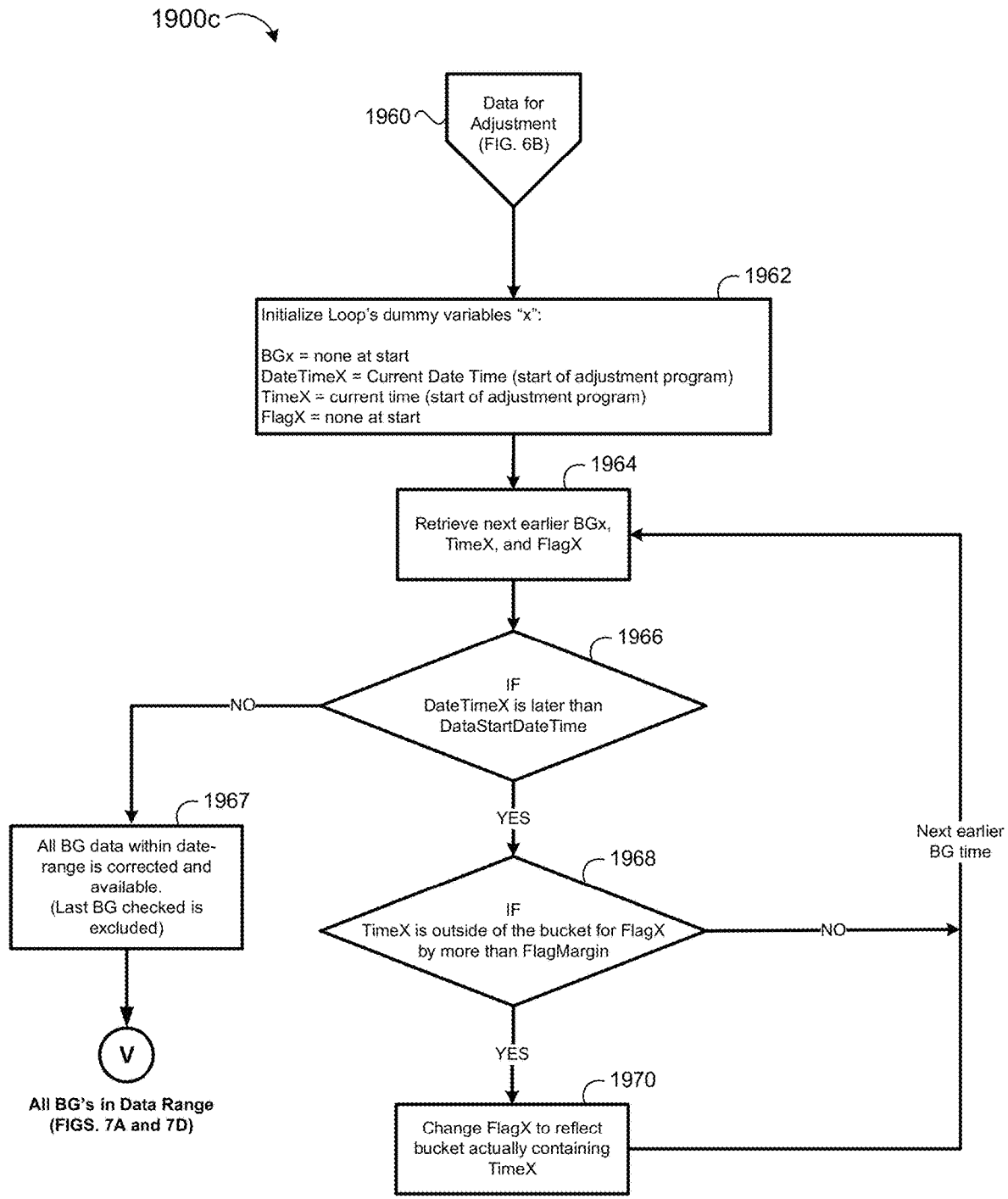
FIG. 6C shows a process for correcting flagged blood glucose measurements to reflect an actual time of the blood glucose measurement.

Blood glucose measurements may be aggregated or flagged according to their associated blood glucose type BGtype or blood glucose time BG time interval to determine a mean or median blood glucose value (EQ. 3) for each BGtype that may be used to determine or adjust recommended doses of insulin (e.g., bolus and/or basal). Referring to FIG. 6C, the Flag Corrector process 1900c receives, at block 1960, the BG data from the process 1900b (FIG. 6B). The glucometer 124 may include a selectable button to flag the BG measurements with a given BGtype (e.g., preBreakfast, pre-Lunch, Bedtime, etc), as shown at the meter screen at block 1804 of FIGS. 5A and 5B (e.g., glucometer display 116d (FIG. 1B)). In some scenarios, patients may infrequently flag BG measurements or may flag the BG measurements incorrectly. In these scenarios, the process 1900c executes a loop to examine all the BG measurements within a specified date range. Prior to executing the loop, the process 1900c, at block 1962, initializes variables for the loop to examine all the blood glucose BG measurements in a date range. The initialized variables may be re-usable dummy variables. Thereafter, the loop starts at block 1964 by retrieving each BG measurement moving backward in time. Block 1966 determines whether the date/time of the analyzed BG measurement is later than the DataStartDateTime. If block 1966 determines that the date/time of the BG measurement is not later than the DataStartDateTime (e.g., block 1966 is "NO"), then the loop stops at block 1967. Here, all the BG measurements in the date-range have now been checked and incorrect flags have been corrected; however, the last BG measurement checked/analyzed was not in the date-range and is therefore excluded from routing to Entry Point V. The process 1900c routes the corrected data through entry point V, whereby the analyzed BG measurements are selected and provided to either the Typical NonMeal Bucket process 2200a (FIG. 7A) or the Typical Meal Bucket process 2200b (FIG. 7D). If, on the other hand, block 1966 determines that the date/time of the BG measurement is not later than the DataStartDateTime (e.g., block 1966 is "YES"), then the analyzed BG measurement is checked at block 1968 to determine whether the BG measurement is outside of the bucket for which it is flagged. For instance, if the time of a BG measurement is outside of a bucket indicated by an associated flag by more than a configurable margin (FlagMargin), then the loop changes the flag to reflect the BGtype indicated by the actual time of the BG measurement. The process 1900c then reverts back to block 1964 and retrieves the next earlier BG measurement in time. The process 1900c ends executing the loop when block 1970 determines a BG is found earlier than the DataStartDateTime, and all the data in the acceptable date-range is provided to Entry Point V for routing to a BG aggregation process 2200 (FIGS. 7A-7F).

If the time of a BG is outside of the bucket indicated by its flag by more than a configurable margin (FlagMargin) then the flag is changed to reflect the BGtype indicated by the actual time of the BG. The loop uses some dummy variables that are re-used, so they are initialized at the start at 2904. The start of the loop at 2906 starts at the present and retrieves each BG moving backward in time. If the date/time of the BG being checked at 2908 is earlier than the DataStartDateTime, then the loop is stopped, if not then the time of the BG is checked at 2912 to see if it is outside the bucket for which it is flagged. If so then the flag is changed at 2914 to indicate the bucket actually inhabited by the BG. The loop ends when a BG is found earlier that the DataStarteDateTime, and all the data in the acceptable date-time range are sent to Entry Point V for use by the BG aggregation processes 2200a, 2200b.

FIGS. 7A-7F show the blood glucose BG aggregation process 2200 for aggregating blood glucose BG measurements for a patient 10 according to the times at which the blood glucose measurements are measured. The aggregation process 2200a, 2200 of FIGS. 7A-7C aggregates BG measurements that are not associated with times when the patient 10 is not consuming meals, while the aggregation process 2200, 2200b of FIGS. 7D-7F aggregates BG measurements associated with times when the patient 10 is consuming meals.

In some examples, the BG measurements are transmitted from the patient's 10 portable device 110a, 110b, 124, 123a, 123b and stored within the non-transitory memory 24, 134, 144. For instance, the BG measurements obtained by the glucometer 124 may be communicated and stored within the non-transitory memory 24, 134, 144 by using the data flow process 1900a, as described above with reference to FIG. 6A. In some implementations, the BG aggregation process 2200 divides a day into five time intervals corresponding to the five BG types: Midsleep, Breakfast, Lunch, Dinner, and Bedtime. As used herein, the term "time buckets" is used to refer to these time intervals corresponding to the five BG types. The Modal Day Scatter Chart 502 of FIG. 12B shows the time buckets as intervals between the dotted lines. Each bucket is associated with a corresponding time boundary that does not overlap the other time boundaries associated with the other buckets.

Referring to FIG. 2H, in some examples, a BG Time-Bucket input screen permits the user 40 (or patient 10) to adjust the time-boundary associated with each time bucket via the display 116, 146. The BG Time-Bucket input screen displays the patient information 208*a* and allows the user 40 to input BG Time-Bucket Information 260 and Ideal Mealtime information 262. For instance, the BG Time-Bucket Information 260 includes a bucket name (e.g., MidSleep, Breakfast, Lunch, Dinner, Bedtime) and associated start and end times for each BG time-bucket. Based upon the BG Time-Bucket Information 260 and the Ideal Mealtime information 262 input to the BG Time-Bucket input screen (FIG. 2H), the BG aggregation process 2200*a* (FIGS. 7A-7C) may associate the BG time-buckets for MidSleep and Bedtime with time intervals when the patient 10 does not consume meals and the BG aggregation process 2200*b* (FIGS. 7D-7F) may associate the BG time-buckets for Breakfast, Lunch and Dinner with time intervals when the patient 10 consumes meals.

Referring back to FIG. 12B, the Modal Day Scatter Chart 502 applies a DayBucket to an interval of time within a time-bucket on a specific day. Thus, each time-bucket may include one or more DayBuckets. The user 40 may select an Aggregation Method (AgMeth) for use within each of the DayBuckets from an Aggregation Menu 510 upon the Modal Day Scatter Chart via the display 146. For example, the user 40 may select an AgMeth from the Aggregation Menu 510 that includes one of Minimum Earliest, Mean, or Median for the BG measurements in the associated DayBucket. Accordingly, the AgMeth selected by the user results in a single value representing the BG measurements associated with the DayBucket. The BG measurements aggregated by the AgMeth may belong to a union of 1 or more subsets denoted by the symbol "U". These values are further aggregated for each BG Bucket over the days in the updated data. The Modal Day Scatter Chart 502 of FIG. 12B shows the aggregation methods available for this aggregation are mean and median and are governed by the variable (MMtype).

Figure 7A:
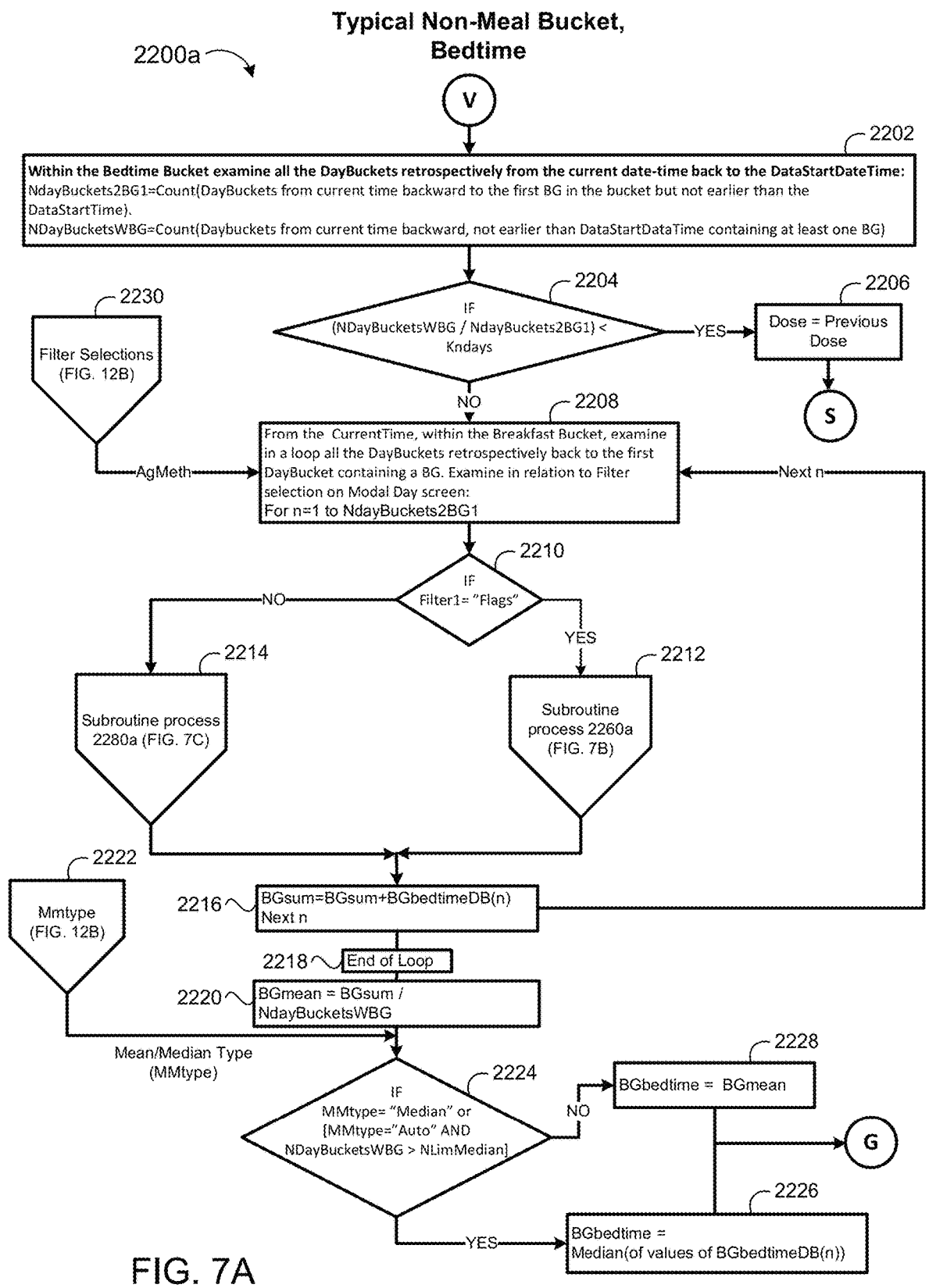
FIGS. 7A-7C are schematic views of a blood glucose aggregation process for time intervals when a patient is not consuming meals.

Referring to FIG. 7A, the BG aggregation process 2200*a* aggregates the BG measurements of the BG time-buckets (e.g., MidSleep and Bedtime) for time intervals when the patient 10 does not consume meals. While FIG. 7A shows the BG aggregation process 2200*a* aggregating BG measurements for the Bedtime BG time-bucket, the BG aggregation process 2200*a* similarly aggregates BG measurements for the Midsleep BG time-bucket. The aggregation process 2200*a* provides the DataStartDataTime (FIG. 6) via Entry Point V to block 2202 for determining a NdaysBedtime (or NdaysMidSleep) that counts the number of DayBuckets within the associated bucket (e.g., Bedtime BG time-bucket) from the current date/time backward to an earliest permissible date/time DataStartDateTime. As used herein, the "earliest date" refers to the earliest one of a previous dosing adjustment or the preconfigured MaxDays (FIG. 6B) into the past. The "earliest date" is operative as a safeguard against a patient returning to the healthcare facility after a year, and receiving a subsequent 365 day adjustment. Additionally, the aggregation process 2200*a* determines, at block 2202, a NDayBucketsWBG that counts the number of the DayBuckets containing at least one BG measurement.

At block 2204, the aggregation process 2200*a* determines a ratio of the DayBuckets containing BG measurements to DayBuckets in the associated bucket (e.g., NDayBucketsWBG/NdaysBedtime) and compares the ratio to a configurable set point (Kndays). The value of Kndays is presently configured at 0.5. If the ratio is less than Kndays, the aggregation process 2200*a* prevents, at block 2206, the dosing controller 160 from adjusting the dose governed by the associated time-bucket (e.g., Bedtime BG time-bucket). For example, when the aggregation process 2200*a* aggregates BG measurements for the Bedtime BG time-bucket, block 2206 prevents the adjustment of the Dinner meal bolus when the ratio of NDayBucketsWBG/NdaysBedtime is less than Kndays indicating that the Bedtime BG time-bucket does not contain enough BG measurements. Block 2206 provides the determination that prevents adjusting the dose governed by the associated time-bucket to Entry Point S for use by processes 2300, 2400, 2500 of FIGS. 8, 9, and 10, respectively. On the other hand, if block 2204 determines that the ratio of NDayBucketsWBG/NdaysBedtime is greater than or equal to Kndays, the dosing controller 160 is permitted to adjust the dose governed by the associated time-bucket.

Figure 7B:
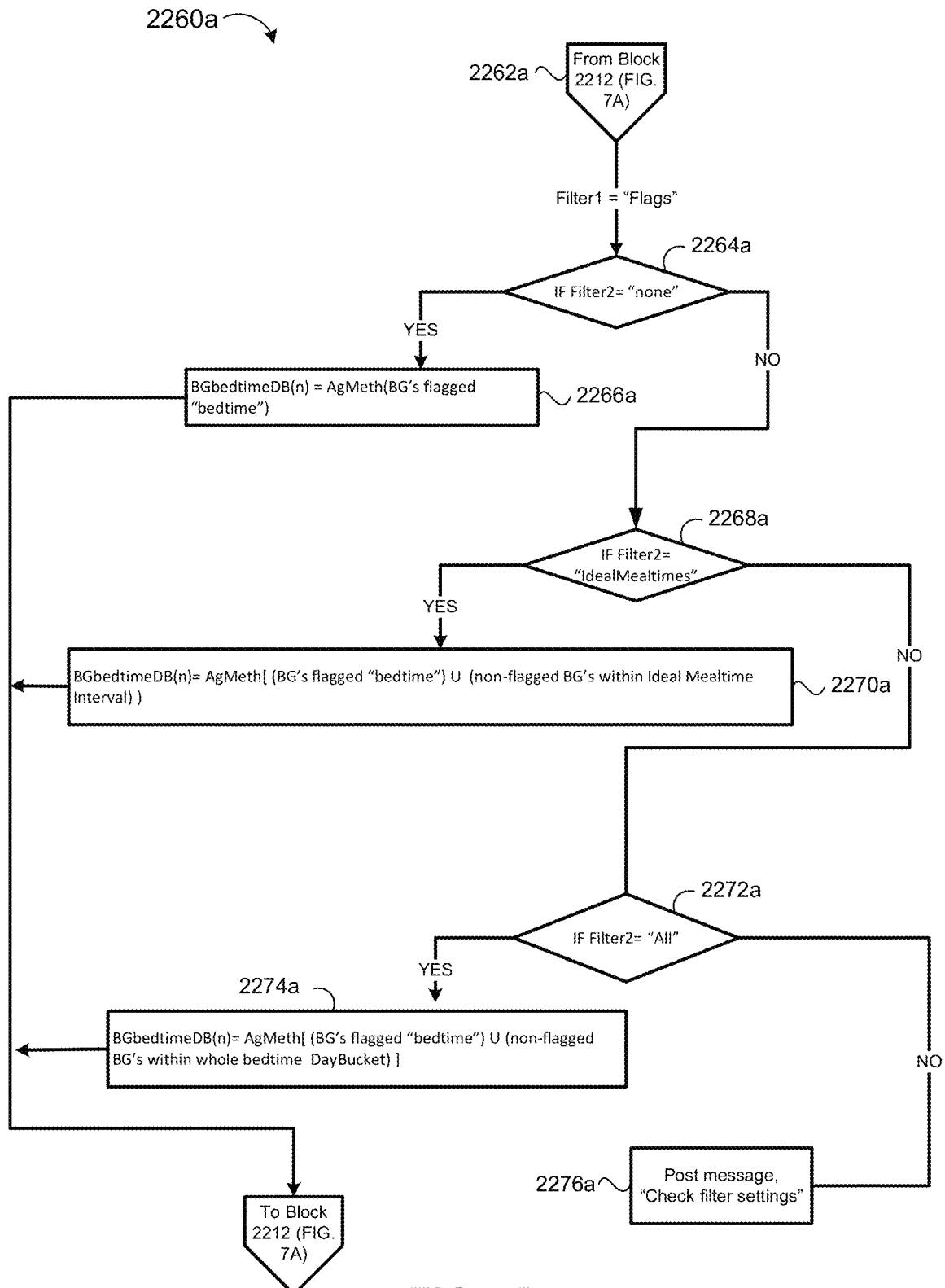

The aggregation process 2200*a* of FIG. 7A and the aggregation process 2200*b* of FIG. 7B use a system of filters to determine the best aggregate BG value to represent the associated time-bucket. There are two dropdown filter selections (Filter1 512 and Filter2 514) that the user 40 may select from the Modal Day Scatter Chart 502 of FIG. 12B. Each of the dropdown filter selections 512, 514 allow the user 40 to select from the following selections:

Flags: Uses the flags entered by the patient 10 on the glucometer 124 at test time and corrected as needed by the Flag Corrector Process 1900*c* (FIG. 6C).

Pre-Meal Bolus: Uses BG Measurements within the bucket that occur earlier than the time of the Meal Bolus (not available for non-meal buckets).

Ideal Meal Time: Shaded areas of the Modal Day Scatter Chart 502 (FIG. 12B) within each associated bucket. Each Ideal Meal Time having boundaries adjustable using drag-and-drop methods by user inputs upon the Modal Day Scatter Chart (FIG. 12B) or via inputs to the Ideal Mealtime information 262 at the BG-time Buckets Input Screen (FIG. 2H).

Both Pre-Meal-bolus OR Ideal Mealtimes: Uses the union of the sets of BG Measurements associated with both the Pre-Meal Bolus and the Ideal Meal Time filters.

All: Uses all the BG measurements within the associated bucket.

None: does not apply a filter.

Figure 7C:
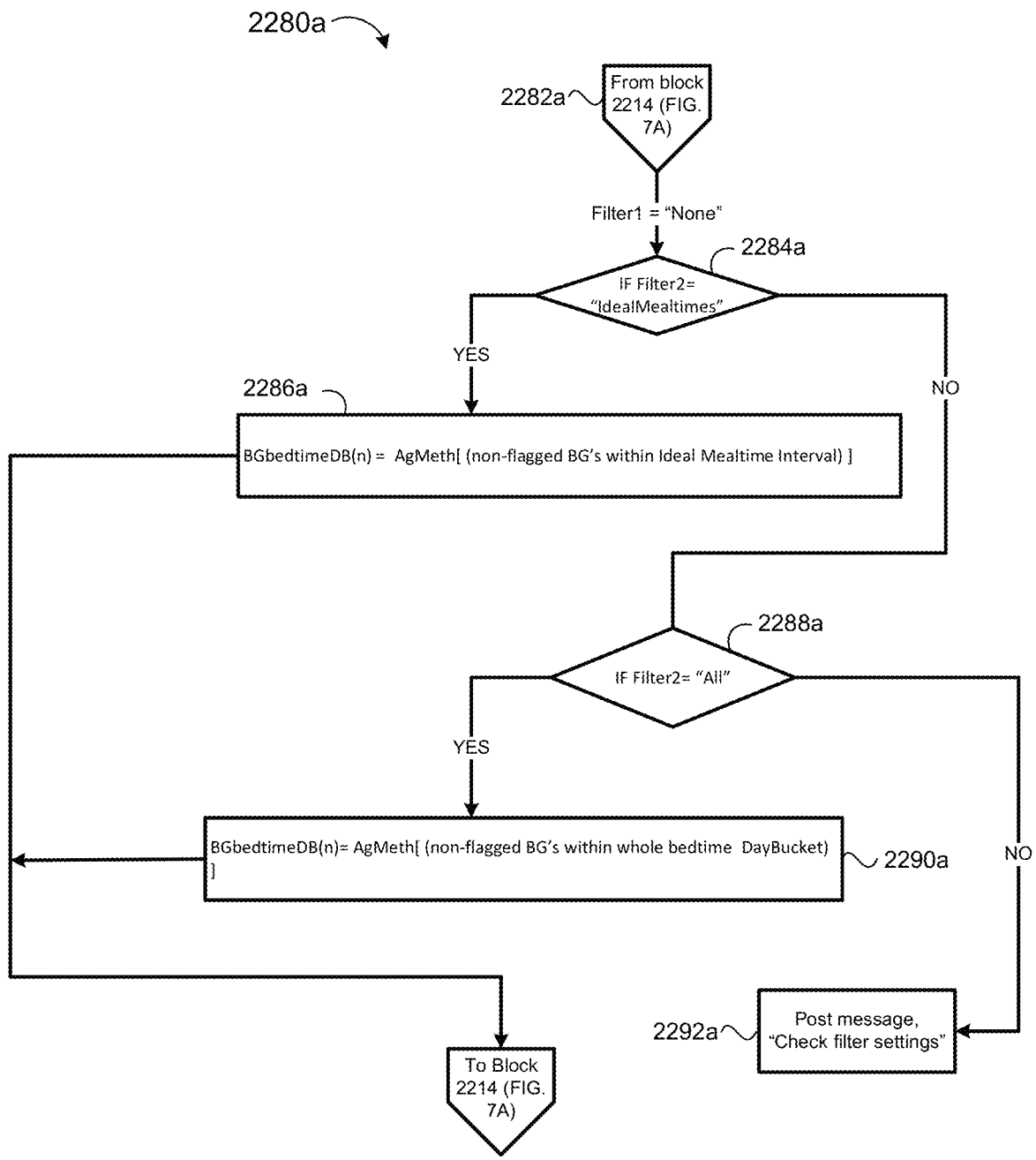
Figure 7D:
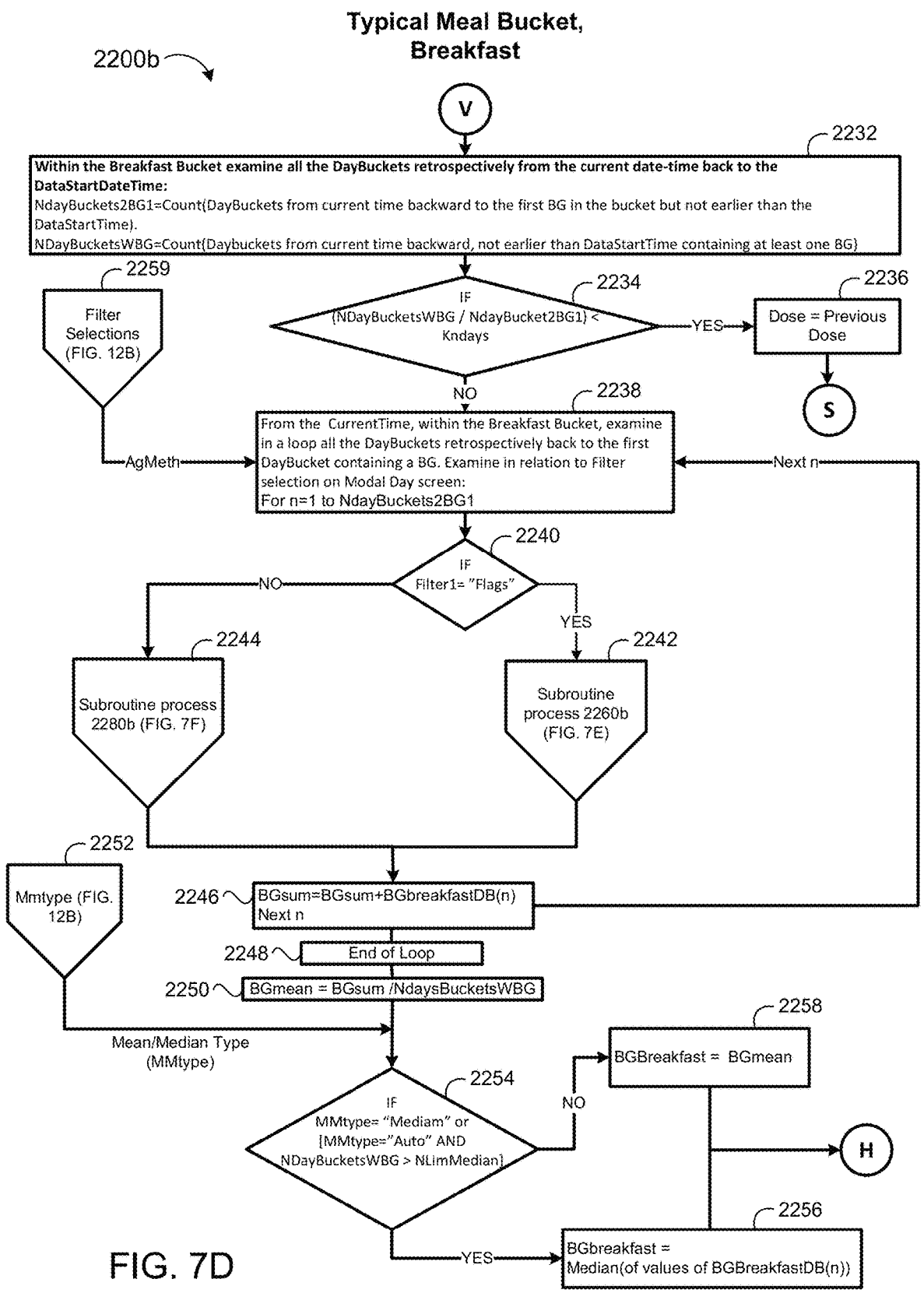
FIGS. 7D-7F are schematic views of a blood glucose aggregation process for time intervals when a patient is consuming meals.

Referring back to FIG. 7A, the aggregation process 2200*a* for the non-meal BG time-buckets (e.g., MidSleep and Bedtime) executes a loop at block 2208 when block 2204 determines that the ratio of NDayBucketsWBG/NdaysBedtime is greater than or equal to Kndays. Specifically, the aggregation process 2200*a* examines, at block 2208, all the DayBuckets in the associated time-bucket (e.g., Bedtime BG time-bucket) back to the DataStartDateTime based on the filter selections 512, 514 of the Modal Day Scatter Chart 502 (FIG. 12B) received via block 2230. At block 2210, the aggregation process 2200*a* examines whether or not Filter1 512 includes "Flags". If the Filter1 512 includes "Flags" (e.g., block 2210 is "YES"), the aggregation process 2200*a* proceeds to block 2212 for executing subroutine process 2260*a* (FIG. 7B). On the other hand, if the Filter1 512 does not include "Flags" (e.g., block 2210 is "NO"), the aggregation process 2200*a* proceeds to block 2214 for executing subroutine process 2280a (FIG. 7C). The two subroutine processes 2260a, 2280a aggregate the BG measurements to a single BG value in each associated DayBucket or none if the associated DayBuckets are empty. The outputs determined by the two subroutine processes 2260a, 2280a are provided back to the aggregation process 2200a (FIG. 7A), and at block 2216, the aggregation process 2200a determines a running sum BGsum of the filtered BG measurements. At block 2218, the loop ends and the aggregation process 2200a determines, at block 2220, a mean of the filtered BG measurements BGmean as the sum of the filtered BG measurements (BGsum) divided by the number of DayBuckets with at least one BG inside, (NdayBucketsWBG). In other configurations, the BGmean may be determined by other methods.

The parameter MMtype is associated with a "mean or median type" that controls a choice of the aggregation method applied to the results of the DayBucket aggregations, i.e. mean or median. The Modal Day Scatter Chart 502 (FIG. 12B) may include a selector for choosing the MMtype input to block 2222 for routing to block 2224 of the aggregation process 2200a. At block 2224, the aggregation process 2200a determines if the NDayBucketsWBG (e.g., the number of filtered BG measurements within the associated time-bucket) is greater than a minimum number of BG measurements required for determining a median value (NLimMedian). If the NDayBucketsWBG is greater than the NLimMedian or if the user 40 manually selects "median" as the MMtype (e.g., block 2224 is "YES"), then the aggregation process 2200a proceeds to block 2226 for calculating the BGbedtime using the median value of NDayBucketsWBG within the time-bucket associated with the Bedtime BG time-bucket. If, however, the NDayBucketsWBG is equal to or less than the NLimMedian (e.g., block 2224 is "NO"), then the aggregation process 2200a proceeds to block 2228 for calculating the BGbedtime using the mean value (BGmean) of NDayBucketsWBG within the time-bucket associated with the Bedtime BG time-bucket. Thereafter, the aggregation process 2200a routes the BGbedtime value (or BGMidsleep value) calculated using the median (block 2226) or the BGmean (block 2228) to Entry Point G for use by processes 2300, 2400, 2500 of FIGS. 8, 9, and 10, respectively.

Referring to FIG. 7B, the subroutine process 2260a executes when the aggregation process 2200a (FIG. 7A) determines that the Filter1 512 includes "Flags" (e.g., block 2210 is "YES"). At block 2262a, the subroutine process 2260a provides the determination that Filter1 512 includes "Flags" from block 2212 of the aggregation process (FIG. 7A) to block 2264a, and block 2264a determines whether or not a filter2 514 applies a filter for the associated time-bucket (e.g., Bedtime BG time-bucket). If filter2 514 is not applying any filters to the Bedtime BG time-bucket (e.g., block 2264a is "YES"), then the subroutine process 2260a sets the BG value in the nth DayBucket, BGbedtimeDB(n) equal to the selected aggregate method AgMeth, at block 2266a to all BG measurements flagged "bedtime" in the DayBucket. The subroutine process 2260a routes BGbedtimeDB(n) back to block 2212 of the aggregation process 2200a (FIG. 7A), where each BG measurement representing a DayBucket "n" BGbedtimeDB(n) within the aggregation process 2200a loop is added to a running sum at block 2216 in preparation for calculating the mean.

If, however, block 2264a determines that filter2 514 is applying a filter to the Bedtime BG time-bucket (e.g., block 2264a is "NO"), then the subroutine process 2260a determines, at block 2268a, whether the selected filter applied by filter2 514 includes the "Ideal Mealtimes" filter. If filter 2 514 is applying the "Ideal Mealtimes" filter (e.g., block 2268a is "YES"), then the subroutine process 2260a sets the BG value in the nth DayBucket, BGbedtimeDB(n) equal to the selected aggregate method AgMeth applied, at block 2270a to the union of all BG measurements flagged "bedtime" in the DayBucket together with all non-flagged BG measurements within the Ideal Mealtimes filter. Thereafter, the subroutine process 2260a routes BGbedtimeDB(n) back to block 2212 of the aggregation process 2200a (FIG. 7A), whereby each BG measurement representing a BGbedtimeDB(n) within the aggregation process 2200a loop is added to a running sum at block 2216 in preparation for calculating the mean.

On the other hand, if filter2 514 is not applying the "Ideal Mealtimes" filter (e.g., block 2268a is "NO"), then the subroutine process 2260a determines, at block 2272a, whether the selected filter applied by filter2 514 includes the "All" filter corresponding to the use of all BG measurements within the associated time-bucket (e.g., Bedtime BG time-bucket). When filter2 514 includes the "All" filter (e.g., block 2272a is "YES"), the subroutine process 2260a sets the BG value in the nth DayBucket, BGbedtimeDB(n) equal to the selected aggregate method AgMeth appliedat block 2274a to the union of all BG measurements flagged "bedtime" in the DayBucket together with all non-flagged BG measurements within the entire Bedtime DayBucket. Thereafter, the subroutine process 2260a routes the BGbedtimeDB(n) back to block 2212 of the aggregation process 2200a (FIG. 7A), whereby each BG measurement(s) representing the BGbedtimeDB(n) within the aggregation process 2200a loop is is added to a running sum at block 2216 in preparation for calculating the mean. The value of BGbedtimeDB(n) routed back to Block 2212 of the aggregation process 2200a from one of blocks 2270a, 2274a fills the nth iteration of the loop. If, however, filter2 514 does not include the "All" filter (e.g., block 2272a is "NO"), then the aggregation process 2200a proceeds to block 2276a and posts message: "Check filter settings" upon the display 116, 146.

Referring to FIG. 7C, the subroutine process 2280a executes when the aggregation process 2200a (FIG. 7A) determines that the Filter1 512 does not include "Flags" (e.g., block 2210 is "NO"). At block 2282a, the subroutine process 2280a provides the determination that Filter1 512 does not include "Flags" from block 2214 of the aggregation process (FIG. 7A) to block 2284a, and block 2284a determines whether or not the selected filter applied by filter2 514 includes the "Ideal Mealtimes" filter. If filter2 514 is applying the "Ideal Mealtimes" filter (e.g., block 2284a is "YES"), then the subroutine process 2280a sets, at block 2286a, the BG value in the nth DayBucket, BGbedtimeDB (n) equal to the selected aggregate method AgMeth applied to all non-flagged BG measurements within the time interval filtered by the Ideal Mealtimes. Thereafter, the subroutine process 2280a routes BGbedtimeDB(n) back to block 2214 of the aggregation process 2200a (FIG. 7A), where each BG measurement representing BGbedtimeDB(n) within the aggregation process 2200a loop is added to a running sum at block 2216 in preparation for calculating the mean.

On the other hand, if filter2 514 is not applying the "Ideal Mealtimes" filter (e.g., block 2284a is "NO"), then the subroutine process 2280a determines, at block 2288a, whether the selected filter applied by filter2 514 includes the "All" filter corresponding to the use of all BG measurements within the associated time-bucket (e.g., Bedtime BG time-bucket). If filter2 514 is applying the "All" filter (e.g., block 2288a is "YES"), then the subroutine process 2280a sets, at block 2290a, the BG value in the nth DayBucket, BGbedtimeDB(n) equal to the selected aggregate method AgMeth applied to all non-flagged BG measurements within the "bedtime" DayBucket. Thereafter, the subroutine process 2280a routes the BGbedtimeDB(n) back to block 2214 of the aggregation process 2200a (FIG. 7A), where each BG measurement(s) representing BGbedtimeDB(n) within the aggregation process 2200a loop is added to a running sum at block 2216 in preparation for calculating the mean. The value routed back to Block 2214 of the aggregation process 2200a from one of blocks 2286a, 2290a fills the nth iteration of the loop. If, however, the filter2 514 is not applying the "All" filter (e.g., block 2288a is "NO"), then at block 2292a, the subroutine process 2280a, posts message: "Check filter settings" upon the display 116, 146.

Referring to FIG. 7D, the BG aggregation process 2200b aggregates the BG measurements of the BG time-buckets (e.g., Breakfast, Lunch, and Dinner) for time intervals when the patient 10 consumes meals. While FIG. 7D shows the BG aggregation process 2200b aggregating BG measurements for the Breakfast time-bucket, the BG aggregation process 2200a similarly aggregates BG measurements for the Lunch and Dinner BG time-buckets. The aggregation process 2200b provides the DataStartDataTime (FIG. 6) via Entry Point V to block 2232 for determining a NdaysBreakfast (or NdaysLunch or NdaysDinner) that counts the number of DayBuckets within the associated bucket (e.g., Breakfast BG time-bucket) from the current date/time backward to an earliest permissible date/time DataStartDateTime. Additionally, the aggregation process 2200b determines, at block 2232, an NDayBucketsWBG that counts the number of the DayBuckets containing at least one BG measurement.

At block 2234, the aggregation process 2200b determines a ratio of the DayBuckets containing BG measurements to DayBuckets in the associated bucket (e.g., NDayBucketsWBG/NdaysBreakfast) and compares the ratio to a configurable set point (Kndays). The value of Kndays is presently configured at 0.5. If the ratio is less than Kndays, the aggregation process 2200b prevents, at block 2236, the dosing controller 160 from adjusting the dose governed by the associated time-bucket (e.g., Breakfast BG time-bucket). For example, when the aggregation process 2200b aggregates BG measurements for the Breakfast BG time-bucket, block 2236 prevents the adjustment of the basal dose when the ratio of NDayBucketsWBG/NdaysBreakfast is less than Kndays indicating that the Breakfast BG time-bucket does not contain enough BG measurements. With respect to the Lunch BG time-bucket, block 2236 would prevent the adjustment of the Breakfast meal bolus when the ratio of NDayBucketsWBG/NdaysLunch is less than Kndays. Similarly, when the ratio of NDayBucketsWBG/NdaysDinner is less than Kndays, block 2236 would prevent the adjustment of the Lunch meal bolus. Block 2236 provides the determination that prevents adjusting the dose governed by the associated time-bucket to Entry Point S for use by processes 2300, 2400, 2500 of FIGS. 8, 9, and 10, respectively. On the other hand, if block 2234 determines that the ratio of NDayBucketsWBG/NdaysBreakfast is greater than or equal to Kndays, the dosing controller 160 is permitted to adjust the dose governed by the associated time-bucket.

Figure 7E:
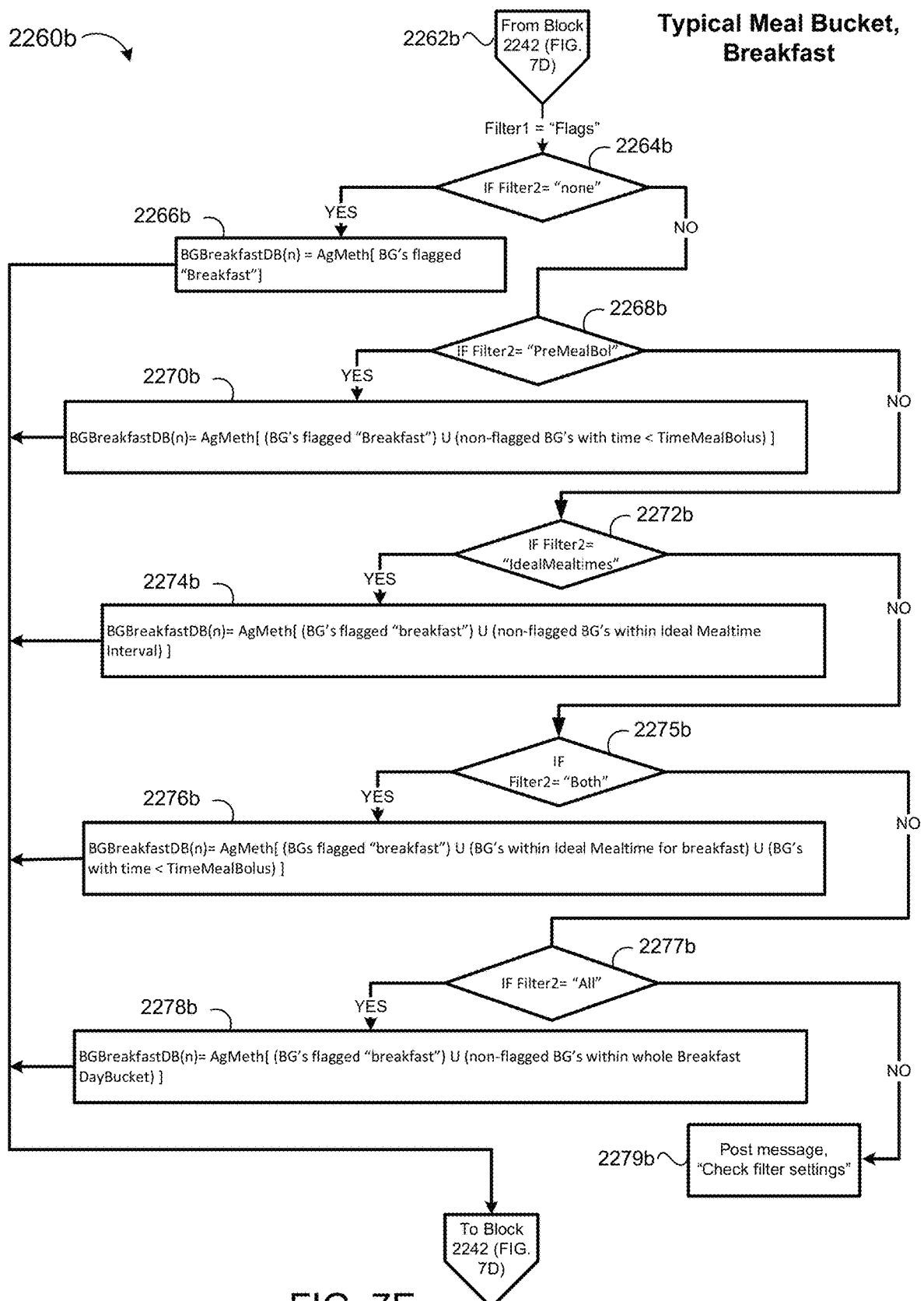
Figure 7F:
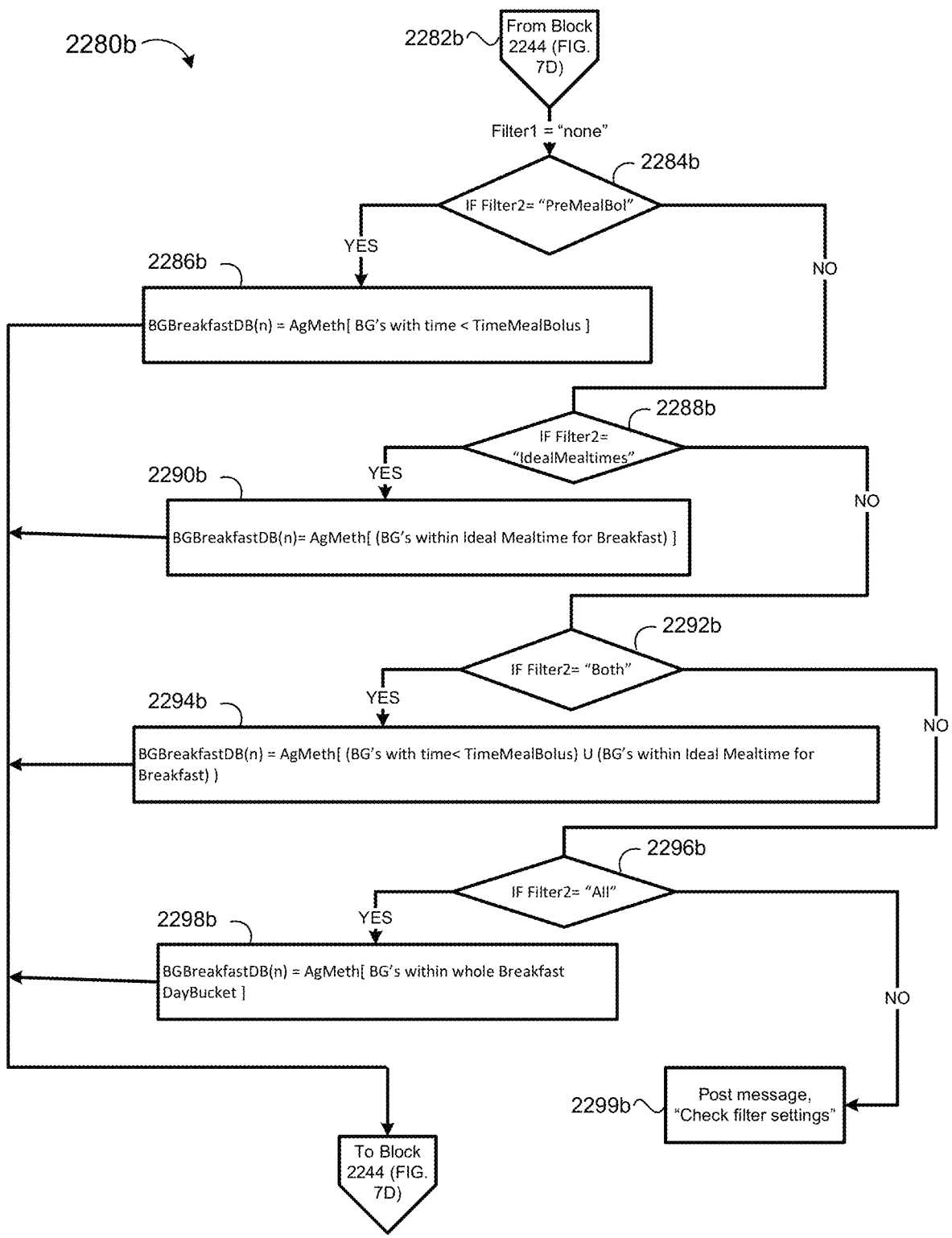

The aggregation process 2200b for the meal BG time-buckets (e.g., Breakfast, Lunch, and Dinner) executes a loop at block 2238 when block 2234 determines that the ratio of NDayBucketsWBG/NdaysBreakfast is greater than or equal to Kndays. Specifically, the aggregation process 2200b examines, at block 2238, all the DayBuckets in the associated time-bucket (e.g., Breakfast BG time-bucket) back to the DataStartDateTime based on the filter selections 512, 514 of the Modal Day Scatter Chart (FIG. 12B) received via block 2259. At block 2240, the aggregation process 2200b examines whether or not Filter1 512 includes "Flags". If the Filter1 512 includes "Flags" (e.g., block 2240 is "YES"), the aggregation process 2200b proceeds to block 2242 for executing subroutine process 2260b (FIG. 7E). On the other hand, if the Filter1 512 does not include "Flags" (e.g., block 2240 is "NO"), the aggregation process 2200b proceeds to block 2244 for executing subroutine process 2280b (FIG. 7F). The two subroutine processes 2260b, 2280b aggregate the BG measurements to a single BG value in each associated DayBucket or none if the associated DayBuckets are empty. The outputs determined by the two subroutine processes 2260b, 2280b are provided back to the aggregation process 2200b (FIG. 7D), and at block 2246, the aggregation process 2200b determines a running sum BGsum of the filtered BG measurements. At block 2248, the loop ends and the aggregation process 2200a determines, at block 2250, a mean of the filtered BG measurements BGmean as the sum of the filtered BG measurements (BGsum) divided by the number of DayBuckets with at least one BG (NdayBucketsWBG). In other configurations, the BGmean may be determined by other methods.

As set forth above in the aggregation process 2200a (FIG. 7A), the parameter MMtype is associated with a "mean or median type" that controls the choice of the aggregation method applied to the results of the DayBucket aggregations, i.e. mean or median. Here, the selector of the Modal Day Scatter Chart 502 (FIG. 12B) chooses the MMtype input to block 2252 for routing to block 2254 of the aggregation process 2200b. At block 2254, the aggregation process 2200b determines if the NDayBucketsWBG (e.g., the number of filtered BG measurements within the associated time-bucket) is greater than a minimum number of BG measurements required for determining a median value (NLimMedian). If the NDayBucketsWBG is greater than the NLimMedian or if the user 40 manually selects "median" as the MMtype (e.g., block 2254 is "YES"), then the aggregation process 2200b proceeds to block 2256 for calculating the BGBreakfast using the median value of NDayBucketsWBG within the time-bucket associated with the Breakfast BG time-bucket. If, however, the NDayBucketsWBG is equal to or less than the NLimMedian (e.g., block 2254 is "NO"), then the aggregation process 2200b proceeds to block 2258 for calculating the BGBreakfast using the mean value (BGmean) of NDayBucketsWBG within the time-bucket associated with the Breakfast BG time-bucket. Thereafter, the aggregation process 2200b routes the BGBreakfast value (or BGLunch or BGDinner values) calculated using the median (block 2256) or the BGmean (block 2258) to Entry Point H for use by processes 2300, 2400, 2500 of FIGS. 8, 9, and 10, respectively.

Referring to FIG. 7E, the subroutine process 2260b executes when the aggregation process 2200b (FIG. 7D) determines that the Filter1 512 includes "Flags" (e.g., block 2240 is "YES"). At block 2262b, the subroutine process 2260b provides the determination that Filter1 512 includes "Flags" from block 2242 of the aggregation process 2200b (FIG. 7D) to block 2264b, and block 2264b determines whether or not a filter2 514 applies a filter for the associated time-bucket (e.g., Breakfast BG time-bucket). If filter2 514 is not applying any filters to the Breakfast BG time-bucket (e.g., block 2264b is "YES"), then the subroutine process 2260b at block 2266b, sets the aggregate value of the BG's in the nth DayBucket of the Breakfast bucket, BGBreakfastDB(n) to the selected aggregate method AgMeth applied to all BG measurements flagged "Breakfast" in the DayBucket. The subroutine process 2260b routes BGBreakfastDB(n) back to block 2242 of the aggregation process 2200b (FIG. 7D), where each BG measurement representing DayBucket "n", BGBreakfastDB(n) within the aggregation process 2200b loop is added at block 2246 to a running sum in preparation for calculating a mean.

If, however, block 2264b determines that filter2 514 is applying a filter to the Breakfast BG time-bucket (e.g., block 2264b is "NO"), then the subroutine process 2260b determines, at block 2268b, whether the selected filter applied by filter 2 514 includes the Pre-Meal Bolus "PreMealBol" filter. If filter 2 514 is applying the "Pre-Meal Bolus" filter (e.g., block 2268b is "YES"), then the subroutine process 2260a at block 2270b, sets the aggregate value of the BG's in the nth DayBucket of the Breakfast bucket, BGBreakfastDB(n) to the selected aggregate method AgMeth applied to the union of the set of BG measurements flagged "breakfast" in the DayBucket together with the set of all non-flagged BG measurements having times earlier than a time of the breakfast meal bolus (TimeMealBolus). Thereafter, the subroutine process 2260b routes BGBreakfastDB(n) back to block 2242 of the aggregation process 2200b (FIG. 7D), where each BG measurement representing BGBreakfastDB(n) within the aggregation process 2200b loop is added at block 2246 to a running sum in preparation for calculation of a mean. When the subroutine process 2260b determines, at block 2268b, that filter2 514 is not applying the Pre-Meal Bolus filter (e.g., block 2268b is "NO"), the subroutine process 2260b proceeds to block 2272b.

At block 2272b, the subroutine process 2260b determines whether the selected filter applied by filter2 514 includes the "Ideal Mealtimes" filter. If filter2 514 is applying the "Ideal Mealtimes" filter (e.g., block 2272b is "YES"), then the subroutine process 2260b at block 2274b, sets BGBreakfastDB(n) to the selected aggregate method AgMeth applied to the union of the set of BG measurements flagged "breakfast" in the DayBucket together with the set of non-flagged BG measurements within the Ideal Mealtimes filter for breakfast. Thereafter, the subroutine process 2260b routes BGBreakfastDB(n) back to block 2242 of the aggregation process 2200b (FIG. 7D), where each BG measurement representing BGBreakfastDB(n) within the aggregation process 2200b loop is added at block 2246 to a running sum in preparation for calculation of a mean.

On the other hand, if filter2 514 is not applying the "Ideal Mealtimes" filter (e.g., block 2272b is "NO"), then the subroutine process 2260b determines, at block 2275b, whether the selected filter applied by filter2 514 includes the "Pre-MealBolus OR IdealMealtime" filter, which passes a union of the sets of BG's that meet the Pre-Meal Bolus filter criteria or Ideal Mealtimes filter criteria. If filter2 514 is applying the "Pre-MealBolus OR IdealMealtime" filter (e.g., block 2275b is "YES"), then the subroutine process 2260b, at block 2276b, sets BGBreakfastDB(n) to the selected aggregate method AgMeth applied to the union of the set of BG measurements flagged "breakfast" in the DayBucket together with the set of all non-flagged BG measurements having times earlier than TimeMealBolus for breakfast together with the set of non-flagged BG measurements within the Ideal Mealtime interval for breakfast. Thereafter, the subroutine process 2260b routes BGBreakfastDB(n) back to block 2242 of the aggregation process 2200b (FIG. 7D), where each BG measurement representing BGBreakfastDB(n) within the aggregation process 2200b loop is added at block 2246 to a running sum in preparation for calculation of a mean. When the subroutine process 2260b determines, at block 2275b, that filter2 514 is not applying the "Pre-MealBolus OR IdealMealtime" filter (e.g., block 2275b is "NO"), the subroutine process 2260b proceeds to block 2277b.

At block 2277b, the subroutine process 2260b determines whether the selected filter applied by filter2 514 includes the "All" filter corresponding to the use of all BG measurements within the associated time-bucket (e.g., Breakfast BG timebucket). At block 2278b, the subroutine process 2260b sets BGBreakfastDB(n) to the the selected aggregate method AGMeth applied to the union of the set of BG measurements flagged "breakfast" in the DayBucket together with the set of all non-flagged BG measurements within the entire Breakfast Daybucket. Thereafter, the subroutine process 2260b routes BGBreakfastDB(n) back to block 2242 of the aggregation process 2200b (FIG. 7D), where each BG measurement representing the BGBreakfastDB(n) within the aggregation process 2200b loop is added at block 2246 to a running sum in preparation to calculation of a mean. The value routed back to Block 2242 of the aggregation process 2200b from one of blocks 2266b, 2270b, 2274b, 2276b, 2278b fills the nth iteration of the loop. If, however, the filter2 514 is not applying the "All" filter (e.g., block 2277b is "NO"), then at block 2279b, the subroutine process 2260b, posts message: "Check filter settings" upon the display 116, 146.

Referring to FIG. 7F, the subroutine process 2280b executes when the aggregation process 2200b (FIG. 7D) determines that the Filter1 512 does not include "Flags" (e.g., block 2240 is "NO"). At block 2282b, the subroutine process 2280b provides the determination that Filter1 512 does not include "Flags" from block 2244 of the aggregation process 2200b (FIG. 7D) to block 2284b, and block 2284b determines whether or not the selected filter applied by filter2 514 includes the "Pre-Meal Bolus" filter. If filter 2 514 is applying the "Pre Meal Bolus" filter (e.g., block 2284b is "YES"), then the subroutine process 2280b, at block 2286b, sets BGBreakfastDB(n) to the selected aggregate method AgMeth applied to all BG measurements having times earlier than the time of the associated breakfast meal bolus (TimeMealBolus). Thereafter, the subroutine process 2280b routes BGBreakfastDB(n) back to block 2244 of the aggregation process 2200b (FIG. 7D), where each BG measurement representing BGBreakfastDB(n) within the aggregation process 2200b loop is added at block 2246 to a running sum in preparation for calculating a mean. When the subroutine process 2260b determines, at block 2284b, that filter2 514 is not applying the Pre Meal Bolus filter (e.g., block 2284b is "NO"), the subroutine process 2280b proceeds to block 2288b.

At block 2288b, the subroutine process 2280b determines whether the selected filter applied by filter2 514 includes the "Ideal Mealtimes" filter. If filter2 514 is applying the "Ideal Mealtimes" filter (e.g., block 2288b is "YES"), then the subroutine process 2280b, at block 2290b, sets BGBreakfastDB(n) to the selected aggregate method AgMeth applied to all BG measurements within the Ideal Mealtimes interval (e.g., ideal time filter) for breakfast. Thereafter, the subroutine process 2280b routes BGBreakfastDB(n) back to block 2244 of the aggregation process 2200b (FIG. 7D), where each BG measurement(s) representing BGBreakfastDB(n) within the aggregation process 2200b loop is added at block 2246 to a running sum in preparation for calculating a mean.

On the other hand, if filter2 514 is not applying the "Ideal Mealtimes" filter (e.g., block 2288b is "NO"), then the subroutine process 2280b determines, at block 2292b, whether the selected filter applied by filter2 514 includes the "Pre-MealBolus OR Ideal Mealtimes" filter, which passes the BG's that pass either the Pre Meal Bolus filter or the Ideal Mealtimes filter. If filter2 514 is applying the "Both" filter (e.g., block 2292b is "YES"), then the subroutine process 2280b, at block 2294b, sets BGBreakfastDB(n) to the selected aggregate method AgMeth applied to the union of the set of all BG measurements having times earlier than TimeMealBolus for breakfast together with the set of all BG measurements within the Ideal Mealtime interval for breakfast. Thereafter, the subroutine process 2280b routes BGBreakfastDB(n) back to block 2244 of the aggregation process 2200b (FIG. 7D), where each BG measurement representing BGBreakfastDB(n) within the aggregation process 2200b loop is added at block 2246 to a running sum in preparation for calculating a mean. When the subroutine process 2280b determines, at block 2292b, that filter2 514 is not applying the "Both" filter (e.g., block 2292b is "NO"), the subroutine process 2280b proceeds to block 2296b.

At block 2296b, the subroutine process 2280b determines whether the selected filter applied by filter2 514 includes the "All" filter corresponding to the use of all BG measurements within the associated time-bucket (e.g., Breakfast BG time-bucket). At block 2298b, the subroutine process 2280b sets BGBreakfastDB(n) to the selected aggregate method AGMeth applied to all BG measurements within the entire Breakfast DayBucket. Thereafter, the subroutine process 2280b routes BGBreakfastDB(n) back to block 2244 of the aggregation process 2200b (FIG. 7D), where each BG measurement representing the BGBreakfastDB(n) within the aggregation process 2200b loop is added at block 2246 to a running sum in preparation for calculating a mean. The value routed back to Block 2244 of the aggregation process 2200b from one of blocks 2286b, 2290b, 2294b, 2298b fills the nth iteration of the loop. If, however, the filter2 514 is not applying the "All" filter (e.g., block 2296b is "NO"), then at block 2299b, the subroutine process 2280b, posts message: "Check filter settings" upon the display 116, 146.

Figure 8:
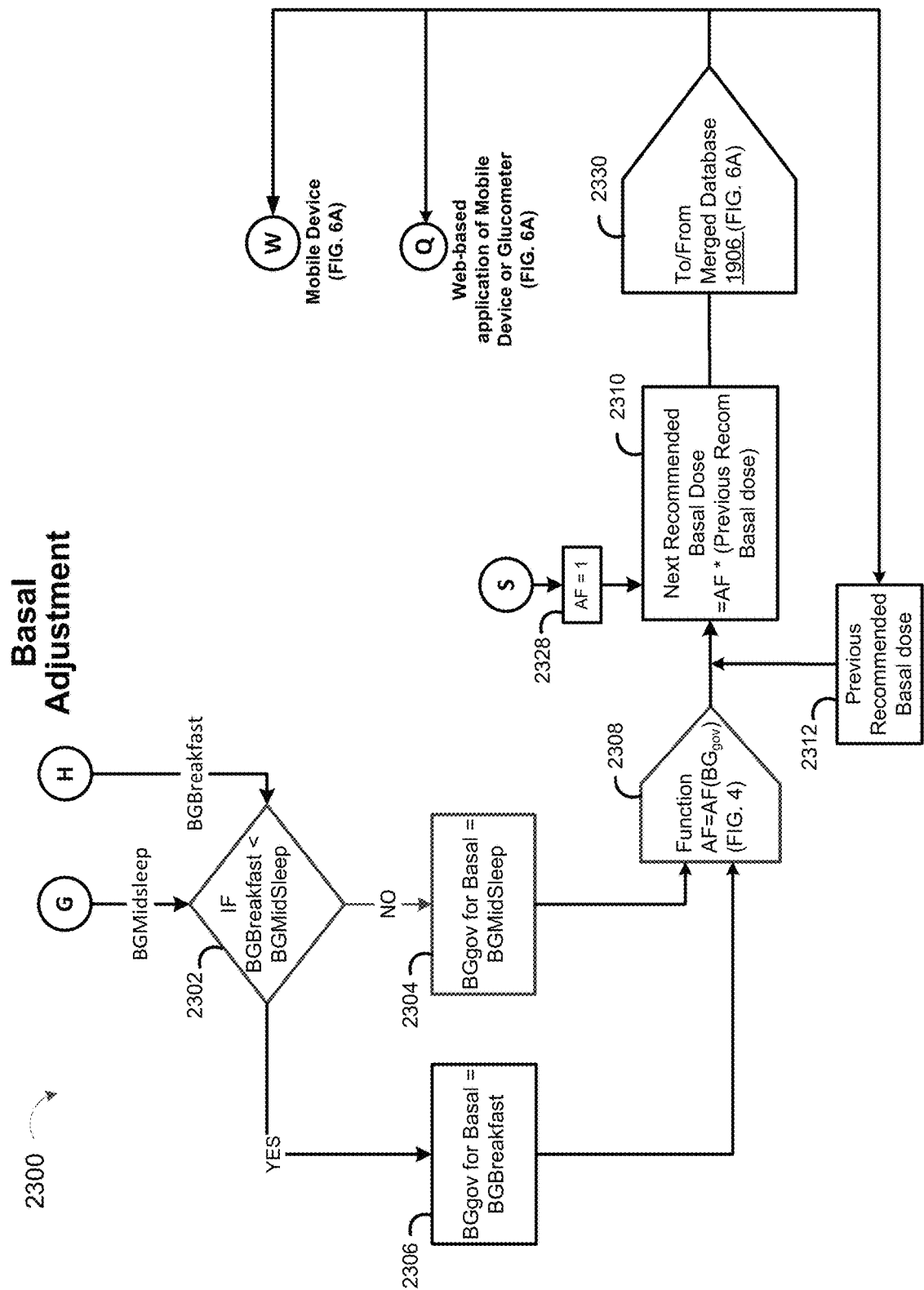
FIG. 8 is a schematic view of an exemplary basal adjustment process
Figure 9:
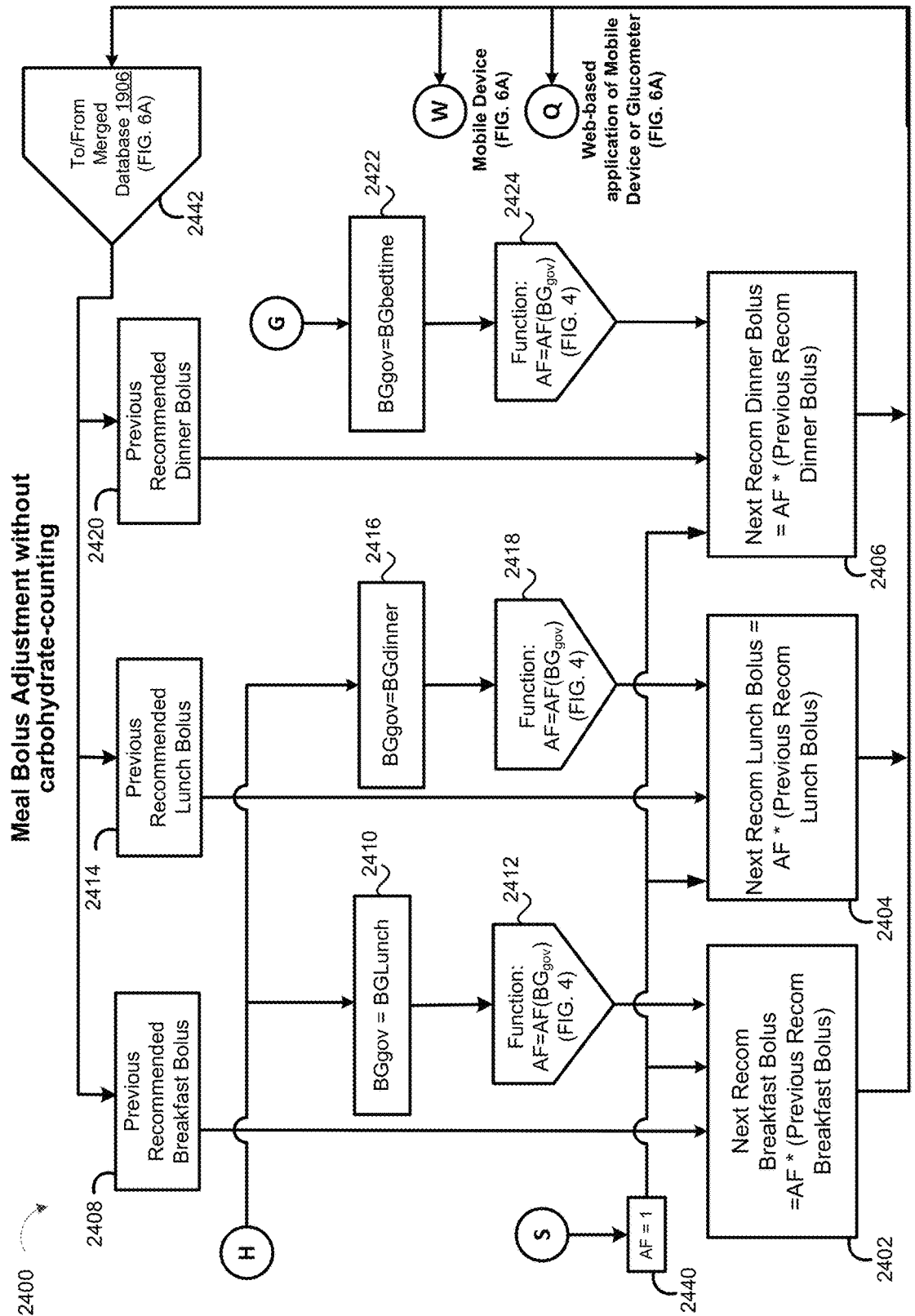
FIG. 9 is a schematic view of an exemplary meal bolus adjustment process.

FIG. 8 shows a basal adjustment process 2300 where block 2302 receives the BGBreakfast from Entry Point H (FIG. 7D) and the BGmidsleep (or from Entry Point G (FIG. 7A). In some implementations, process 2300 determines whether or not the BGBreakfast is less than BGmidsleep. The basal adjustment process 2300, at block 2304, selects the BGbreakfast as the governing blood glucose BGgov for a basal adjustment when BG breakfast is not less than BGmidsleep, and block 2306 selects the BGmidsleep as the governing blood glucose BGgov for the basal adjustment when BG breakfast is less than BGmidsleep. The basal adjustment process 2300 applies an adjustment factor (AF) function (FIG. 4) at block 2308 using the BGgov selected from one of blocks 2304 or 2306. Specifically, the basal adjustment process 2300 determines the adjustment factor AF at block 2308 as a function of the governing blood glucose BGgov. In scenarios when there are an insufficient number of BG measurements for the Midsleep BG time-bucket, i.e., when block 2204 (FIG. 7A) of aggregation processes 2200a is "YES", the basal adjustment process 2300, sets, at block 2328, the Adjustment Factor AF equal to 1. The basal adjustment process 2300 receives, at block 2328, the indication of insufficient BG data, i.e., preventing adjustment of the governing dose, from processes 2200a via Entry Point S. At block 2310, the basal adjustment process 2300 determines the adjustment to the patient's insulin dose by the following equation:

$$\text{RecomBasal} = (\text{previous RecomBasal}) * AF \quad (12)$$

wherein the previous RecomBasal is provided from block 2312. The basal adjustment process 2300 transmits, at block 2310, the next recommended basal adjustment RecomBasal to the web-based application 198 of the manufacturer of the glucometer 124 or mobile device 110b via Entry Point Q of the SubQ outpatient process 1800 (FIG. 5A or FIG. 5B). In some implementations, the basal adjustment process 2300 uses the data flow process 1900a (FIG. 6A) to transmit the next recommended basal adjustment RecomBasal directly to the mobile device 110b via Entry Point W (FIG. 6A). In other implementations, the basal adjustment process 2300 uses the data flow process 1900a (FIG. 6A) to transmit the next recommended basal adjustment RecomBasal to the web-based application 198 of the mobile device 110b or the glucometer 124 via Entry Point Q (FIG. 6A). Additionally, the basal adjustment process 2300 provides, at block 2330, the RecomBasal to the merged database 1906 (FIG. 6A) within the non-transitory memory 24, 134, 144.

Referring to FIG. 9, a meal bolus adjustment (without carbohydrate-counting) process 2400 shows blocks 2402, 2404, 2406 calculating next recommended meal boluses for scheduled meal boluses of breakfast, lunch, and dinner, respectively. The next recommended meal bolus for each scheduled meal bolus is based on the blood glucose BG measurement that occurs after the meal bolus being adjusted.

For calculating the next recommended breakfast bolus (block 2402), the meal bolus adjustment process 2400 receives, at block 2410, the BG measurement (e.g., BGlunch) that occurs after the breakfast meal bolus via Entry Point H of the aggregation process 2200b (FIG. 7D), and sets the BGlunch as a governing blood glucose BGgov. The meal bolus adjustment process 2400 applies an adjustment factor (AF) function (FIG. 4) at block 2412 using BGlunch as the BGgov. Specifically, the meal bolus adjustment process 2400 determines the adjustment factor AF at block 2412 as function of the governing blood glucose BGgov (e.g., BGlunch). In scenarios when there are an insufficient number of BG measurements for the Lunch BG time-bucket, i.e., when block 2234 (FIG. 7D) of aggregation processes 2200b is "YES", the meal adjustment process 2400, sets, at block 2440, the Adjustment Factor AF equal to 1. The meal bolus adjustment process 2400 receives, at block 2440, the indication of insufficient BG data, i.e., preventing adjustment of the governing dose, from the aggregation process 2200b via Entry Point S. At block 2402, the meal bolus adjustment process 2400 determines the adjustment to the patient's breakfast meal bolus by the following equation:

$$\text{RecomBreakBol} = (\text{previous RecomBreakBol}) * AF \quad (15A)$$

wherein the previous RecomBreakBol is provided from block 2408. Block 2408 may obtain the previous RecomBreakBol from block 2442 associated with the merged database 1906 (FIG. 6A) within the non-transitory memory 24, 134, 144. Thereafter, the meal bolus adjustment process 2400 uses the data flow process 1900a (FIG. 6A) to transmit the next recommended breakfast bolus to the web-based application 198 of the mobile device 110b or the glucometer 124 via Entry Point Q (FIG. 6A), or directly to the mobile device 110b via Entry Point W (FIG. 6A).

For calculating the next recommended lunch bolus (block 2404), the meal bolus adjustment process 2400 receives, at block 2416, the BG measurement (e.g., BGdinner) that occurs after the lunch meal bolus via Entry Point H of the aggregation process 2200b (FIG. 7D), and sets the BGdinner as a governing blood glucose BGgov. The meal bolus adjustment process 2400 applies an adjustment factor (AF) function (FIG. 4) at block 2418 using BGdinner as the BGgov. Specifically, the meal bolus adjustment process 2400 determines the adjustment factor AF at block 2418 as a function of the governing blood glucose BGgov (e.g., BGdinner). In scenarios when there are an insufficient number of BG measurements for the Dinner BG time-bucket, i.e., when block 2234 (FIG. 7D) of aggregation processes 2200b is "YES", the meal adjustment process 2400, sets, at block 2440, the Adjustment Factor AF equal to 1. The meal bolus adjustment process 2400 receives, at block 2440, the indication of insufficient BG data, i.e., preventing adjustment of the governing dose, from the aggregation process 2200b via Entry Point S. At block 2404, the meal bolus adjustment process 2400 determines the adjustment to the patient's lunch meal bolus by the following equation:

$$\text{RecomLunchBol} = (\text{previous RecomLunchBol}) * AF \qquad (15\text{B})$$

wherein the previous RecomLunchBol is provided from block 2414. Block 2414 may obtain the previous RecomLunchBol from block 2442 associated with the merged database 1906 (FIG. 6A) within the non-transitory memory 24, 134, 144. Thereafter, the meal bolus adjustment process 2400 uses the data flow process 1900a (FIG. 6A) to transmit the next recommended lunch bolus to the web-based application 198 of the mobile device 110b or the glucometer 124 via Entry Point Q (FIG. 6A), or directly to the mobile device 110b via Entry Point W (FIG. 6A).

For calculating the next recommended dinner bolus (block 2406), the meal bolus adjustment process 2400 receives, at block 2422, the blood glucose (BG) measurement (e.g., BGbedtime) that occurs after the dinner meal bolus via Entry Point G of the non-meal aggregation process 2200a (FIG. 7A), and sets BGbedtime as a governing blood glucose BGgov. The meal bolus adjustment process 2400 applies an adjustment factor (AF) function (FIG. 4) at block 2424 using BGbedtime as the BGgov. Specifically, the meal bolus adjustment process 2400 determines the adjustment factor AF at block 2424 as a function of the governing blood glucose BGgov (e.g., BGbedtime). In scenarios when there are an insufficient number of BG measurements for the Bedtime BG time-bucket, i.e., when block 2204 (FIG. 7A) of aggregation process 2200a is "YES", the meal bolus adjustment process 2400, sets, at block 2440, the Adjustment Factor AF equal to 1. The meal bolus adjustment process 2400 receives, at block 2440, the indication of insufficient BG data, i.e., preventing adjustment of the governing dose, from the aggregation process 2200a via Entry Point S. At block 2406, the meal bolus adjustment process 2400 determines the adjustment to the patient's next dinner meal bolus by the following equation:

$$\text{RecomDinnerBol} = (\text{previous RecomDinnerBol}) * AF \qquad (15\text{C})$$

wherein the previous RecomDinnerBol is provided from block 2420. Block 2420 may obtain the previous RecomDinnerBol from block 2442 associated with the merged database 1906 (FIG. 6A) within the non-transitory memory 24, 134, 144. Thereafter, the meal bolus adjustment process 2400 uses the data flow process 1900a (FIG. 6A) to transmit the next recommended dinner bolus to the web-based application 198 of the mobile device 110b or the glucometer 124 via Entry Point Q (FIG. 6A), or directly to the mobile device 110b via Entry Point W (FIG. 6A).

In some implementations, the adjusted meal boluses set forth above may be calculated using the grams of carbohydrate consumed by the patient 10 and the Carbohydrate-to-Insulin Ratio CIR where the Recommended Breakfast, Lunch and Dinner Boluses may be calculated as follows:

$$\text{RecomLunchBolus} = (\text{Carbohydrate } gms \text{ in Lunch}) / CIR \qquad (16\text{A})$$

$$\text{RecomDinnerBol} = (\text{Carbohydrate } gms \text{ in Dinner}) / CIR \qquad (16\text{B})$$

$$\text{RecBreakfastBol} = (\text{Carbohydrate } gms \text{ in Breakfast}) / CIR \qquad (16\text{C})$$

Referring to FIG. 10, a carbohydrate-insulin-ratio (CIR) adjustment process 2500 shows blocks 2502, 2504, 2506 calculating next recommended CIRs for scheduled meal boluses of breakfast, lunch and dinner, respectively. The next recommended CIR for each scheduled meal bolus is based on the blood glucose BG measurement that occurs after the meal bolus associated with the CIR being adjusted.

For calculating the next recommended breakfast CIR (block 2502), the CIR adjustment process 2500 receives, at block 2510, the BG measurement (e.g., BGlunch) that occurs after the breakfast meal bolus via Entry Point H of the aggregation process 2200b (FIG. 7D), and sets the BGlunch as a governing blood glucose BGgov. The CIR adjustment process 2500 applies an adjustment factor (AF) function (FIG. 4) at block 2512 using BGlunch as the BGgov. Specifically, CIR adjustment process 2500 determines the adjustment factor AF at block 2512 as a function of the governing blood glucose BGgov (e.g., BGlunch). In scenarios when there are an insufficient number of BG measurements for the Lunch BG time-bucket, i.e., when block 2234 (FIG. 7D) of aggregation processes 2200b is "YES", the CIR adjustment process 2500, sets, at block 2540, the Adjustment Factor AF equal to 1. The CIR adjustment process 2500 receives, at block 2540, the indication of insufficient BG data, i.e., preventing adjustment of the governing dose, from the aggregation process 2200b via Entry Point S. At block 2502, the CIR adjustment process 2500 determines the adjustment to the patient's breakfast CIR by the following equation:

$$\text{RecomBreakCIR} = (\text{previous RecomBreakCIR}) / AF, \qquad (17\text{A})$$

wherein the previous RecomBreakCIR is provided from block 2508. Block 2508 may obtain the previous RecomBreakCIR from block 2542 associated with the merged database 1906 (FIG. 6A) within the non-transitory memory 24, 134, 144. Thereafter, the CIR adjustment process 2500 uses the data flow process 1900a (FIG. 6A) to transmit the next recommended breakfast CIR to the web-based application 198 of the mobile device 110b or the glucometer 124 via Entry Point Q (FIG. 6A), or directly to the mobile device 110b via Entry Point W (FIG. 6A).

For calculating the next recommended lunch CIR (block 2504), the CIR adjustment process 2500 receives, at block 2516, the BG measurement (e.g., BGdinner) that occurs after the lunch meal bolus via Entry Point H of the aggregation process 2200b (FIG. 7D), and sets the BGdinner as a governing blood glucose BGgov. The CIR adjustment process 2500 applies an adjustment factor (AF) function (FIG. 4) at block 2518 using BGdinner as the BGgov. Specifically, the CIR adjustment process 2500 determines the adjustment factor AF at block 2518 as a function of the governing blood glucose BGgov (e.g., BGdinner). In scenarios when there are an insufficient number of BG measurements for the Dinner BG time-bucket, i.e., when block 2234 (FIG. 7D) of aggregation processes 2200b is "YES", the CIR adjustment process 2500, sets, at block 2540, the Adjustment Factor AF equal to 1. The CIR adjustment process 2500 receives, at block 2540, the indication of insufficient BG data, i.e., preventing adjustment of the governing dose, from the aggregation process 2200b via Entry Point S. At block 2504, the CIR adjustment process 2500 determines the adjustment to the patient's lunch CIR by the following equation:

$$\text{RecomLunch} CIR = (\text{previous RecomLunch} CIR)/AF, \quad (17B)$$

wherein the previous RecomLunchCIR is provided from block 2514. Block 2514 may obtain the previous RecomLunchCIR from block 2542 associated with the merged database 1906 (FIG. 6A) within the non-transitory memory 24, 134, 144. Thereafter, the CIR adjustment process 2500 uses the data flow process 1900a (FIG. 6A) to transmit the next recommended breakfastCIR to the web-based application 198 of the mobile device 110b or the glucometer 124 via Entry Point Q (FIG. 6A), or directly to the mobile device 110b via Entry Point W (FIG. 6A).

For calculating the next recommended CIR dinner bolus (block 2506), the CIR adjustment process 2500 receives, at block 2522, the blood glucose (BG) measurement (e.g., BGbedtime) that occurs after the dinner meal bolus via Entry Point G of the non-meal aggregation process 2200a (FIG. 7A), and sets BGbedtime as a governing blood glucose BGgov. The CIR adjustment process 2500 applies an adjustment factor (AF) function (FIG. 4) at block 2524 using BGbedtime as the BGgov. Specifically, the CIR adjustment process 2500 determines the adjustment factor AF at block 2524 as a function of the governing blood glucose BGgov (e.g., BGbedtime). In scenarios when there are an insufficient number of BG measurements for the Bedtime BG time-bucket, i.e., when block 2204 (FIG. 7A) of aggregation process 2200a is "YES", the CIR adjustment process 2500, sets, at block 2540, the Adjustment Factor AF equal to 1. The CIR adjustment process 2500 receives, at block 2540, the indication of insufficient BG data, i.e., preventing adjustment of the governing dose, from the aggregation process 2200a via Entry Point S. At block 2506, the CIR adjustment process 2500 determines the adjustment to the patient's next dinner CIR by the following equation:

$$\text{RecomDinner} CIR = (\text{previous RecomDinner} CIR)/AF \quad (17C)$$

wherein the previous RecomDinnerCIR is provided from block 2520. Block 2520 may obtain the previous RecomDinnerCIR from block 2542 associated with the merged database 1906 (FIG. 6A) within the non-transitory memory 24, 134, 144. Thereafter, the CIR adjustment process 2500 uses the data flow process 1900a (FIG. 6A) to transmit the next recommended dinner CIR to the web-based application 198 of the mobile device 110b or the glucometer 124 via Entry Point Q (FIG. 6A), or directly to the mobile device 110b via Entry Point W (FIG. 6A).

Figure 11:
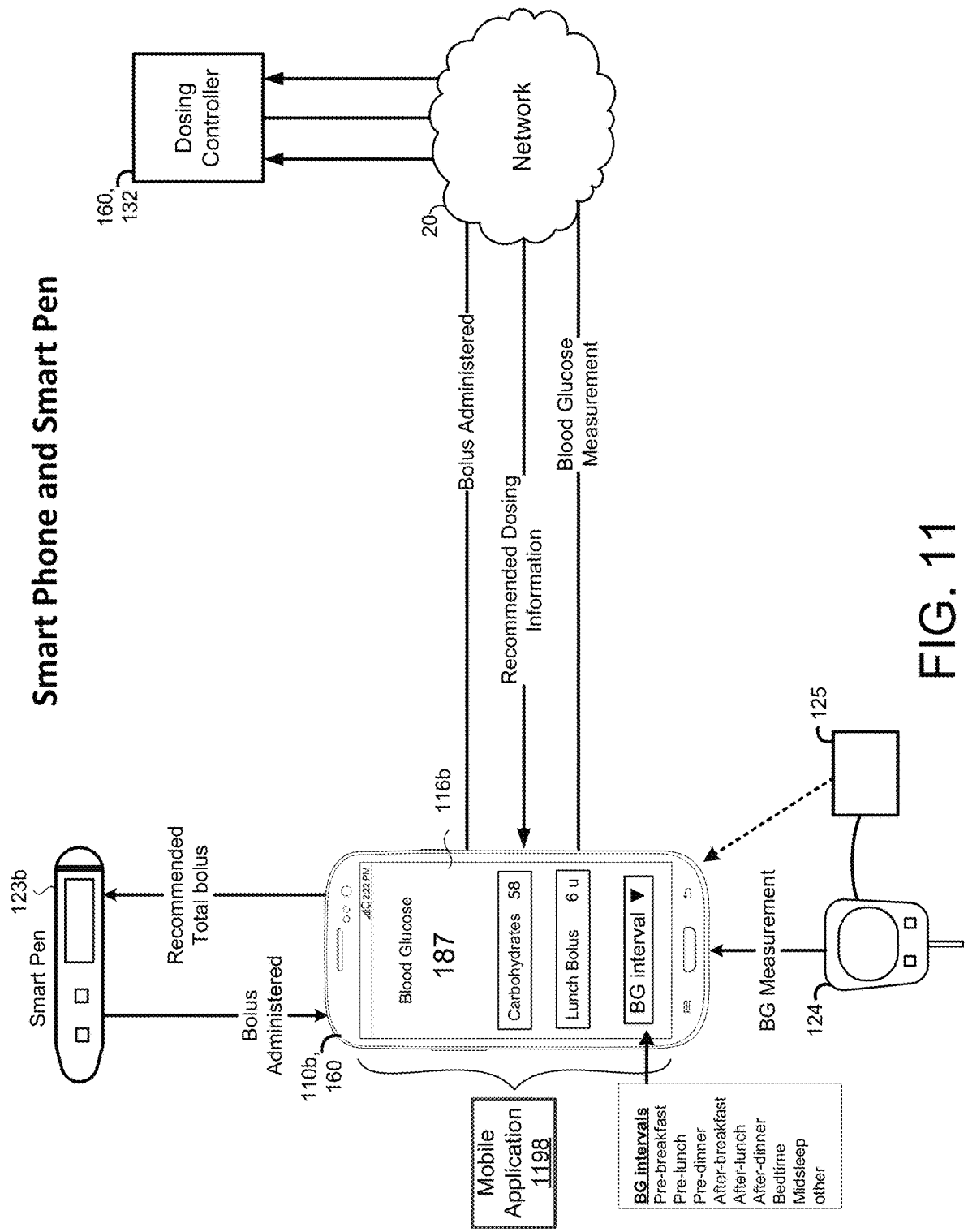
FIG. 11 is a schematic view of exemplary components of the system of FIGS. 1A-1C.

FIG. 11 is a schematic view of exemplary components of the system of FIGS. 1A-1C. FIG. 11 may be described with reference to the SubQ outpatient process 1800b of FIG. 5B. In some implementations, the insulin administration device 123 associated with the patient 10 includes a smart pump 123a or a smart pen 123b that is capable of communicating (e.g., syncing) with a patient device 110 such as a smart phone 110b. In the example shown, the smart pen 123b communicates with the smart phone 110b via Bluetooth, however, other wireless or wired communications are possible. Likewise, in some implementations, the glucometer 124 associated with the patient 10 is capable of communicating blood glucose measurements to the smart phone 110b. The glucometer 124 and smart phone 110b may communicate via Bluetooth, infrared, cable, or any other communications. In some examples, the glucometer 124 communicates with a data translator 125, and the data translator 125 provides the blood glucose measurements from the glucometer 124 to the smart phone 110b. The computing device 112b of the smart phone 110b may execute a mobile application 1198 for communicating with the dosing controller 160 such that information can be communicated over the network 20 between the dosing controller 160 and each of the smart pen 123b and the glucometer 124. For example, dosing parameters adjusted by the dosing controller 160 may be transmitted to the smart phone 110b and stored within memory 114b. The dosing parameters may include, but are not limited to: TargetBG, Correction Factor (CF), CIR for all day, CIR's for each meal, Recommended Breakfast Bolus, Recommended Lunch Bolus, Recommended Dinner Bolus, Recommended Basal doses, number of Basal doses per day, and Basal dose scheduled times. As described above with reference to the data flow process 1900a-c of FIGS. 6A-6C, the dosing parameters may be adjusted automatically or manually initiated by the user 40 or patient 10.

In some implementations, upon the glucometer 124 determining a blood glucose measurement, the glucometer 124 transmits the blood glucose measurement to the smart phone 110b. The smart phone 110b may render the blood glucose measurement upon the display 116b and permit the patient 10 to select the BGtype associated with the blood glucose measurement (e.g., blocks 1804 and 1806 of FIG. 5B). The smart phone 110b may transmit the BG measurement and the BG type to the dosing controller 160 via the network 20. In some implementations, the mobile application 1198 executing on the smart phone 110b calculates a correction bolus (CB) using EQ. 2 based upon the current correction factor (CF) and Target BG stored within the memory 114b. In other implementations, the correction bolus (CB) is calculated using EQ. 10 (block 714 of FIG. 3) by deducting from previously administered doses of insulin that are still active. The CF and Target BG may be provided when a previous dosing parameter adjustment was transmitted to the smart phone 110b from the dosing controller 160.

In some implementations, recommended meal boluses may be determined by the dosing controller 160 and sent to the smart phone 110b during each adjustment transmission and stored within the memory 114b. For example, upon the patient 10 selecting the BG type for a given blood glucose measurement, the mobile application 1198 executing on the smartphone may determine the meal bolus (e.g., breakfast, lunch, or dinner) based upon the BG type without using carb counting for the current meal. In some configurations, the mobile application 1198 executing on the smart phone 110b executes all functionality of the dosing controller 160, thereby eliminating the need for communications over the network. In some examples, when the BG measurement requires the correction bolus, the mobile application 1198 calculates a total bolus (e.g., meal bolus+correction bolus) and transmits the total bolus to the smart pen 123b. In some examples, the smart pen 123b (using the administration computing device 112e, automatically dials in the total bolus for the doser 223b to administer. In some examples, the smart pen 123b receives a recommended total bolus dose from the smart phone 110b transmitted from the computing device 142 of the dosing controller 160 via the network 20. In some examples, upon administration of an insulin dose by the smart pen 123b, the smart pen 123b transmits the value of the administered dose to the smart phone 110b for storage within memory 114a along with the associated BG measurement.

In some examples, the patient 10 may enter a number of carbohydrates for a current meal into the glucometer 124 for transmission to the smart phone 110b or directly into the smart phone 110b when a blood glucose measurement is received. Using a carbohydrate-to-insulin ratio (CIR) transmitted from the dosing controller 160 to the smart phone 110b, the mobile application 1198 executing on the smart phone may calculate the recommended meal bolus (e.g., breakfast, lunch or dinner) using one of the EQ. 16A-16C. In some examples, the CIR and CF are adjusted each time a BG measurement is received at the dosing controller 160 from the glucometer 124 using the smart phone 110b to facilitate the transmission thru the network 20. In other examples, the CIR and CF are adjusted when all the dosing parameters are adjusted (e.g., via the batch download process) and transmitted to the smart phone 110b for storage within the memory 114b.

FIG. 12A shows the display 146 of the health care provider computing system 140 displaying blood glucose data. A plot 502 depicts a modal day scatter chart of blood glucose measurements over a period of time along the x-axis and blood glucose value along the y-axis. In the example shown, a target blood glucose range is depicted in the plot. Computational Information 504 depicts an average for patients' A1C value (6.8%), an average fasting blood glucose value (e.g., 138 mg/dl), an average BGs per day, a percent of BGs Within the target, a total number of patients using basal bolus therapy, a total number of patients using basal/correction therapy, a total number of patients using a pump, and a total number of patients using inhalants. Bar graph 506 depicts a distribution of blood glucose measurements in the target range and pie chart 508 depicts a percentage of patients experiencing varying degrees of hypoglycemia.

FIG. 13 is a schematic view of an exemplary Carbohydrate-Insulin-Ratio (CIR) Adjustment in a Meal-by-Meal process 2600. There is a single variable for CIR. Blocks 2604, 2608, 2610, 2614, 2616 determine whether or not a given meal type is associated with a BGtype for Breakfast, Lunch, Dinner, Bedtime, or MidSleep/Miscellaneous, respectively. For a given meal, e.g. Lunch, the process obtains the CIR, at block 2628 from the previous meal calculations e.g. Breakfast, associated with block 2624 (a few hours previous). The current BG is identified as the Lunch BG at block 2608. The Lunch BG may be only seconds old. The Lunch BG is sent to block 2618 as a governing blood glucose value BGgov for determining an Adjustment Factor AF using the Adjustment Factor Function. Accordingly, at block 2628, the process 2600 calculates the CIR for Lunch by dividing the previous CIR for Breakfast by the AF determined at block 2618. Block 2628 provides the CIR for Lunch to block 2640 for calculating the recommended lunch bolus by dividing an estimated number of carbohydrates to be consumed by the patient by the CIR for lunch. For calculating the CIR for Dinner, block 2632 may use the CIR for Lunch calculated at block 2628. Process 2600 repeats, meal-by-meal, with the exception of the logic flow between Bedtime and Breakfast, whereat the Bedtime BG is ideally placed after Dinner to govern an adjustment to the current CIR. Therefore, the Bedtime BG at block 2614 is the governing BG fed to the AF function at block 2622, and the resulting AF is sent to block 2634. Also the current CIR arrives at 2634 from the CIR for Dinner calculated at block 2632. The calculation at block 2634 involves dividing the current CIR by the AF to obtain a newly adjusted value of the CIR. In some implementations, a Bedtime snack is allowed, using this value of the CIR. This value of the CIR (governed by the Bedtime BG) is passed without further adjustment to the Breakfast calculations the next day. In some implementations, an additional CIR adjustment may be governed by the MidSleep BG.

Figure 14:
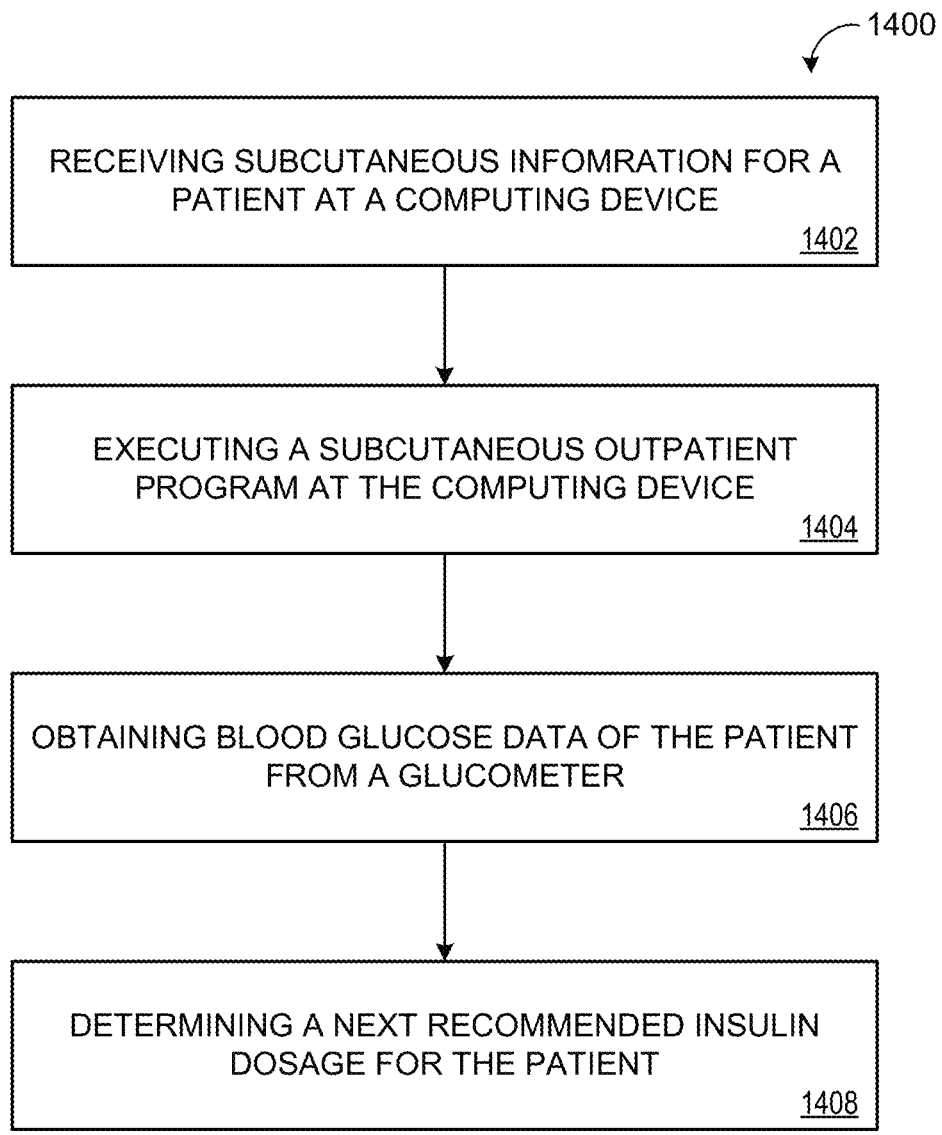
FIG. 14 is an exemplary arrangement of operations for administering insulin.

Referring to FIG. 14, a method 1400 of administering insulin using a subcutaneous (SubQ) outpatient process 1800 includes receiving 1402 subcutaneous information 216 for a patient 10 at a computing device 112, 132, 142. The method 1400 executes 1404 the SubQ outpatient process 1800. The method 1400 includes obtaining 1406 blood glucose data of the patient 124 from a glucometer 124 in communication with the computing device 112, 132, 142. The blood glucose data includes blood glucose measurements of the patient 10 and/or doses of insulin administered by the patient 10 associated with each blood glucose measurement. The method 1400 includes the computing device 112, 132, 142 determining 1408 a next recommended insulin dosage for the patient 10 based on the obtained blood glucose data and the subcutaneous information 216a. The method further includes 1400 the computing device 112, 132, 142 transmitting the next recommended insulin dosage to a portable device associated with the patient 10. The portable device 110a-e displays the next recommended insulin dose.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor and can be implemented in a high-level procedural and/or object-oriented programming language, and/or in assembly/machine language. As used herein, the terms "machine-readable medium" and "computer-readable medium" refer to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term "machine-readable signal" refers to any signal used to provide machine instructions and/or data to a programmable processor.

Implementations of the subject matter and the functional operations described in this specification can be implemented in digital electronic circuitry, or in computer software, firmware, or hardware, including the structures disclosed in this specification and their structural equivalents, or in combinations of one or more of them. Moreover, subject matter described in this specification can be implemented as one or more computer program products, i.e., one or more modules of computer program instructions encoded on a computer readable medium for execution by, or to control the operation of, data processing apparatus. The computer readable medium can be a machine-readable storage device, a machine-readable storage substrate, a memory device, a composition of matter affecting a machine-readable propagated signal, or a combination of one or more of them. The terms "data processing apparatus", "computing device" and "computing processor" encompass all apparatus, devices, and machines for processing data, including by way of example a programmable processor, a computer, or multiple processors or computers. The apparatus can include, in addition to hardware, code that creates an execution environment for the computer program in question, e.g., code that constitutes processor firmware, a protocol stack, a database management system, an operating system, or a combination of one or more of them. A propagated signal is an artificially generated signal, e.g., a machine-generated electrical, optical, or electromagnetic signal that is generated to encode information for transmission to suitable receiver apparatus.

A computer program (also known as an application, program, software, software application, script, or code) can be written in any form of programming language, including compiled or interpreted languages, and it can be deployed in any form, including as a stand-alone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Moreover, a computer can be embedded in another device, e.g., a mobile telephone, a personal digital assistant (PDA), a mobile audio player, a Global Positioning System (GPS) receiver, to name just a few. Computer readable media suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto optical disks; and CD ROM and DVD-ROM disks. The processor and the memory can be supplemented by, or incorporated in, special purpose logic circuitry.

To provide for interaction with a user, one or more aspects of the disclosure can be implemented on a computer having a display device, e.g., a CRT (cathode ray tube), LCD (liquid crystal display) monitor, or touch screen for displaying information to the user and optionally a keyboard and a pointing device, e.g., a mouse or a trackball, by which the user can provide input to the computer. Other kinds of devices can be used to provide interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

One or more aspects of the disclosure can be implemented in a computing system that includes a backend component, e.g., as a data server, or that includes a middleware component, e.g., an application server, or that includes a frontend component, e.g., a client computer having a graphical user interface or a Web browser through which a user can interact with an implementation of the subject matter described in this specification, or any combination of one or more such backend, middleware, or frontend components. The components of the system can be interconnected by any form or medium of digital data communication, e.g., a communication network. Examples of communication networks include a local area network ("LAN") and a wide area network ("WAN"), an inter-network (e.g., the Internet), and peer-to-peer networks (e.g., ad hoc peer-to-peer networks).

The computing system can include clients and servers. A client and server are generally remote from each other and typically interact through a communication network. The relationship of client and server arises by virtue of computer programs running on the respective computers and having a client-server relationship to each other. In some implementations, a server transmits data (e.g., an HTML page) to a client device (e.g., for purposes of displaying data to and receiving user input from a user interacting with the client device). Data generated at the client device (e.g., a result of the user interaction) can be received from the client device at the server.

While this specification contains many specifics, these should not be construed as limitations on the scope of the disclosure or of what may be claimed, but rather as descriptions of features specific to particular implementations of the disclosure. Certain features that are described in this specification in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a sub-combination or variation of a sub-combination.

Similarly, while operations are depicted in the drawings in a particular order, this should not be understood as requiring that such operations be performed in the particular order shown or in sequential order, or that all illustrated operations be performed, to achieve desirable results. In certain circumstances, multi-tasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products.

A number of implementations have been described. Nevertheless, it will be understood that various modifications may be made without departing from the spirit and scope of the disclosure. Accordingly, other implementations are within the scope of the following claims. For example, the actions recited in the claims can be performed in a different order and still achieve desirable results.

What is claimed is:

1. A method comprising:
   receiving, at data processing hardware of a patient device, glucose data of a patient associated with the patient device, the glucose data including glucose measurements of the patient and glucose times associated with the glucose measurements;
   transmitting, by the data processing hardware, the glucose data to a remote server, the remote server executing a subcutaneous outpatient process configured to:
      receive sequential scheduled glucose time intervals throughout a day, each scheduled glucose time interval associated with a corresponding adjustable time boundary that does not overlap with other time boundaries associated with the other scheduled glucose time intervals;
      for each scheduled glucose time interval, aggregate the glucose measurements of the glucose data received from the patient device that are associated with the corresponding scheduled glucose time interval based on the glucose times to determine a corresponding representative aggregate glucose measurement associated with the corresponding scheduled glucose time interval; and
      determine a next recommended carbohydrate-to-insulin ratio for the patient during a selected time interval based on the representative aggregate glucose measurement associated with the scheduled glucose time interval that occurs immediately after the selected time interval;
   receiving, at the data processing hardware, the next recommended carbohydrate-to-insulin ratio for the patient during the selected time interval from the remote server;
   executing, by the data processing hardware, an insulin management program configured to display on a display of the patient device in communication with the data processing hardware a graphical user interface having a carbohydrate input field, wherein the insulin management program is configured to:
      receive, at the carbohydrate input field, a total number of carbohydrates consumed by the patient during the selected time interval;
      determine, based on the number of carbohydrates consumed by the patient and the next recommended carbohydrate-to-insulin ratio for the patient during the selected time interval, a recommended meal bolus for the patient to administer during the selected time interval; and
      display, during the selected time interval, the recommended meal bolus on the display of the patient device; and
   transmitting the recommended meal bolus from the data processing hardware to an administration device in communication with the data processing hardware, the administration device configured to automatically dial in a number of units of insulin for the recommended meal bolus and administer the number of units of insulin for the recommended meal bolus.

2. The method of claim 1, wherein the subcutaneous outpatient process is configured to receive the sequential scheduled glucose time intervals throughout the day from a healthcare provider computing device in communication with the remote server.

3. The method of claim 1, further comprising displaying, by the data processing hardware, the number of carbohydrates consumed by the patient during the selected time interval on the display of the patient device.

4. The method of claim 1, wherein receiving the glucose data comprises receiving the glucose data from a remote computing device in communication with the data processing hardware during a batch download process, the remote computing device executing a download program for downloading the glucose data from a glucometer or a continuous glucose monitoring system associated with the patient.

5. The method of claim 1, wherein the administration device comprises a smart insulin pen.

6. The method of claim 1, wherein the administration device comprises an insulin pump.

7. The method of claim 1, wherein the subcutaneous outpatient process is further configured to:
   aggregate one or more of the glucose measurements associated with a selected one of the scheduled glucose time intervals to determine a representative aggregate glucose measurement associated with the selected scheduled glucose time interval;
   select a governing glucose as the representative aggregate glucose measurement associated with the selected scheduled glucose time interval;
   determine an adjustment factor for adjusting a next recommended meal bolus governed by the selected scheduled glucose time interval based on the selected governing glucose measurement;
   obtain a previous day recommended meal bolus governed by the selected scheduled glucose time interval; and
   determine the next recommended meal bolus by multiplying the adjustment factor times the previous day recommended meal bolus.

8. The method of claim 1, wherein the representative aggregate glucose measurement includes one of:
   a mean glucose value for the associated scheduled glucose time interval; or
   a median glucose value for the associated scheduled glucose time interval.

9. A patient device comprising:
   data processing hardware; and
   memory hardware in communication with the data processing hardware, the memory hardware storing instructions that when executed on the data processing hardware cause the data processing hardware to perform operations comprising:
      receiving glucose data of a patient associated with the patient device, the glucose data including glucose measurements of the patient and glucose times associated with the glucose measurements;
      transmitting the glucose data to a remote server, the remote server executing a subcutaneous outpatient process configured to:
      receive sequential scheduled glucose time intervals throughout a day, each scheduled glucose time interval associated with a corresponding adjustable time boundary that does not overlap with other time boundaries associated with the other scheduled glucose time intervals;

for each scheduled glucose time interval, aggregate the glucose measurements of the glucose data received from the patient device that are associated with the corresponding scheduled glucose time interval based on the glucose times to determine a corresponding representative aggregate glucose measurement associated with the corresponding scheduled glucose time interval; and determine a next recommended carbohydrate-to-insulin ratio for the patient during a selected time interval based on the representative aggregate glucose measurement associated with the scheduled glucose time interval that occurs immediately after the selected time interval;

receiving the next recommended carbohydrate-to-insulin ratio for the patient during the selected time interval from the remote server;

executing an insulin management program configured to display on a display of the patient device in communication with the data processing hardware a graphical user interface having a carbohydrate input field, wherein the insulin management program is configured to:

receive, at the carbohydrate input field, a total number of carbohydrates consumed by the patient during the selected time interval;

determine, based on the number of carbohydrates consumed by the patient and the next recommended carbohydrate-to-insulin ratio for the patient during the selected time interval, a recommended meal bolus for the patient to administer during the selected time interval; and display, during the selected time interval, the recommended meal bolus on the display of the patient device; and transmitting the recommended meal bolus from the data processing hardware to an administration device in communication with the data processing hardware, the administration device configured to automatically dial in a number of units of insulin for the recommended meal bolus and administer the number of units of insulin for the recommended meal bolus.

10. The patient device of claim 9, wherein the subcutaneous outpatient process is configured to receive the sequential scheduled glucose time intervals throughout the day from a healthcare provider computing device in communication with the remote server.

11. The patient device of claim 9, wherein the operations further comprise displaying the number of carbohydrates consumed by the patient during the selected time interval on the display of the patient device.

12. The patient device of claim 9, wherein receiving the glucose data comprises receiving the glucose data from a remote computing device in communication with the data processing hardware during a batch download process, the remote computing device executing a download program for downloading the glucose data from a glucometer or a continuous glucose monitoring system associated with the patient.

13. The patient device of claim 9, wherein the administration device comprises a smart insulin pen.

14. The patient device of claim 9, wherein the subcutaneous outpatient process is further configured to:

aggregate one or more of the glucose measurements associated with a selected one of the scheduled glucose time intervals to determine a representative aggregate glucose measurement associated with the selected scheduled glucose time interval;

select a governing glucose as the representative aggregate glucose measurement associated with the selected scheduled glucose time interval;

determine an adjustment factor for adjusting a next recommended meal bolus governed by the selected scheduled glucose time interval based on the selected governing glucose measurement;

obtain a previous day recommended meal bolus governed by the selected scheduled glucose time interval; and determine the next recommended meal bolus by multiplying the adjustment factor times the previous day recommended meal bolus.

15. The patient device of claim 9, wherein the representative aggregate glucose measurement includes one of:

a mean glucose value for the associated scheduled glucose time interval; or a median glucose value for the associated scheduled glucose time interval.

* * * * *